(12) United States Patent
Becker et al.

(10) Patent No.: US 8,183,359 B2
(45) Date of Patent: May 22, 2012

(54) KITS FOR AMPLIFYING DNA

(75) Inventors: Michael M. Becker, San Diego, CA (US); Wai-Chung Lam, Bonsall, CA (US); Kristin W. Livezey, Encinitas, CA (US)

(73) Assignee: Gen-Probe Incorporated, San Diego, CA (US)

( * ) Notice: Subject to any disclaimer, the term of this patent is extended or adjusted under 35 U.S.C. 154(b) by 125 days.

(21) Appl. No.: 12/716,052

(22) Filed: Mar. 2, 2010

(65) Prior Publication Data

US 2010/0159561 A1 Jun. 24, 2010

Related U.S. Application Data

(62) Division of application No. 11/681,104, filed on Mar. 1, 2007, now Pat. No. 7,713,697.

(51) Int. Cl.
*C07H 21/04* (2006.01)
(52) U.S. Cl. ..................................... 536/24.3
(58) Field of Classification Search ................ None
See application file for complete search history.

(56) References Cited

U.S. PATENT DOCUMENTS

| | | |
|---|---|---|
| 5,030,557 A | 7/1991 | Hogan et al. |
| 5,130,238 A | 7/1992 | Malek et al. |
| 5,169,766 A | 12/1992 | Schuster et al. |
| 5,399,491 A | 3/1995 | Kacian et al. |
| 5,409,818 A | 4/1995 | Davey et al. |
| 5,466,586 A | 11/1995 | Davey et al. |
| 5,554,516 A | 9/1996 | Kacian et al. |
| 5,554,517 A | 9/1996 | Davey et al. |
| 5,573,906 A | 11/1996 | Bannwarth et al. |
| 5,766,849 A | 6/1998 | McDonough et al. |
| 5,786,183 A | 7/1998 | Ryder et al. |
| 5,824,518 A | 10/1998 | Kacian et al. |
| 5,849,497 A | 12/1998 | Steinman |
| 5,925,517 A | 7/1999 | Tyagi et al. |
| 6,031,091 A | 2/2000 | Arnold, Jr. et al. |
| 6,033,851 A | 3/2000 | Yamane |
| 6,090,591 A | 7/2000 | Burg et al. |
| 6,130,038 A | 10/2000 | Becker et al. |
| 6,150,097 A | 11/2000 | Tyagi et al. |
| 6,268,490 B1 | 7/2001 | Imanishi et al. |
| 6,410,276 B1 | 6/2002 | Burg et al. |
| 6,534,274 B2 | 3/2003 | Becker et al. |
| 6,582,938 B1 | 6/2003 | Su et al. |
| 6,670,461 B1 | 12/2003 | Wengel et al. |
| 7,374,885 B2 | 5/2008 | Becker et al. |
| 7,696,337 B2 | 4/2010 | Becker et al. |
| 7,713,697 B2 | 5/2010 | Becker et al. |
| 2003/0017591 A1 | 1/2003 | Kurn |
| 2003/0087251 A1 | 5/2003 | Kurn |
| 2003/0194723 A1 | 10/2003 | Cunningham et al. |
| 2004/0023271 A1 | 2/2004 | Kurn et al. |
| 2004/0175729 A1 | 9/2004 | Hiyama |
| 2004/0203019 A1 | 10/2004 | Kurn |
| 2007/0281317 A1 | 12/2007 | Becker et al. |
| 2007/0299254 A1 | 12/2007 | Becker et al. |
| 2008/0131875 A1 | 6/2008 | Hall |
| 2009/0170168 A1 | 7/2009 | Becker et al. |

FOREIGN PATENT DOCUMENTS

| | | |
|---|---|---|
| JP | 09065880 A | 3/1997 |
| WO | 88/10315 A1 | 12/1988 |
| WO | 96/01327 A1 | 1/1996 |
| WO | 98/02449 A1 | 1/1998 |
| WO | 00/71652 A2 | 11/2000 |
| WO | 2004/048594 A2 | 6/2004 |
| WO | 2006/026388 A2 | 3/2006 |
| WO | 2008/045251 A | 4/2008 |

OTHER PUBLICATIONS

EPO Office Action, European Patent Application No. 05 791 220.6, Jan. 26, 2011.

Ayala et al. "New Primer Strategy Improves Precision of Differential Display," BioTechniques, 1995, 18(5):842-844, 846, 848, 850, Informa Healthcare USA, Inc., U.K.

Bonnet et al., "Thermodynamic basis of the chemical specificity of structured DNA probes," Proc. Natl. Acad. Sci. USA, 1999, 96:6171-6176, National Academy of Sciences, USA.

Caetano-Anolies et al., "DNA Amplification Fingerprinting Using Arbitrary Mini-hairpin Oligonucleotide Primers," Bio/Technology, 1994, 12:619-623, Nature Pub. Co., USA.

Ikeda et al., "Initiation of Transcription by T7 RNA Polymerase at Its Natural Promoters," J. Biol. Chem., 1992, 267 (4):2640-2649, American Society for Biochemistry and Molecular Biology, Baltimore, MD, USA.

Latorra et al., "Design considerations and effects of LNA in PCR primers," Mol. Cell. Probes, 2003, 17:253-259, Elsevier, New York, USA.

Majlessi et al., "Advantages of 2'-O-methyl oligoribonucleotide probes for detecting RNA targets," Nucleic Acids Res., 1998, 26(9):2224-2229, Oxford University Press, Oxford, UK.

(Continued)

*Primary Examiner* — Kenneth R. Horlick
*Assistant Examiner* — David Thomas
(74) *Attorney, Agent, or Firm* — Charles B. Cappellari

(57) ABSTRACT

Kits for amplifying DNA which include a priming oligonucleotide that hybridizes to a 3'-end of a DNA target sequence, a displacer oligonucleotide that hybridizes to a target nucleic acid containing the DNA target sequence at a position upstream from the priming oligonucleotide, and a promoter oligonucleotide that includes a region that hybridizes to a 3'-region of a DNA primer extension product that includes the priming oligonucleotide and a promoter for an RNA polymerase. The priming oligonucleotide does not include an RNA region that hybridizes to the target nucleic acid and is selectively degraded by an enzyme activity when hybridized to the target nucleic acid. The kits do not include a restriction endonuclease and oligonucleotides that include a promoter for an RNA polymerase are all modified to prevent the initiation of DNA synthesis therefrom.

35 Claims, 18 Drawing Sheets

OTHER PUBLICATIONS

Patel et al., "Formation of chimeric DNA primer extension products by template switching onto an annealed downstream oligonucleotide," Proc. Natl. Acad. Sci. USA, 93:2969-2974, National Academy of Sciences, USA, 1996.

Petersen et al., "The conformations of locked nucleic acids (LNA)," J. Mol. Recognit., 2000, 13:44-53, John Wiley & Sons, Ltd., London, UK.

Scaramozzino et al., "Comparison of Flavivirus Universal Primer Pairs and Development of a Rapid, Highly Sensitive Heminested Reverse Transcriptase-PCR Assay for Detection of Flaviviruses Targeted to a Conserved Region of the NS5 Gene Sequences," J. Clin. Microbiol., 2001, 39(5):1922-1927, American Society for Microbiology, USA.

USPTO Office Action, U.S. Appl. No. 11/681,104, Apr. 28, 2009.

USPTO Notice of Allowance, U.S. Appl. No. 11/681,104, Dec. 2, 2009.

EPO Search Report, European Patent Application No. 07757746.8, Oct. 12, 2010.

PCT Search Report, International Application No. PCT/US07/63103, Aug. 19, 2008.

PCT Written Opinion, International Application No. PCT/US07/63103, Aug. 19, 2008.

PCT International Preliminary Report On Patentability, International Application No. PCT/US07/063103, Sep. 11, 2009.

SEQUENCE LISTING

<160> NUMBER OF SEQ ID NOS: 59

<210> SEQ ID NO 1
<211> LENGTH: 6
<212> TYPE: DNA
<213> ORGANISM: Artificial

```
<220> FEATURE:
<223> OTHER INFORMATION: Insertion sequence for promoter oligonucleotide

<400> SEQUENCE: 1 ccacaa                                                                    6

<210> SEQ ID NO 2
<211> LENGTH: 11
<212> TYPE: DNA
<213> ORGANISM: Artificial
<220> FEATURE:
<223> OTHER INFORMATION: Insertion sequence for promoter oligonucleotide

<400> SEQUENCE: 2
acgtagcatc c                                                             11

<210> SEQ ID NO 3
<211> LENGTH: 27
<212> TYPE: DNA
<213> ORGANISM: Artificial
<220> FEATURE:
<223> OTHER INFORMATION: T7 RNA polymerase promoter sequence

<400> SEQUENCE: 3
aatttaatac gactcactat agggaga                                            27

<210> SEQ ID NO 4
<211> LENGTH: 32
<212> TYPE: DNA
<213> ORGANISM: Artificial
<220> FEATURE:
<223> OTHER INFORMATION: Target binding portion of promoter
      oligonucleotide for 5' untranslated region of HCV

<400> SEQUENCE: 4
ctagccatgg cgttagtatg agtgtcgtgc ag                                      32

<210> SEQ ID NO 5
<211> LENGTH: 59
<212> TYPE: DNA
<213> ORGANISM: Artificial
<220> FEATURE:
<223> OTHER INFORMATION: Promoter oligonucleotide for 5' untranslated
      region of HCV

<400> SEQUENCE: 5
aatttaatac gactcactat agggagacta gccatggcgt tagtatgagt gtcgtgcag         59

<210> SEQ ID NO 6
<211> LENGTH: 31
<212> TYPE: DNA
<213> ORGANISM: Artificial
<220> FEATURE:
<223> OTHER INFORMATION: Priming oligonucleotide for 5' untranslated
      region of HCV

<400> SEQUENCE: 6
aggcattgag cgggttgatc caagaaagga c                                       31

<210> SEQ ID NO 7
<211> LENGTH: 15
<212> TYPE: RNA
<213> ORGANISM: Artificial
<220> FEATURE:
<223> OTHER INFORMATION: Detection probe for 5' untranslated region of
      HCV
<220> FEATURE:
<221> NAME/KEY: misc_feature
```

-continued

```
<222> LOCATION: (1)..(15)
<223> OTHER INFORMATION: 2'O-methylribonucleotides

<400> SEQUENCE: 7
guacucaccg guucc                                                      15

<210> SEQ ID NO 8
<211> LENGTH: 22
<212> TYPE: RNA
<213> ORGANISM: Artificial
<220> FEATURE:
<223> OTHER INFORMATION: Detection probe for 5' untranslated region of
      HCV
<220> FEATURE:
<221> NAME/KEY: misc_feature
<222> LOCATION: (1)..(22)
<223> OTHER INFORMATION: 2'-O-methylribonucleotides

<400> SEQUENCE: 8
agaccacuau ggcucucccg gg                                              22

<210> SEQ ID NO 9
<211> LENGTH: 31
<212> TYPE: DNA
<213> ORGANISM: Artificial
<220> FEATURE:
<223> OTHER INFORMATION: Target binding portion of promoter
      oligonucleotide for HIV pol gene

<400> SEQUENCE: 9
acaaatggca gtattcatcc acaatttaaa a                                    31

<210> SEQ ID NO 10
<211> LENGTH: 59
<212> TYPE: DNA
<213> ORGANISM: Artificial
<220> FEATURE:
<223> OTHER INFORMATION: Promoter oligonucleotide for HIV pol gene

<400> SEQUENCE: 10
aatttaatac gactcactat agggagacta gccatggcgt tagtatgagt gtcgtgcag      59

<210> SEQ ID NO 11
<211> LENGTH: 27
<212> TYPE: DNA
<213> ORGANISM: Artificial
<220> FEATURE:
<223> OTHER INFORMATION: Priming oligoncueleotide for HIV pol gene

<400> SEQUENCE: 11
gtttgtatgt ctgttgctat tatgtct                                         27

<210> SEQ ID NO 12
<211> LENGTH: 17
<212> TYPE: RNA
<213> ORGANISM: Artificial
<220> FEATURE:
<223> OTHER INFORMATION: Detection probe for HIV pol gene
<220> FEATURE:
<221> NAME/KEY: misc_feature
<222> LOCATION: (1)..(17)
<223> OTHER INFORMATION: 2'-O-methylribonucleotides

<400> SEQUENCE: 12
acuguacccc ccaaucc                                                    17

<210> SEQ ID NO 13
<211> LENGTH: 27
```

```
<212> TYPE: DNA
<213> ORGANISM: Artificial
<220> FEATURE:
<223> OTHER INFORMATION: Target binding portion of promoter
      oligonucleotide for E6 and E7 genes of HPV

<400> SEQUENCE: 13
gaacagatgg ggcacacaat tcctagt                                            27

<210> SEQ ID NO 14
<211> LENGTH: 54
<212> TYPE: DNA
<213> ORGANISM: Artificial
<220> FEATURE:
<223> OTHER INFORMATION: Promoter oligonucleotide for E6 and E7 genes of
      HPV

<400> SEQUENCE: 14
aatttaatac gactcactat agggagagaa cagatggggc acacaattcc tagt              54

<210> SEQ ID NO 15
<211> LENGTH: 19
<212> TYPE: DNA
<213> ORGANISM: Artificial
<220> FEATURE:
<223> OTHER INFORMATION: Priming oligonucleotide for E6 and E7 genes of
      HPV

<400> SEQUENCE: 15
gacagctcag aggaggagg                                                     19

<210> SEQ ID NO 16
<211> LENGTH: 19
<212> TYPE: RNA
<213> ORGANISM: Artificial
<220> FEATURE:
<223> OTHER INFORMATION: Detection probe for E6 and E7 genes of HPV
<220> FEATURE:
<221> NAME/KEY: misc_feature
<222> LOCATION: (1)..(19)
<223> OTHER INFORMATION: 2'-O-methylribonucleotides

<400> SEQUENCE: 16
ggacaagcag aaccggaca                                                     19

<210> SEQ ID NO 17
<211> LENGTH: 27
<212> TYPE: DNA
<213> ORGANISM: Artificial
<220> FEATURE:
<223> OTHER INFORMATION: Target binding portion of promoter
      oligonucleotide for WNV nonstructural protein S gene

<400> SEQUENCE: 17
gagtagacgg tgctgcctgc gactcaa                                            27

<210> SEQ ID NO 18
<211> LENGTH: 58
<212> TYPE: DNA
<213> ORGANISM: Artificial
<220> FEATURE:
<223> OTHER INFORMATION: Promoter oligonucleotide for WNV nonstructural
      protein S gene

<400> SEQUENCE: 18
aatttaatac gactcactca ctatagggag agagtagacg gtgctgcctg cgactcaa          58

<210> SEQ ID NO 19
```

```
<211> LENGTH: 23
<212> TYPE: DNA
<213> ORGANISM: Artificial
<220> FEATURE:
<223> OTHER INFORMATION: Priming oligonucleotide for WNV nonstructural protein S gene
<400> SEQUENCE: 19
tccgagacgg ttctgagggc tta 23

<210> SEQ ID NO 20
<211> LENGTH: 18
<212> TYPE: RNA
<213> ORGANISM: Artificial
<220> FEATURE:
<223> OTHER INFORMATION: Detection probe for WNV nonstructural protein S gene
<220> FEATURE:
<221> NAME/KEY: misc_feature
<222> LOCATION: (1)..(18)
<223> OTHER INFORMATION: 2'-O-methylribonucleotides
<400> SEQUENCE: 20
gaucacuucg cggcuuug 18

<210> SEQ ID NO 21
<211> LENGTH: 30
<212> TYPE: DNA
<213> ORGANISM: Artificial
<220> FEATURE:
<223> OTHER INFORMATION: Target binding portion of promoter oligonucleotide for 23S rRNA of Chlamydia trachomatis
<400> SEQUENCE: 21
cggagtaagt taagcacgcg gacgattgga 30

<210> SEQ ID NO 22
<211> LENGTH: 57
<212> TYPE: DNA
<213> ORGANISM: Artificial
<220> FEATURE:
<223> OTHER INFORMATION: Promoter oligonucleotide for 23S rRNA of Chlamydia trachomatis
<400> SEQUENCE: 22
aatttaatac gactcactat agggagacgg agtaagttaa gcacgcggac gattgga 57

<210> SEQ ID NO 23
<211> LENGTH: 29
<212> TYPE: DNA
<213> ORGANISM: Artificial
<220> FEATURE:
<223> OTHER INFORMATION: Priming oligonucleotide for 23S rRNA of Chlamydia trachomatis
<400> SEQUENCE: 23
cccgaagatt ccccttgatc gcgacctga 29

<210> SEQ ID NO 24
<211> LENGTH: 24
<212> TYPE: RNA
<213> ORGANISM: Artificial
<220> FEATURE:
<223> OTHER INFORMATION: Detection probe for 23S rRNA of Chlamydia trachomatis
<220> FEATURE:
<221> NAME/KEY: misc_feature
<222> LOCATION: (1)..(24)
<223> OTHER INFORMATION: 2'-O-methylribonucleotides

```
<400> SEQUENCE: 24
cguucucauc gcucuacgga cucu                                          24

<210> SEQ ID NO 25
<211> LENGTH: 36
<212> TYPE: DNA
<213> ORGANISM: Artificial
<220> FEATURE:
<223> OTHER INFORMATION: Target binding portion of promoter
      oligonucleotide for 16S rRNA of Mycobacterium tuberculosis

<400> SEQUENCE: 25
actgggtcta ataccggata ggaccacggg atgcat                             36

<210> SEQ ID NO 26
<211> LENGTH: 64
<212> TYPE: DNA
<213> ORGANISM: Artificial
<220> FEATURE:
<223> OTHER INFORMATION: Promoter oligonucleotide for 16S rRNA of
      Mycobacterium tuberculosis

<400> SEQUENCE: 26 aatt

```
<221> NAME/KEY: misc_feature
<222> LOCATION: (1)..(22)
<223> OTHER INFORMATION: 2'-O-methylribonucleotides

<400> SEQUENCE: 30
gcucauccca caccgcuaaa gc                                                  22

<210> SEQ ID NO 31
<211> LENGTH: 28
<212> TYPE: RNA
<213> ORGANISM: Artificial
<220> FEATURE:
<223> OTHER INFORMATION: Detection probe for 16S rRNA of Mycobacterium
      tuberculosis
<220> FEATURE:
<221> NAME/KEY: misc_feature
<222> LOCATION: (1)..(28)
<223> OTHER INFORMATION: 2'-O-methylribonucleotides

<400> SEQUENCE: 31
ccgagauccc acaccgcuaa agccucgg                                            28

<210> SEQ ID NO 32
<211> LENGTH: 22
<212> TYPE: DNA
<213> ORGANISM: Artificial
<220> FEATURE:
<223> OTHER INFORMATION: Detection probe for 16S rRNA of Mycobacterium
      tuberculosis

<400> SEQUENCE: 32
gctcatccca caccgctaaa gc                                                  22

<210> SEQ ID NO 33
<211> LENGTH: 24
<212> TYPE: DNA
<213> ORGANISM: Artificial
<220> FEATURE:
<223> OTHER INFORMATION: Target binding portion of promoter
      oligonucleotide for orfX gene of Staphylococcus aureus

<400> SEQUENCE: 33
tgacccaagg gcaaagcgac tttg                                                24

<210> SEQ ID NO 34
<211> LENGTH: 51
<212> TYPE: DNA
<213> ORGANISM: Artificial
<220> FEATURE:
<223> OTHER INFORMATION: Promoter oligonucleotide for orfX gene of
      Staphylococcus aureus

<400> SEQUENCE: 34
aatttaatac gactcactat agggagatga cccaagggca aagcgacttt g                  51

<210> SEQ ID NO 35
<211> LENGTH: 28
<212> TYPE: DNA
<213> ORGANISM: Artificial
<220> FEATURE:
<223> OTHER INFORMATION: Priming oligonucleotide for orfX gene of
      Staphylococcus aureus

<400> SEQUENCE: 35
gtgcgtagtt actgcgttgt aagacgtc                                            28

<210> SEQ ID NO 36
<211> LENGTH: 26
```

```
<212> TYPE: DNA
<213> ORGANISM: Artificial
<220> FEATURE:
<223> OTHER INFORMATION: Priming oligonucleotide for orfX gene of
      Staphylococcus aureus

<400> SEQUENCE: 36
ctgaatgata gtgcgtagtt actgcg                                          26

<210> SEQ ID NO 37
<211> LENGTH: 17
<212> TYPE: RNA
<213> ORGANISM: Artificial
<220> FEATURE:
<223> OTHER INFORMATION: Detection probe for orfX gene of Staphylococcus
      aureus
<220> FEATURE:
<221> NAME/KEY: misc_feature
<222> LOCATION: (1)..(17)
<223> OTHER INFORMATION: 2'-O-methylribonucleotides

<400> SEQUENCE: 37
ccgucauugg cggauca                                                    17

<210> SEQ ID NO 38
<211> LENGTH: 24
<212> TYPE: RNA
<213> ORGANISM: Artificial
<220> FEATURE:
<223> OTHER INFORMATION: Terminating oligonucleotide for 5' untranslated
      region of HCV
<220> FEATURE:
<221> NAME/KEY: misc_feature
<222> LOCATION: (1)..(24)
<223> OTHER INFORMATION: 2'-O-methylribonucleotides

<400> SEQUENCE: 38
ggcuagacgc uuucugcgug aaga                                            24

<210> SEQ ID NO 39
<211> LENGTH: 22
<212> TYPE: RNA
<213> ORGANISM: Artificial
<220> FEATURE:
<223> OTHER INFORMATION: Terminating oligonucleotide for 16S rRNA of
      Mycobacterium tuberculosis
<220> FEATURE:
<221> NAME/KEY: misc_feature
<222> LOCATION: (1)..(22)
<223> OTHER INFORMATION: 2'-O-methylribonucleotides

<400> SEQUENCE: 39
cccaguuucc caggcuuauc cc                                              22

<210> SEQ ID NO 40
<211> LENGTH: 15
<212> TYPE: DNA
<213> ORGANISM: Artificial
<220> FEATURE:
<223> OTHER INFORMATION: Detection probe for antisense T7 RNA polymerase
      promoter sequence

<400> SEQUENCE: 40
atacgactca ctata                                                      15

<210> SEQ ID NO 41
<211> LENGTH: 22
<212> TYPE: RNA
<213> ORGANISM: Artificial
<220> FEATURE:
```

```
<223> OTHER INFORMATION: Terminating oligonucleotide for 23S rRNA of
      Chlamydia trachomatis
<220> FEATURE:
<221> NAME/KEY: misc_feature
<222> LOCATION: (1)..(22)
<223> OTHER INFORMATION: 2'-O-methylribonucleotides

<400> SEQUENCE: 41
uccgucauuc uuucgcuaua gu                                            22

<210> SEQ ID NO 42
<211> LENGTH: 24
<212> TYPE: RNA
<213> ORGANISM: Artificial
<220> FEATURE:
<223> OTHER INFORMATION: Terminating oligonucleotide for the 5'
      untranslated region of HCV
<220> FEATURE:
<221> NAME/KEY: misc_feature
<222> LOCATION: (1)..(24)
<223> OTHER INFORMATION: 2'-O-methylribonucleotides

<400> SEQUENCE: 42
agacgcuuuc ugcgugaaga cagu                                          24

<210> SEQ ID NO 43
<211> LENGTH: 24
<212> TYPE: RNA
<213> ORGANISM: Artificial
<220> FEATURE:
<223> OTHER INFORMATION: Terminating oligonucleotide for the 5'
      untranslated region of HCV
<220> FEATURE:
<221> NAME/KEY: misc_feature
<222> LOCATION: (1)..(24)
<223> OTHER INFORMATION: 2'-O-methylribonucleotides

<400> SEQUENCE: 43
cuagacgcuu ucugcgugaa gaca                                          24

<210> SEQ ID NO 44
<211> LENGTH: 20
<212> TYPE: RNA
<213> ORGANISM: Artificial
<220> FEATURE:
<223> OTHER INFORMATION: Terminating oligonucleotide for 16S rRNA of
      Mycobacterium tuberculosis
<220> FEATURE:
<221> NAME/KEY: misc_feature
<222> LOCATION: (1)..(20)
<223> OTHER INFORMATION: 2'-O-methylribonucleotides

<400> SEQUENCE: 44
caguuuccca ggcuuauccc                                               20

<210> SEQ ID NO 45
<211> LENGTH: 24
<212> TYPE: DNA
<213> ORGANISM: Artificial
<220> FEATURE:
<223> OTHER INFORMATION: Digestion oligonucleotide for 16S rRNA of
      Mycobacterium tuberculosis

<400> SEQUENCE: 45
gtattagacc cagtttccca ggct                                          24

<210> SEQ ID NO 46
<211> LENGTH: 5
<212> TYPE: DNA
<213> ORGANISM: Artificial
```

```
<220> FEATURE:
<223> OTHER INFORMATION: Cap for priming oligonucleotide for 16S rRNA of
      Mycobacterium tuberculosis

<400> SEQUENCE: 46 ctatc                                                                     5

<210> SEQ ID NO 47
<211> LENGTH: 35
<212> TYPE: DNA
<213> ORGANISM: Artificial
<220> FEATURE:
<223> OTHER INFORMATION: Looped priming oligonucleotide for 16S rRNA of
      Mycobacterium tuberculosis
<220> FEATURE:
<221> NAME/KEY: misc_feature
<222> LOCATION: (7)..(8)
<223> OTHER INFORMATION: Abasic nucleotides

<400> SEQUENCE: 47
ctatttnngc cgtcacccca ccaacaagct gatag                                   35

<210> SEQ ID NO 48
<211> LENGTH: 37
<212> TYPE: DNA
<213> ORGANISM: Artificial
<220> FEATURE:
<223> OTHER INFORMATION: Looped priming oligonucleotide for 16S rRNA of
      Mycobacterium tuberculosis
<220> FEATURE:
<221> NAME/KEY: misc_feature
<222> LOCATION: (6)..(10)
<223> OTHER INFORMATION: Abasic nucleotides

<400> SEQUENCE: 48
ctatcnnnnn gccgtcaccc caccaacaag ctgatag                                 37

<210> SEQ ID NO 49
<211> LENGTH: 36
<212> TYPE: DNA
<213> ORGANISM: Artificial
<220> FEATURE:
<223> OTHER INFORMATION: Looped priming oligonucleotide for 16S rRNA of
      Mycobacterium tuberculosis
<220> FEATURE:
<221> NAME/KEY: misc_feature
<222> LOCATION: (5)..(9)
<223> OTHER INFORMATION: Abasic nucleotides

<400> SEQUENCE: 49
ctatnnnnng ccgtcacccc accaacaagc tgatag                                  36

<210> SEQ ID NO 50
<211> LENGTH: 38
<212> TYPE: DNA
<213> ORGANISM: Artificial
<220> FEATURE:
<223> OTHER INFORMATION: Looped priming oligonucleotide for 16S rRNA of
      Mycobacterium tuberculosis
<220> FEATURE:
<221> NAME/KEY: misc_feature
<222> LOCATION: (7)..(11)
<223> OTHER INFORMATION: Abasic nucleotides

<400> SEQUENCE: 50
ctatcannnn ngccgtcacc ccaccaacaa gctgatag                                38

<210> SEQ ID NO 51
<211> LENGTH: 36
<212> TYPE: DNA
```

<213> ORGANISM: Artificial
<220> FEATURE:
<223> OTHER INFORMATION: Looped priming oligonucleotide for 16S rRNA of
       Mycobacterium tuberculosis
<220> FEATURE:
<221> NAME/KEY: misc_feature
<222> LOCATION: (6)..(9)
<223> OTHER INFORMATION: Abasic nucleotides

<400> SEQUENCE: 51
ctatcnnnng ccgtcacccc accaacaagc tgatag                                36

<210> SEQ ID NO 52
<211> LENGTH: 37
<212> TYPE: DNA
<213> ORGANISM: Artificial
<220> FEATURE:
<223> OTHER INFORMATION: Looped priming oligonucleotide for 16S rRNA of
       Mycobacterium tuberculosis
<220> FEATURE:
<221> NAME/KEY: misc_feature
<222> LOCATION: (7)..(10)
<223> OTHER INFORMATION: Abasic nucleotides

<400> SEQUENCE: 52
ctatcannnn gccgtcaccc caccaacaag ctgatag                               37

<210> SEQ ID NO 53
<211> LENGTH: 47
<212> TYPE: DNA
<213> ORGANISM: Artificial
<220> FEATURE:
<223> OTHER INFORMATION: Looped priming oligonucleotide for 16S rRNA of
       Mycobacterium tuberculosis
<220> FEATURE:
<221> NAME/KEY: misc_feature
<222> LOCATION: (16)..(20)
<223> OTHER INFORMATION: Abasic nucleotides

<400> SEQUENCE: 53
ctatcagctt gttggnnnnn gccgtcaccc caccaacaag ctgatag                    47

<210> SEQ ID NO 54
<211> LENGTH: 14
<212> TYPE: DNA
<213> ORGANISM: Artificial
<220> FEATURE:
<223> OTHER INFORMATION: Cap for priming oligonucleotide for 16S rRNA of
       Mycobacterium tuberculosis

<400> SEQUENCE: 54
ctatcagctt gttg                                                        14

<210> SEQ ID NO 55
<211> LENGTH: 32
<212> TYPE: DNA
<213> ORGANISM: Artificial
<220> FEATURE:
<223> OTHER INFORMATION: Extender oligonucleotide for 5' untranslated
       region of HCV

<400> SEQUENCE: 55
cctccaggac cccccctccc gggagagcca ta                                    32

<210> SEQ ID NO 56
<211> LENGTH: 26
<212> TYPE: RNA
<213> ORGANISM: Artificial
<220> FEATURE:
<223> OTHER INFORMATION: Terminating oligonucleotide for 5' untranslated region of HCV

<400> SEQUENCE: 56
auggcuagac gcuuucugcg ugaaga                                      26

<210> SEQ ID NO 57
<211> LENGTH: 26
<212> TYPE: DNA
<213> ORGANISM: Artificial
<220> FEATURE:
<223> OTHER INFORMATION: Displacer oligonucleotide for orfX gene of
      Staphylococcus aureus
<220> FEATURE:
<221> NAME/KEY: misc_feature
<222> LOCATION: (1)..(3)
<223> OTHER INFORMATION: Locked nucleic acids

<400> SEQUENCE: 57
cuugctcaat taacacaacc cgcatc                                      26

<210> SEQ ID NO 58
<211> LENGTH: 15
<212> TYPE: DNA
<213> ORGANISM: Artificial
<220> FEATURE:
<223> OTHER INFORMATION: Terminating oligonucleotide for orfX gene of
      Staphylococcus aureus
<220> FEATURE:
<221> NAME/KEY: misc_feature
<222> LOCATION: (1)..(3)
<223> OTHER INFORMATION: Locked nucleic acids
<220> FEATURE:
<221> NAME/KEY: misc_feature
<222> LOCATION: (7)..(9)
<223> OTHER INFORMATION: Locked nucleic acids
<220> FEATURE:
<221> NAME/KEY: misc_feature
<222> LOCATION: (13)..(15)
<223> OTHER INFORMATION: Locked nucleic acids

<400> SEQUENCE: 58
ggtcatgcgt tgguu                                                  15

<210> SEQ ID NO 59
<211> LENGTH: 22
<212> TYPE: RNA
<213> ORGANISM: Artificial
<220> FEATURE:
<223> OTHER INFORMATION: Detection probe for orfX gene of Staphylococcus
      aureus
<220> FEATURE:
<221> NAME/KEY: misc_feature
<222> LOCATION: (1)..(22)
<223> OTHER INFORMATION: 2'-O-methylribonucleotides
<220> FEATURE:
<221> NAME/KEY: misc_feature
<222> LOCATION: (17)..(18)
<223> OTHER INFORMATION: Nine carbon linker positioned between the
      nucleotides 17 and 18

<400> SEQUENCE: 59
ccgucauugg cggaucagac gg                                          22

KITS FOR AMPLIFYING DNA

CROSS-REFERENCE TO RELATED APPLICATIONS

This application is a divisional of U.S. application Ser. No. 11/681,104, filed Mar. 1, 2007, now U.S. Pat. No. 7,713,697, the contents of which are hereby incorporated by reference herein.

FIELD OF THE INVENTION

This invention relates to methods, reaction mixtures, compositions and kits for producing multiple copies of a specific nucleic acid sequence or "target sequence" which may be present either alone or as a component, large or small, of a homogeneous or heterogeneous mixture of nucleic acids. The mixture of nucleic acids may be that found in a sample taken for diagnostic testing, for screening of blood products, for food, water, industrial or environmental testing, for research studies, for the preparation of reagents or materials for other processes such as cloning, or for other purposes.

The selective amplification of specific nucleic acid sequences is of value in increasing the sensitivity of diagnostic and other detection assays while maintaining specificity; increasing the sensitivity, convenience, accuracy and reliability of a variety of research procedures; and providing ample supplies of specific oligonucleotides for various purposes.

BACKGROUND OF THE INVENTION

The detection and/or quantitation of specific nucleic acid sequences is an important technique for identifying and classifying microorganisms, diagnosing infectious diseases, detecting and characterizing genetic abnormalities, identifying genetic changes associated with cancer, studying genetic susceptibility to disease, and measuring response to various types of treatment. Such procedures are also useful in detecting and quantitating microorganisms in foodstuffs, water, industrial and environmental samples, seed stocks, and other types of material where the presence of specific microorganisms may need to be monitored. Other applications are found in the forensic sciences, anthropology, archaeology, and biology where measurement of the relatedness of nucleic acid sequences has been used to identify criminal suspects, resolve paternity disputes, construct genealogical and phylogenetic trees, and aid in classifying a variety of life forms.

A number of methods to detect and/or quantitate nucleic acid sequences are well known in the art. These include hybridization to a labeled probe, and various permutations of the polymerase chain reaction (PCR), coupled with hybridization to a labeled probe. See, e.g., Mullis et al., "Process for Amplifying, Detecting and/or Cloning Nucleic Acid Sequences," U.S. Pat. No. 4,683,195; Mullis, "Process for Amplifying Nucleic Acid Sequences," U.S. Pat. No. 4,683,202; Mullis et al., "Process for Amplifying, Detecting and/or Cloning Nucleic Acid Sequences," U.S. Pat. No. 4,800,159; Mullis et al. (1987) *Meth. Enzymol.* 155, 335-350; and Murakawa et al. (1988) *DNA* 7, 287-295. The requirement of repeated cycling of reaction temperature between several different and extreme temperatures is a disadvantage of the PCR procedure. In order to make PCR convenient, expensive programmable thermal cycling instruments are required.

Additionally, Transcription-Mediated Amplification (TMA) methods may be used to synthesize multiple copies of a target nucleic acid sequence autocatalytically under conditions of substantially constant temperature, ionic strength, and pH in which multiple RNA copies of the target sequence autocatalytically generate additional copies. See, e.g., Kacian et al., "Nucleic Acid Sequence Amplification Methods," U.S. Pat. No. 5,399,491, and Kacian et al, "Nucleic Acid Sequence Amplification Methods," U.S. Pat. No. 5,824,518, the contents of each of which patents are hereby incorporated by reference herein. TMA is useful for generating copies of a nucleic acid target sequence for purposes which include assays to quantitate specific nucleic acid sequences in clinical, environmental, forensic and similar samples, cloning and generating probes. TMA is a robust and highly sensitive amplification system with demonstrated efficacy. TMA overcomes many of the problems associated with PCR-based amplification systems. In particular, temperature cycling is not required. Other transcription-based amplification methods are disclosed by Malek et al., "Enhanced Nucleic Acid Amplification Process," U.S. Pat. No. 5,130,238; Davey et al., "Nucleic Acid Amplification Process," U.S. Pat. No. 5,409,818; Davey et al., "Method for the Synthesis of Ribonucleic Acid (RNA)," U.S. Pat. No. 5,466,586; Davey et al., "Nucleic Acid Amplification Process," U.S. Pat. No. 5,554,517; Burg et al., "Selective Amplification of Target Polynucleotide Sequences," U.S. Pat. No. 6,090,591; and Burg et al., "Selective Amplification of Target Polynucleotide Sequences," U.S. Pat. No. 6,410,276.

An inherent result of highly sensitive nucleic amplification systems is the emergence of side-products. Side-products include molecules which may, in some systems, interfere with the amplification reaction, thereby lowering specificity. This is because limited amplification resources, including primers and enzymes needed in the formation of primer extension and transcription products are diverted to the formation of side-products. In some situations, the appearance of side-products can also complicate the analysis of amplicon production by various molecular techniques.

Accordingly, there remains a need in the art for a robust nucleic acid amplification system to synthesize multiple copies of a target nucleic acid sequence autocatalytically under conditions of substantially constant temperature, ionic strength, and pH which reduces the appearance of side-products, thereby increasing specificity and improving detection and quantitation of amplification products.

SUMMARY OF THE INVENTION

The present invention is directed to novel methods of synthesizing multiple copies of a target sequence which are auto catalytic (i.e., able to cycle automatically without the need to modify reaction conditions such as temperature, pH, or ionic strength and using the product of one cycle in the next one). In particular, the present invention discloses methods of nucleic acid amplification which are robust and efficient, while reducing the appearance of side-products. The methods use a priming oligonucleotide, a promoter oligonucleotide modified to prevent the initiation of DNA synthesis therefrom (e.g., includes a 3'-blocking moiety) and, optionally, a displacer oligonucleotide, a binding molecule and/or a 3'-blocked extender oligonucleotide, to amplify RNA or DNA molecules in vitro. Primers used in the disclosed methods target only one sense of a target nucleic acid. The methods of the present invention minimize or substantially eliminate the emergence of side-products, thus providing a high level of specificity. Furthermore, the appearance of side-products can complicate the analysis of the amplification reaction by various molecular detection techniques. The present invention minimizes or substantially eliminates this problem, thus providing an enhanced level of sensitivity.

In one embodiment, the present invention is drawn to a method of synthesizing multiple copies of a target sequence comprising treating a target nucleic acid which comprises an RNA target sequence with a priming oligonucleotide and a binding molecule (e.g., terminating oligonucleotide or digestion oligonucleotide), where the priming oligonucleotide hybridizes to the 3'-end of the target sequence such that a primer extension reaction can be initiated therefrom, and where the binding molecule binds to the target nucleic acid adjacent to or near the 5'-end of the target sequence (by "adjacent to" is meant that the binding molecule binds to a base of the target nucleic acid next to the 5'-terminal base of the target sequence and fully 5' to the target sequence); extending the priming oligonucleotide in a primer extension reaction with a DNA polymerase, e.g., reverse transcriptase, to give a DNA primer extension product complementary to the target sequence, where the primer extension product has a 3'-end which is determined by the binding molecule, where the 3'-end of the primer extension product is complementary to the 5'-end of the target sequence; separating the primer extension product from the target sequence using an enzyme which selectively degrades the target sequence, e.g., an enzyme with an RNAse H activity; treating the primer extension product with a promoter oligonucleotide comprising first and second regions, where the first region hybridizes to a 3'-region of the primer extension product to form a promoter oligonucleotide:primer extension product hybrid, where the second region comprises a promoter for an RNA polymerase and is situated 5' to the first region, and where the promoter oligonucleotide is modified to prevent the initiation of DNA synthesis therefrom (e.g., a blocking moiety is situated at the 3'-terminus of the promoter oligonucleotide which prevents polymerase extension); extending the 3'-end of the primer extension product in the promoter oligonucleotide:primer extension product hybrid to add a sequence complementary to the second region of the promoter oligonucleotide; and transcribing from the promoter oligonucleotide:primer extension product hybrid multiple RNA products complementary to the primer extension product using an RNA polymerase which recognizes the promoter in the promoter oligonucleotide and initiates transcription therefrom. According to this embodiment, the base sequences of the resulting RNA products are substantially identical to the base sequence of the target sequence. In a preferred aspect of this embodiment, the activity of the DNA polymerase is substantially limited to the formation of primer extension products comprising the priming oligonucleotide. In yet another preferred aspect of this embodiment, the formation of side-products in the method is substantially less than if said promoter oligonucleotide was not modified to prevent the initiation of DNA synthesis therefrom. According to yet another preferred aspect of this embodiment, if an oligonucleotide used in the amplification reaction comprises a promoter for an RNA polymerase, then that oligonucleotide further comprises a blocking moiety situated at its 3'-terminus to prevent the initiation of DNA synthesis therefrom.

A second embodiment of the present invention is drawn to a method of synthesizing multiple copies of a target sequence, where the method comprises treating a target nucleic acid comprising an RNA target sequence with a priming oligonucleotide which hybridizes to the 3'-end of the target sequence such that a primer extension reaction can be initiated therefrom; extending the priming oligonucleotide in a primer extension reaction with a DNA polymerase, e.g., reverse transcriptase, to give a first DNA primer extension product having an indeterminate 3'-end and comprising a base region complementary to the target sequence; separating the first primer extension product from the target nucleic acid using an enzyme which selectively degrades that portion of the target nucleic acid which is complementary to the first primer extension reaction, e.g., an enzyme with an RNAse H activity; treating the first primer extension product with a promoter oligonucleotide comprising first and second regions, where the first region hybridizes to a 3'-region of the first primer extension product to form a promoter oligonucleotide:first primer extension product hybrid, where the second region comprises a promoter for an RNA polymerase and is situated 5' to the first region, and where the promoter oligonucleotide is modified to prevent the initiation of DNA synthesis therefrom (e.g., a blocking moiety is situated at the 3'-terminus of the promoter oligonucleotide which prevents polymerase extension); and transcribing from the promoter oligonucleotide:first primer extension product hybrid multiple first RNA products complementary to at least a portion of the first primer extension product using an RNA polymerase which recognizes the promoter and initiates transcription therefrom, where the base sequences of the resulting first RNA products are substantially identical to the base sequence of the target sequence. In a preferred aspect of this embodiment, the activity of the DNA polymerase in the method is substantially limited to the formation of primer extension products comprising the priming oligonucleotide. In yet another preferred aspect of this embodiment, the formation of side-products in the method is substantially less than if the promoter oligonucleotide was not modified to prevent the initiation of DNA synthesis therefrom. According to yet another preferred aspect of this embodiment, if an oligonucleotide used in the amplification reaction comprises a promoter for an RNA polymerase, then that oligonucleotide further comprises a blocking moiety situated at its 3'-terminus to prevent the initiation of DNA synthesis therefrom.

This embodiment is preferably drawn to the further steps of treating a first RNA product transcribed from the promoter oligonucleotide:first primer extension product with the priming oligonucleotide described above to form a priming oligonucleotide:first RNA product hybrid such that a primer extension reaction can be initiated from the priming oligonucleotide; extending the priming oligonucleotide in a primer extension reaction with a DNA polymerase, e.g., reverse transcriptase, to give a second DNA primer extension product complementary to the first RNA product, where the second primer extension product has a 3'-end which is complementary to the 5'-end of the first RNA product; separating the second primer extension product from the first RNA product using an enzyme which selectively degrades the first RNA product, e.g., an enzyme with an RNAse H activity; treating the second primer extension product with the promoter oligonucleotide described above to form a promoter oligonucleotide:second primer extension product hybrid; extending the 3'-end of the second primer extension product in the promoter oligonucleotide:second primer extension product hybrid to add a sequence complementary to the second region of the promoter oligonucleotide; and transcribing from the promoter oligonucleotide:second primer extension product hybrid multiple second RNA products complementary to the second primer extension product using an RNA polymerase, where the base sequences of the second RNA products are substantially identical to the base sequence of the target sequence.

A third embodiment of the present invention is drawn to a method of synthesizing multiple copies of a target sequence comprising treating a target nucleic acid comprising a DNA target sequence with a promoter oligonucleotide comprising first and second regions, where the first region hybridizes to the 3'-end of the target sequence to form a promoter oligonucleotide:target nucleic acid hybrid, where the second region comprises a promoter for an RNA polymerase and is situated 5' to the first region, and where the promoter oligonucleotide is modified to prevent the initiation of DNA synthesis therefrom (e.g., a blocking moiety is situated at the 3'-terminus of the promoter oligonucleotide); transcribing from the promoter oligonucleotide:target nucleic acid hybrid multiple first RNA products comprising a base region complementary to the target sequence using an RNA polymerase which recognizes the promoter and initiates transcription therefrom; treating the first RNA products with a priming oligonucleotide which hybridizes to a 3'-region of the first RNA products such that a primer extension reaction may be initiated therefrom; extending the priming oligonucleotide in the primer extension reaction with a DNA polymerase, e.g., reverse transcriptase, to give a DNA primer extension product complementary to at least a portion of the first RNA products, where the primer extension product has a 3'-end which is complementary to the 5'-end of the first RNA products; separating the primer extension product from the first RNA product using an enzyme which selectively degrades the first RNA product (e.g., an enzyme with an RNAse H activity); treating the primer extension product with the promoter oligonucleotide described above to form a promoter oligonucleotide:primer extension product hybrid; and transcribing from the promoter oligonucleotide:primer extension product hybrid multiple second RNA products complementary to the primer extension product using an RNA polymerase, wherein the base sequences of the second RNA products are substantially complementary to the base sequence of the target sequence. In a preferred aspect of this embodiment, the activity of the DNA polymerase in the method is substantially limited to the formation of primer extension products comprising the priming oligonucleotide. In yet another preferred aspect of this embodiment, the formation of side-products in the method is substantially less than if the promoter oligonucleotide was not modified to prevent the initiation of DNA synthesis therefrom. According to yet another preferred aspect of this embodiment, if an oligonucleotide used in the amplification reaction comprises a promoter for an RNA polymerase, then that oligonucleotide further comprises a blocking moiety situated at its 3'-terminus to prevent the initiation of DNA synthesis therefrom. Furthermore, any method of this embodiment may include extending the 3'-end of the primer extension product in the promoter oligonucleotide:primer extension product hybrid described above to add a sequence complementary to the second region of the promoter oligonucleotide.

A fourth embodiment of the present invention is drawn to a method of synthesizing multiple copies of a target sequence comprising treating a target nucleic acid which comprises a DNA target sequence with a priming oligonucleotide, where the priming oligonucleotide hybridizes to the 3'-end of the target sequence such that a primer extension reaction can be initiated therefrom; extending the priming oligonucleotide in a primer extension reaction with a DNA polymerase, e.g., reverse transcriptase, to give a first DNA primer extension product, where at least a portion of the first primer extension product is complementary to the target sequence; treating the primer extension product with a promoter oligonucleotide comprising first and second regions, where the first region comprises a base sequence which corresponds to a region at the 5'-end of the target sequence and which hybridizes to the first primer extension product to form a promoter oligonucleotide:first primer extension product hybrid, where the second region comprises a promoter for an RNA polymerase and is situated 5' to the first region, and where the promoter oligonucleotide is modified to prevent the initiation of DNA synthesis therefrom (e.g., a blocking moiety is situated at the 3'-terminus of the promoter oligonucleotide which prevents polymerase extension); and transcribing from the promoter oligonucleotide:first primer extension product hybrid multiple first RNA products complementary to at least a portion of the first primer extension product using an RNA polymerase which recognizes the promoter in the promoter oligonucleotide and initiates transcription therefrom. Provided that if the first primer extension product has a defined 3'-end, then the method further comprises treating the target nucleic acid with a binding molecule which binds to the target nucleic acid adjacent to or near the 5'-end of the target sequence. Further provided that the priming oligonucleotide does not include an RNA region which hybridizes to the target nucleic acid and which is selectively degraded by an enzyme activity when hybridized to the target nucleic acid. According to this embodiment, the base sequences of the resulting first RNA products are substantially identical to the base sequence of the target sequence. In a preferred aspect of this embodiment, the target nucleic acid is part of a double-stranded complex that is exposed to conditions sufficient to denature the complex (e.g., heat and/or chemical denaturants) prior to extending the priming oligonucleotide in a primer extension reaction. In another preferred aspect of this embodiment, the activity of the DNA polymerase is substantially limited to the formation of primer extension products comprising the priming oligonucleotide. In yet another preferred aspect of this embodiment, the formation of side-products in the method is substantially less than if said promoter oligonucleotide was not modified to prevent the initiation of DNA synthesis therefrom. In yet a further preferred aspect of this embodiment, if an oligonucleotide used in the amplification reaction comprises a promoter for an RNA polymerase, then that oligonucleotide further comprises a blocking moiety situated at its 3'-terminus to prevent the initiation of DNA synthesis therefrom.

The method of this embodiment is preferably drawn to the further steps of treating the first RNA products transcribed from the promoter oligonucleotide:first DNA primer extension product with the priming oligonucleotide described above to form a priming oligonucleotide:first RNA product hybrid such that a primer extension reaction can be initiated from the priming oligonucleotide; extending the priming oligonucleotide in a primer extension reaction with a DNA polymerase, e.g., reverse transcriptase, to give a second DNA primer extension product complementary to the first RNA product, where the second primer extension product has a 3'-end which is complementary to the 5'-end of the first RNA product; separating the second primer extension product from the first RNA product using an enzyme which selectively degrades the first RNA product, e.g., an enzyme with an RNAse H activity; treating the second primer extension product with the promoter oligonucleotide described above to form a promoter oligonucleotide:second primer extension product hybrid; extending the 3'-end of the second primer extension product in the promoter oligonucleotide:second primer extension product hybrid to add a sequence complementary to the second region of the promoter oligonucleotide; and transcribing from the promoter oligonucleotide:second primer extension product hybrid multiple second RNA products complementary to the second primer extension product using an RNA polymerase, where the base sequences of the second RNA products are substantially identical to the base sequence of the target sequence.

Another aspect of the method of this embodiment comprises treating the target nucleic acid with a binding molecule (e.g., terminating oligonucleotide or digestion oligonucleotide), where the binding molecule binds to the target nucleic acid adjacent to or near the 5'-end of the target sequence (as indicated above, the phrase "adjacent to" means that the binding molecule binds to a base sequence of the target nucleic acid next to the 5'-terminal base of the target sequence and fully 5' to the target sequence). The target nucleic acid is preferably treated with the binding molecule prior to initiating extension of the priming oligonucleotide in a primer extension reaction with a DNA polymerase. In this aspect, the first primer extension product has a 3'-end which is determined by the binding molecule, where the 3'-end of the primer extension product is complementary to the 5'-end of the target sequence. After the promoter oligonucleotides hybridizes to the first primer extension product, this aspect of the method further comprises extending the 3'-end of the first DNA primer extension product in the promoter oligonucleotide:first primer extension product hybrid to add a sequence complementary to the second region of the promoter oligonucleotide.

Yet another aspect of the method of this embodiment comprises treating the target nucleic acid with a displacer oligonucleotide, where the displacer oligonucleotide hybridizes to the target nucleic acid upstream from the priming oligonucleotide such that a primer extension reaction can be initiated therefrom (in this context, the term "upstream" means that the 3'-terminal nucleotide of the displacer oligonucleotide is 5' to the 3'-terminal nucleotide of the priming oligonucleotide), and then extending the displacer oligonucleotide in a primer extension reaction with a DNA polymerase to give a second DNA primer extension product that displaces the first DNA primer extension product from the target nucleic acid. In a preferred aspect, the activity of the DNA polymerase is substantially limited to the formation of primer extension products comprising the displacer and priming oligonucleotides.

Reagents and conditions suitable for practicing any of the embodiments described above are set forth in the Examples section.

The methods of the present invention may be used as a component of assays to detect and/or quantitate specific nucleic acid target sequences in clinical, food, water, industrial, environmental, forensic, and similar samples or to produce large numbers of copies of DNA and/or RNA of specific target sequences for a variety of uses. (As used herein, the term "copies" refers to amplification products having either the same or the opposite sense of the target sequence.) These methods may also be used to produce multiple copies of a target sequence for cloning or to generate probes or to produce RNA and DNA copies for sequencing.

The priming oligonucleotides of the embodiments described above optionally have a cap comprising a base region hybridized to a 3'-end thereof prior to treating a target nucleic acid or an RNA product with one of the priming oligonucleotides in order to prevent the initiation of DNA synthesis therefrom. (As used herein, the term "priming oligonucleotide" is inclusive of displacer oligonucleotides.) The 5'-terminal base (i.e., the 5'-most base) of a cap hybridizes to the 3'-terminal base (i.e., the 3'-most base) of a priming oligonucleotide. However, the caps are designed to be preferentially displaced from priming oligonucleotides by a target nucleic acid, a primer extension product, or an RNA product. A cap of the present invention may take the form of a discrete capping oligonucleotide, or may be attached to the 5'-end of a priming oligonucleotide via a linker. A preferred capping oligonucleotide is modified to prevent the initiation of DNA synthesis therefrom (e.g., comprises a blocking moiety at its 3'-terminus).

To increase the binding affinity of a priming oligonucleotide for a target nucleic acid or complement thereof, the 5'-end of a priming oligonucleotide may include one or more modifications which improve the binding properties (e.g., hybridization or base stacking) of the priming oligonucleotide to the target nucleic acid or an RNA product, provided the modifications do not prevent the priming oligonucleotide from being extended in a primer extension reaction or substantially interfere with cleavage of an RNA template to which the priming oligonucleotide is hybridized. The modifications are preferably spaced at least 15 bases from the 3'-terminus of a priming oligonucleotide, and most preferably affect a region limited to the three or four 5'-most nucleotides of the priming oligonucleotide. Preferred modifications include 2'-O-methyl ribonucleotides and "Locked Nucleic Acids" or "Locked Nucleoside Analogues" (LNAs). See Becker et al., "Method for Amplifying Target Nucleic Acids Using Modified Primers," U.S. Pat. No. 6,13,038; Imanishi et al., "Bicyclonucleoside and Oligonucleotide Analogues," U.S. Pat. No. 6,268,490; and Wengel et al., "Oligonucleotide Analogues," U.S. Pat. No. 6,670,461. The contents of each of the foregoing references are hereby incorporated by reference herein.

The promoter oligonucleotide used in the methods described above may further include an insertion sequence which is selected to enhance the rate at which RNA products are formed. The insertion sequence is preferably from 5 to 20 nucleotides in length and is positioned between or adjacent to the first and second regions of the promoter oligonucleotide. Preferred insertion sequences of the present invention include the base sequences of SEQ ID NO:1 ccacaa and SEQ ID NO:2 acgtagcatcc.

The rate of amplification may also be affected by the inclusion of an extender oligonucleotide in any of the above-described methods. An extender oligonucleotide is preferably from 10 to 50 nucleotides in length and is designed to hybridize to a DNA template so that the 5'-end of the extender oligonucleotide is adjacent to or near the 3'-end of a promoter oligonucleotide. The extender oligonucleotide is preferably modified to prevent the initiation of DNA synthesis therefrom (e.g., includes a 3'-terminal blocking moiety).

In some applications of the methods described above, the binding molecule may comprise an oligonucleotide having a 5'-end which overlaps the 5'-end of the first region of the promoter oligonucleotide. To limit hybridization of the binding molecule to the promoter oligonucleotide, the 5'-end of the first region of the promoter oligonucleotide may be synthesized to include a sufficient number of mismatches with the 5'-end of the binding molecule to prevent the promoter oligonucleotide from hybridizing to the binding molecule. While a single mismatch generally should be sufficient, the number of destabilizing mismatches needed in the first region of the promoter oligonucleotide will depend upon the length and base composition of the overlapping region.

In an adaptation of the above methods, the blocking moiety may be released from the promoter oligonucleotide prior to treating the primer extension product or the first primer extension product with the promoter oligonucleotide. To facilitate release of the blocking moiety, the promoter oligonucleotide is provided to a reaction mixture pre-hybridized to an oligodeoxynucleotide. The oligodeoxynucleotide is hybridized to a 3'-region of the first region of the promoter oligonucleotide which includes a sufficient number of contiguous ribonucleotides such that the blocking moiety is released from the promoter oligonucleotide in the presence of an enzymatic activity capable of cleaving the ribonucleotides of the 3'-region. During cleavage of the ribonucleotides, the oligodeoxynucleotide is also released from the first region of the promoter oligonucleotide, and the remaining, uncleaved portion of the first region hybridizes to the primer extension product or the first primer extension product. The 3'-section of ribonucleotides preferably includes at least 6 contiguous ribonucleotides, and the oligdeoxyonucleotide is preferably the same length as and fully complementary to the 3'-section of ribonucleotides. The oligodeoxynucleotide may be a separate molecule or it may be joined to the promoter oligonucleotide by means of a linker.

The present invention further relates to reaction mixtures useful for carrying out the methods described above. The reaction mixtures of the present invention may contain each component, or some subcombination of components, necessary for carrying out the methods described above.

The materials and/or reagents used in the methods of the present invention may be incorporated as parts of kits, e.g., diagnostic kits for clinical or criminal laboratories, or nucleic amplification kits for general laboratory use. The present invention thus includes kits which include some or all of the components necessary to carry out the methods of the present invention, e.g., oligonucleotides, binding molecules, stock solutions, enzymes, positive and negative control target sequences, detection reagents, containers (e.g., test tubes, cuvettes, cassettes, plates, microfluidic devices and the like), and instructions provided in written or electronic form for performing the disclosed methods.

Certain embodiments of the present invention include one or more detection probes for determining the presence or amount of the RNA and/or DNA products in the amplification reaction mixture. Probes may be designed to detect RNA and/or DNA products after the amplification reaction (i.e., end-point detection) or, alternatively, during the amplification reaction (i.e., real-time detection involves periodically measuring the amount of signal associated with probe:amplicon complexes in the reaction mixture). Thus, the probes may be provided to the reaction mixture prior to, during or at the completion of the amplification reaction. For real-time detection of RNA products in the first two methods described above, it may be desirable to provide the probe to the reaction mixture after the first primer extension reaction has been initiated (i.e., addition of amplification enzymes) since probe binding to the target sequence, rather than RNA product, may slow the rate at which an RNA-dependent DNA polymerase (e.g., reverse transcriptase) can extend the priming oligonucleotide. Preferred probes have one or more associated labels to facilitate detection.

The present invention is further drawn to various oligonucleotides, including the priming oligonucleotides, promoter oligonucleotides, terminating oligonucleotides, displacer oligonucleotides, capping oligonucleotides, extender oligonucleotides and detection probes described herein. It is to be understood that oligonucleotides of the present invention may be DNA or RNA (and analogs thereof), and in either case, the present invention includes RNA equivalents of DNA oligonucleotides and DNA equivalents of RNA oligonucleotides. Except for the preferred priming oligonucleotides, displacer oligonucleotides and detection probes described below, the oligonucleotides described in the following paragraphs are preferably modified to prevent their participation in a synthesis reaction in the presence of a DNA polymerase (e.g., include a blocking moiety at their 3'-termini).

For certain amplification reactions in which the target nucleic acid contains a hepatitis C virus (HCV) 5' untranslated region, the present invention includes a promoter oligonucleotide comprising a promoter sequence and a hybridizing sequence up to 40 or 50 bases in length. The promoter sequence is recognized by an RNA polymerase, such as a T7, T3 or SP6 RNA polymerase, and preferably includes the T7 RNA polymerase promoter sequence of SEQ ID NO:3 aatttaatacgactcac tagggaga. The hybridizing sequence of the preferred promoter oligonucleotide comprises, consists of, consists essentially of, overlaps with, or is contained within and includes at least 10, 15, 20, 25, 30 or 32 contiguous bases of a base sequence that is at least 80%, 90% or 100% identical to the base sequence of SEQ ID NO:4 ctagccatggcgttagtatgagtgtcgtgcag or an equivalent sequence containing uracil bases substituted for thymine bases, and which hybridizes to the target nucleic acid under amplification conditions. The promoter oligonucleotide preferably does not include a region in addition to the hybridizing sequence that hybridizes to the target nucleic acid under amplification conditions. More preferably, the promoter oligonucleotide comprises, consists of, or consists essentially of a base sequence substantially corresponding to the base sequence of SEQ ID NO:5 aatttaatacgactcactatagggagactagccatggcgttagtatgagtgtcgtgcag or an equivalent sequence containing uracil bases substituted for thymine bases, and which hybridizes to the target nucleic acid under amplification conditions. The base sequence of the promoter oligonucleotide preferably consists of a promoter sequence and a hybridizing sequence consisting of or contained within and including at least 10, 15, 20, 25, 30 or 32 contiguous bases of the base sequence of SEQ ID NO:4 or an equivalent sequence containing uracil bases substituted for thymine bases, and which hybridizes to the target nucleic acid under amplification conditions.

For certain amplification reactions in which the target nucleic acid contains an HCV 5' untranslated region, the present invention includes a priming oligonucleotide up to 40 or 50 bases in length. A preferred priming oligonucleotide includes an oligonucleotide comprising, consisting of, consisting essentially of, overlapping with, or contained within and including at least 10, 15, 20, 25, 30 or 31 contiguous bases of a base sequence that is at least 80%, 90% or 100% identical to the base sequence of SEQ ID NO:6 aggcattgagcgggttgatccaagaaaggac or an equivalent sequence containing uracil bases substituted for thymine bases, and which hybridizes to the target nucleic acid under amplification conditions. More preferably, the priming oligonucleotide comprises, consists of, or consists essentially of a base sequence substantially corresponding to the base sequence of SEQ ID NO:6 or an equivalent sequence containing uracil bases substituted for thymine bases, and which hybridizes under amplification conditions to the target nucleic acid. The base sequence of the priming oligonucleotide preferably consists of or is contained within and includes at least 10, 15, 20, 25, 30 or 31 contiguous bases of the base sequence of SEQ ID NO:6 or an equivalent sequence containing uracil bases substituted for thymine bases, and which hybridizes to the target nucleic acid under amplification conditions.

For certain amplification reactions in which the target nucleic acid contains an HCV 5' untranslated region, the present invention is further directed to a detection probe up to 35, 50 or 100 bases in length. A preferred detection probe includes a target binding region which comprises, consists of, consists essentially of, overlaps with, or is contained within and includes at least 10, 13 or 15 contiguous bases of a base sequence that is at least 80%, 90% or 100% identical to the base sequence of SEQ ID NO:7 guacucaccgguucc, the complement thereof, or an equivalent sequence containing thymine bases substituted for uracil bases, and which preferentially hybridizes to the target nucleic acid or its complement (e.g., not human nucleic acid) under stringent hybridization conditions. The detection probe preferably does not include a region in addition to the target binding region that hybridizes to the target nucleic acid or its complement under stringent hybridization conditions. More preferably, the detection probe comprises, consists of, or consists essentially of a base sequence substantially corresponding to the base sequence of SEQ ID NO:7, the complement thereof, or an equivalent sequence containing thymine bases substituted for uracil bases, and which preferentially hybridizes to the target nucleic acid or its complement under stringent hybridization conditions. The base sequence of the detection probe preferably consists of or is contained within and includes at least 10, 13 or 15 contiguous bases of the base sequence of SEQ ID NO:7, the complement thereof, or an equivalent sequence containing thymine bases substituted for uracil bases, and which preferentially hybridizes to the target nucleic acid or its complement under stringent hybridization conditions. In certain embodiments the probe optionally includes one or more detectable labels, e.g., an AE substituent.

For certain amplification reactions in which the target nucleic acid contains an HCV 5' untranslated region, the present invention is further directed to a detection probe up to 40 or 50 bases in length. A preferred detection probe includes a target binding region which comprises, consists of, consists essentially of, overlaps with, or is contained within and includes at least 18, 20 or 22 contiguous bases of a base sequence that is at least 80%, 90% or 100% identical to the base sequence of SEQ ID NO:8 agaccacuauggcucucccggg, the complement thereof, or an equivalent sequence containing thymine bases substituted for uracil bases, and which preferentially hybridizes to the target nucleic acid or its complement (e.g., not human nucleic acid) under stringent hybridization conditions. The detection probe preferably does not include a region in addition to the target binding region that hybridizes to the target nucleic acid or its complement under stringent hybridization conditions. More preferably, the detection probe comprises, consists of, or consists essentially of a base sequence substantially corresponding to the base sequence of SEQ ID NO:8, the complement thereof, or an equivalent sequence containing thymine bases substituted for uracil bases, and which preferentially hybridizes to the target nucleic acid or its complement under stringent hybridization conditions. The base sequence of the detection probe preferably consists of or is contained within and includes at least 18, 20 or 22 contiguous bases of the base sequence SEQ ID NO:8, the complement thereof, or an equivalent sequence containing thymine bases substituted for uracil bases, and which preferentially hybridizes to the target nucleic acid or its complement under stringent hybridization conditions. In certain embodiments the probe optionally includes one or more detectable labels, e.g., an AE substituent.

For certain amplification reactions in which the target nucleic acid contains a human immunodeficiency virus (HIV) pol gene, the present invention includes a promoter oligonucleotide comprising a promoter sequence and a hybridizing sequence up to 40 or 50 bases in length. The promoter sequence is recognized by an RNA polymerase, such as a T7, T3 or SP6 RNA polymerase, and preferably includes the T7 RNA polymerase promoter sequence of SEQ ID NO:3. The hybridizing sequence of the preferred promoter oligonucleotide comprises, consists of, consists essentially of, overlaps with, or is contained within and includes at least 10, 15, 20, 25, 30 or 31 contiguous bases of a base sequence that is at least 80%, 90% or 100% identical to the base sequence of SEQ ID NO:9 acaaatggcagtattcatccacaatttaaaa or an equivalent sequence containing uracil bases substituted for thymine bases, and which hybridizes to the target nucleic acid under amplification conditions. The promoter oligonucleotide preferably does not include a region in addition to the hybridizing sequence that hybridizes to the target nucleic acid under amplification conditions. More preferably, the promoter oligonucleotide comprises, consists of, or consists essentially of a base sequence substantially corresponding to the base sequence of SEQ ID NO:10 aatttaatacgactcactatagggagacta gccatggcgttagtatgagtgtcgtgcag or an equivalent sequence containing uracil bases substituted for thymine bases, and which hybridizes to the target nucleic acid under amplification conditions. The base sequence of the promoter oligonucleotide preferably consists of a promoter sequence and a hybridizing sequence consisting of or contained within and including at least 10, 15, 20, 25, 30 or 31 contiguous bases of the base sequence of SEQ ID NO:9 or an equivalent sequence containing uracil bases substituted for thymine bases, and which hybridizes to the target nucleic acid under amplification conditions.

For certain amplification reactions in which the target nucleic acid contains an HIV pol gene, the present invention includes a priming oligonucleotide up to 40 or 50 bases in length. A preferred priming oligonucleotide includes an oligonucleotide comprising, consisting of, consisting essentially of, overlapping with, or contained within and including at least 10, 15, 20, 25 or 27 contiguous bases of a base sequence that is at least 80%, 90% or 100% identical to the base sequence of SEQ ID NO:11 gtttgtatgtctgttgctattatgtct or an equivalent sequence containing uracil bases substituted for thymine bases, and which hybridizes to the target nucleic acid under amplification conditions. More preferably, the priming oligonucleotide comprises, consists of, or consists essentially of a base sequence substantially corresponding to the base sequence of SEQ ID NO:11 or an equivalent sequence containing uracil bases substituted for thymine bases, and which hybridizes to the target nucleic acid under amplification conditions. The base sequence of the priming oligonucleotide preferably consists of or is contained within and includes at least 10, 15, 20, 25 or 27 contiguous bases of the base sequence of SEQ ID NO:11 or an equivalent sequence containing uracil bases substituted for thymine bases, and which hybridizes to the target nucleic acid under amplification conditions.

For certain amplification reactions in which the target nucleic acid contains an HIV pol gene, the present invention is further directed to a detection probe up to 35, 50 or 100 bases in length. A preferred detection probe includes a target binding region which comprises, consists of, consists essentially of, overlaps with, or is contained within and includes at least 13, 15 or 17 contiguous bases of a base sequence that is at least 80%, 90% or 100% identical to the base sequence of SEQ ID NO:12 acuguacccccaaucc, the complement thereof, or an equivalent sequence containing thymine bases substituted for uracil bases, and which preferentially hybridizes to the target nucleic acid or its complement (e.g., not human nucleic acid) under stringent hybridization conditions. The detection probe preferably does not include a region in addition to the target binding region that hybridizes to the target nucleic acid or its complement under stringent hybridization conditions. More preferably, the detection probe comprises, consists of, or consists essentially of a base sequence substantially corresponding to the base sequence of SEQ ID NO:12, the complement thereof, or an equivalent sequence containing thymine bases substituted for uracil bases, and which preferentially hybridizes to the target nucleic acid or its complement under stringent hybridization conditions. The base sequence of the detection probe preferably consists of or is contained within and includes at least 13, 15 or 17 contiguous bases of the base sequence of SEQ ID NO:12, the complement thereof, or an equivalent sequence containing thymine bases substituted for uracil bases, and which preferentially hybridizes under stringent hybridization conditions to the target nucleic acid or its complement. In certain embodiments the probe optionally includes one or more detectable labels, e.g., an AE substituent.

For certain amplification reactions in which the target nucleic acid contains a human papilloma virus (HPV) E6 and E7 gene, the present invention includes a promoter oligonucleotide comprising a promoter sequence and a hybridizing sequence up to 40 or 50 bases in length. The promoter sequence is recognized by an RNA polymerase, such as a T7, T3 or SP6 RNA polymerase, and preferably includes the T7 RNA polymerase promoter sequence of SEQ ID NO:3. The hybridizing sequence of the preferred promoter oligonucleotide comprises, consists of, consists essentially of, overlaps with, or is contained within and includes at least 10, 15, 20, 25 or 27 contiguous bases of a base sequence that is at least 80%, 90% or 100% identical to the base sequence of SEQ ID NO:13 gaacagatggggcacacaattcctagt or an equivalent sequence containing uracil bases substituted for thymine bases, and which hybridizes to the target nucleic acid under amplification conditions. The promoter oligonucleotide preferably does not include a region in addition to the hybridizing sequence that hybridizes to the target nucleic acid under amplification conditions. More preferably, the promoter oligonucleotide comprises, consists of, or consists essentially of a base sequence substantially corresponding to the base sequence of SEQ ID NO:14 aatttaatacgactcactatagggagagaa cagatggggcacacaattcctagt or an equivalent sequence containing uracil bases substituted for thymine bases, and which hybridizes to the target nucleic acid under amplification conditions. The base sequence of the promoter oligonucleotide preferably consists of a promoter sequence and a hybridizing sequence consisting of or contained within and including at least 10, 15, 20, 25 or 27 contiguous bases of the base sequence of SEQ ID NO:13 or an equivalent sequence containing uracil bases substituted for thymine bases, and which hybridizes to the target nucleic acid under amplification conditions.

For certain amplification reactions in which the target nucleic acid contains an HPV E6 and E7 gene, the present invention includes a priming oligonucleotide up to 40 or 50 bases in length. A preferred priming oligonucleotide includes an oligonucleotide comprising, consisting of, consisting essentially of, overlapping with, or contained within and including at least 10, 15 or 19 contiguous bases of a base sequence that is at least 80%, 90% or 100% identical to the base sequence of SEQ ID NO:15 gacagctcagaggaggagg or an equivalent sequence containing uracil bases substituted for thymine bases, and which hybridizes to the target nucleic acid under amplification conditions. More preferably, the priming oligonucleotide comprises, consists of, or consists essentially of a base sequence substantially corresponding to the base sequence of SEQ ID NO:15 or an equivalent sequence containing uracil bases substituted for thymine bases, and which hybridizes to the target nucleic acid under amplification conditions. The base sequence of the priming oligonucleotide preferably consists of or is contained within and includes at least 10, 15 or 19 contiguous bases of the base sequence of SEQ ID NO:15 or an equivalent sequence containing uracil bases substituted for thymine bases, and which hybridizes to the target nucleic acid under amplification conditions.

For certain amplification reactions in which the target nucleic acid contains an HPV E6 and E7 gene, the present invention is further directed to a detection probe up to 35, 50 or 100 bases in length. A preferred detection probe includes a target binding region which comprises, consists of, consists essentially of, overlaps with, or is contained within and includes at least 15, 17 or 19 contiguous bases of a base sequence that is at least 80%, 90% or 100% identical to the base sequence of SEQ ID NO:16 ggacaagcagaaccggaca or the complement thereof, and which preferentially hybridizes to the target nucleic acid or its complement (e.g., not human nucleic acid) under stringent hybridization conditions. The detection probe preferably does not include a region in addition to the target binding region that hybridizes to the target nucleic acid or its complement under stringent hybridization conditions. More preferably, the detection probe comprises, consists of, or consists essentially of a base sequence substantially corresponding to the base sequence of SEQ ID NO:16 or the complement thereof, and which preferentially hybridizes to the target nucleic acid or its complement under stringent hybridization conditions. The base sequence of the detection probe preferably consists of or is contained within and includes at least 15, 17 or 19 contiguous bases of the base sequence of SEQ ID NO:16 or the complement thereof, and which preferentially hybridizes to the target nucleic acid or its complement under stringent hybridization conditions. In certain embodiments the probe optionally includes one or more detectable labels, e.g., an AE substituent.

For certain amplification reactions in which the target nucleic acid contains a West Nile Virus (WNV) nonstructural protein 5 gene, the present invention includes a promoter oligonucleotide comprising a promoter sequence and a hybridizing sequence up to 40 or 50 bases in length. The promoter sequence is recognized by an RNA polymerase, such as a T7, T3 or SP6 RNA polymerase, and preferably includes the T7 RNA polymerase promoter sequence of SEQ ID NO:3. The hybridizing sequence of the preferred promoter oligonucleotide comprises, consists of, consists essentially of, overlaps with, or is contained within and includes at least 10, 15, 20, 25 or 27 contiguous bases of a base sequence that is at least 80%, 90% or 100% identical to the base sequence of SEQ ID NO:17 gagtagacggtgctgcctgcgactcaa or an equivalent sequence containing uracil bases substituted for thymine bases, and which hybridizes to the target nucleic acid under amplification conditions. The promoter oligonucleotide preferably does not include a region in addition to the hybridizing sequence that hybridizes to the target nucleic acid under amplification conditions. More preferably, the promoter oligonucleotide comprises, consists of, or consists essentially of a base sequence substantially corresponding to the base sequence of SEQ ID NO:18 aatttaatacgactcactcactatagg gagagagtagacggtgctgcctgcgactcaa or an equivalent sequence containing uracil bases substituted for thymine bases, and which hybridizes to the target nucleic acid under amplification conditions. The base sequence of the promoter oligonucleotide preferably consists of a promoter sequence and a hybridizing sequence consisting of or contained within and including at least 10, 15, 20, 25 or 27 contiguous bases of the base sequence of SEQ ID NO:17 or an equivalent sequence containing uracil bases substituted for thymine bases, and which hybridizes to the target nucleic acid under amplification conditions.

For certain amplification reactions in which the target nucleic acid contains a WNV nonstructural protein 5 gene, the present invention includes a priming oligonucleotide up to 40 or 50 bases in length. A preferred priming oligonucleotide includes an oligonucleotide comprising, consisting of, consisting essentially of, overlapping with, or contained within and including at least 10, 15, 20 or 23 contiguous bases of a base sequence that is at least 80%, 90% or 100% identical to the base sequence of SEQ ID NO:19 tccgagacggttctgagggctta or an equivalent sequence containing uracil bases substituted for thymine bases, and which hybridizes to the target nucleic acid under amplification conditions. More preferably, the priming oligonucleotide comprises, consists of, or consists essentially of a base sequence substantially corresponding to the base sequence of SEQ ID NO:19 or an equivalent sequence containing uracil bases substituted for thymine bases, and which hybridizes to the target nucleic acid under amplification conditions. The base sequence of the priming oligonucleotide preferably consists of or is contained within and includes at least 10, 15, 20 or 23 contiguous bases of the base sequence of SEQ ID NO:19 or an equivalent sequence containing uracil bases substituted for thymine bases, and which hybridizes to the target nucleic acid under amplification conditions.

For certain amplification reactions in which the target nucleic acid contains a WNV nonstructural protein 5 gene, the present invention is further directed to a detection probe up to 35, 50 or 100 bases in length. A preferred detection probe includes a target binding region which comprises, consists of, consists essentially of, overlaps with, or is contained within and includes at least 14, 16 or 18 contiguous bases of a base sequence that is at least 80%, 90% or 100% identical to the base sequence of SEQ ID NO:20 gaucacuucgcggcuuug, the complement thereof, or an equivalent sequence containing thymine bases substituted for uracil bases, and which preferentially hybridizes to the target nucleic acid or its complement (e.g., not human nucleic acid) under stringent hybridization conditions. The detection probe preferably does not include a region in addition to the target binding region that hybridizes to the target nucleic acid or its complement under stringent hybridization conditions. More preferably, the detection probe comprises, consists of, or consists essentially of a base sequence substantially corresponding to the base sequence of SEQ ID NO:20, the complement thereof, or an equivalent sequence containing thymine bases substituted for uracil bases, and which preferentially hybridizes to the target nucleic acid or its complement under stringent hybridization conditions. The base sequence of the detection probe preferably consists of or is contained within and includes at least 14, 16 or 18 contiguous bases of the base sequence of SEQ ID NO:20, the complement thereof, or an equivalent sequence containing thymine bases substituted for uracil bases, and which preferentially hybridizes to the target nucleic acid or its complement under stringent hybridization conditions. In certain embodiments the probe optionally includes one or more detectable labels, e.g., an AE substituent.

For certain amplification reactions in which the target nucleic acid contains a 23S rRNA sequence of *Chlamydia trachomatis*, the present invention includes a promoter oligonucleotide comprising a promoter sequence and a hybridizing sequence up to 40 or 50 bases in length. The promoter sequence is recognized by an RNA polymerase, such as a T7, T3 or SP6 RNA polymerase, and preferably includes the T7 RNA polymerase promoter sequence of SEQ ID NO:3. The hybridizing sequence of the preferred promoter oligonucleotide comprises, consists of, consists essentially of, overlaps with, or is contained within and includes at least 10, 15, 20, 25 or 30 contiguous bases of a base sequence that is at least 80%, 90% or 100% identical to the base sequence of SEQ ID NO:21 cggagtaagttaagcacgcggacgattgga or an equivalent sequence containing uracil bases substituted for thymine bases, and which hybridizes to the target nucleic acid under amplification conditions. The promoter oligonucleotide preferably does not include a region in addition to the hybridizing sequence that hybridizes to the target nucleic acid under amplification conditions. More preferably, the promoter oligonucleotide comprises, consists of, or consists essentially of a base sequence substantially corresponding to the base sequence of SEQ ID NO:22 aatttaatacgactcactatagggagacgg agtaagttaagcacgcggacgattgga or an equivalent sequence containing uracil bases substituted for thymine bases, and which hybridizes to the target nucleic acid under amplification conditions. The base sequence of the promoter oligonucleotide preferably consists of a promoter sequence and a hybridizing sequence consisting of or contained within and including at least 10, 15, 20, 25 or 30 contiguous bases of the base sequence of SEQ ID NO:21 or an equivalent sequence containing uracil bases substituted for thymine bases, and which hybridizes to the target nucleic acid under amplification conditions.

For certain amplification reactions in which the target nucleic acid contains a 23S rRNA sequence of *Chlamydia trachomatis*, the present invention includes a priming oligonucleotide up to 40 or 50 bases in length. A preferred priming oligonucleotide includes an oligonucleotide comprising, consisting of, consisting essentially of, overlapping with, or contained within and including at least 10, 15, 20, 25 or 29 contiguous bases of a base sequence that is at least 80%, 90% or 100% identical to the base sequence of SEQ ID NO:23 cccgaagattccccttgatcgcgacctga or an equivalent sequence containing uracil bases substituted for thymine bases, and which hybridizes to the target nucleic acid under amplification conditions. More preferably, the priming oligonucleotide comprises, consists of, or consists essentially of a base sequence substantially corresponding to the base sequence of SEQ ID NO:23 or an equivalent sequence containing uracil bases substituted for thymine bases, and which hybridizes to the target nucleic acid under amplification conditions. The base sequence of the priming oligonucleotide preferably consists of or is contained within and includes at least 10, 15, 20, 25 or 29 contiguous bases of the base sequence of SEQ ID NO:23 or an equivalent sequence containing uracil bases substituted for thymine bases, and which hybridizes to the target nucleic acid under amplification conditions.

For certain amplification reactions in which the target nucleic acid contains a 23S rRNA sequence of *Chlamydia trachomatis*, the present invention is further directed to a detection probe up to 35, 50 or 100 bases in length. A preferred detection probe includes a target binding region which comprises, consists of, consists essentially of, overlaps with, or is contained within and includes at least 19, 22 or 24 contiguous bases of a base sequence that is at least 80%, 90% or 100% identical to the base sequence of SEQ ID NO:24 cguucucaucgcucuacggacucu, the complement thereof, or an equivalent sequence containing thymine bases substituted for uracil bases, and which preferentially hybridizes to the target nucleic acid or its complement (e.g., not *Chlamydia psittaci* nucleic acid) under stringent hybridization conditions. The detection probe preferably does not include a region in addition to the target binding region that hybridizes to the target nucleic acid or its complement under stringent hybridization conditions. More preferably, the detection probe comprises, consists of, or consists essentially of a base sequence substantially corresponding to the base sequence of SEQ ID NO:24, the complement thereof, or an equivalent sequence containing thymine bases substituted for uracil bases, and which preferentially hybridizes under stringent hybridization conditions to the target nucleic acid or its complement. The base sequence of the detection probe preferably consists of or is contained within and includes at least 19, 22 or 24 contiguous bases of the base sequence of SEQ ID NO:24, the complement thereof, or an equivalent sequence containing thymine bases substituted for uracil bases, and which preferentially hybridizes to the target nucleic acid or its complement under stringent hybridization conditions. In certain embodiments the probe optionally includes one or more detectable labels, e.g., an AE substituent.

For certain amplification reactions in which the target nucleic acid contains a 16S rRNA sequence of *Mycobacterium tuberculosis*, the present invention includes a promoter oligonucleotide comprising a promoter sequence and a hybridizing sequence up to 40 or 50 bases in length. The promoter sequence is recognized by an RNA polymerase, such as a T7, T3 or SP6 RNA polymerase, and preferably includes the T7 RNA polymerase promoter sequence of SEQ ID NO:3. The hybridizing sequence of the preferred promoter oligonucleotide comprises, consists of, consists essentially of, overlaps with, or is contained within and includes at least 10, 15, 20, 25, 30, 35 or 36 contiguous bases of a base sequence that is at least 80%, 90% or 100% identical to the base sequence of SEQ ID NO:25 actgggtctaataccggataggaccacgggatgcat or an equivalent sequence containing uracil bases substituted for thymine bases, and which hybridizes to the target nucleic acid under amplification conditions. The promoter oligonucleotide preferably does not include a region in addition to the hybridizing sequence that hybridizes to the target nucleic acid under amplification conditions. More preferably, the promoter oligonucleotide comprises, consists of, or consists essentially of a base sequence substantially corresponding to the base sequence of SEQ ID NO:26 aattctaatacgactcactatagggagaactgggtctaataccggataggaccacgggatgcat or an equivalent sequence containing uracil bases substituted for thymine bases, and which hybridizes to the target nucleic acid under amplification conditions. The base sequence of the promoter oligonucleotide preferably consists of a promoter sequence and a hybridizing sequence consisting of or contained within and including at least 10, 15, 20, 25, 30, 35 or 36 contiguous bases of the base sequence of SEQ ID NO:25 or an equivalent sequence containing uracil bases substituted for thymine bases, and which hybridizes to the target nucleic acid under amplification conditions.

For certain amplification reactions in which the target nucleic acid contains a 16S rRNA sequence of *Mycobacterium tuberculosis*, the present invention includes a promoter oligonucleotide comprising a promoter sequence and a hybridizing sequence up to 40 or 50 bases in length. The promoter sequence is recognized by an RNA polymerase, such as a T7, T3 or SP6 RNA polymerase, and preferably includes the T7 RNA polymerase promoter sequence of SEQ ID NO:3. The hybridizing sequence of the preferred promoter oligonucleotide comprises, consists of, consists essentially of, overlaps with, or is contained within and includes at least 10, 15, 20, 25, 30 or 31 contiguous bases of a base sequence that is at least 80%, 90% or 100% identical to the base sequence of SEQ ID NO:27 actgggtctaataccggataggaccacggga or an equivalent sequence containing uracil bases substituted for thymine bases, and which hybridizes to the target nucleic acid under amplification conditions. The promoter oligonucleotide preferably does not include a region in addition to the hybridizing sequence that hybridizes to the target nucleic acid under amplification conditions. More preferably, the promoter oligonucleotide comprises, consists of, or consists essentially of a base sequence substantially corresponding to the base sequence of SEQ ID NO:28 aattctaatacgactcactat agggagaactgggtctaataccggataggaccacggga or an equivalent sequence containing uracil bases substituted for thymine bases, and which hybridizes to the target nucleic acid under amplification conditions. The base sequence of the promoter oligonucleotide preferably consists of a promoter sequence and a hybridizing sequence consisting of or contained within and including at least 10, 15, 20, 25, 30 or 31 contiguous bases of the base sequence of SEQ ID NO:27 or an equivalent sequence containing uracil bases substituted for thymine bases, and which hybridizes to the target nucleic acid under amplification conditions.

For certain amplification reactions in which the target nucleic acid contains a 16S rRNA sequence of *Mycobacterium tuberculosis*, the present invention includes a priming oligonucleotide up to 40 or 50 bases in length. A preferred priming oligonucleotide includes an oligonucleotide comprising, consisting of, consisting essentially of, overlapping with, or contained within and including at least 10, 15, 20, 25 or 27 contiguous bases of a base sequence that is at least 80%, 90% or 100% identical to the base sequence of SEQ ID NO:29 gccgtcaccccaccaacaagctgatag or an equivalent sequence containing uracil bases substituted for thymine bases, and which hybridizes to the target nucleic acid under amplification conditions. More preferably, the priming oligonucleotide comprises, consists of, or consists essentially of a base sequence substantially corresponding to the base sequence of SEQ ID NO:29 or an equivalent sequence containing uracil bases substituted for thymine bases, and which hybridizes to the target nucleic acid under amplification conditions. The base sequence of the priming oligonucleotide preferably consists of or is contained within and includes at least 10, 15, 20, 25 or 27 contiguous bases of the base sequence of SEQ ID NO:29 or an equivalent sequence containing uracil bases substituted for thymine bases, and which hybridizes to the target nucleic acid under amplification conditions.

For certain amplification reactions in which the target nucleic acid contains a 16S rRNA sequence of *Mycobacterium tuberculosis*, the present invention is further directed to a detection probe up to 35, 50 or 100 bases in length. A preferred detection probe includes a target binding region which comprises, consists of, consists essentially of, overlaps with, or is contained within and includes at least 18, 20 or 22 contiguous bases of a base sequence that is at least 80%, 90% or 100% identical to the base sequence of SEQ ID NO:30 gcucaucccacaccgcuaaagc, the complement thereof, or an equivalent sequence containing thymine bases substituted for uracil bases, and which preferentially hybridizes to the target nucleic acid or its complement (e.g., not nucleic acid from a *Mycobacterium avium* complex organism) under stringent hybridization conditions. The detection probe preferably does not include a region in addition to the target binding region that hybridizes to the target nucleic acid or its complement under stringent hybridization conditions. More preferably, the detection probe comprises, consists of, or consists essentially of a base sequence substantially corresponding to the base sequence of SEQ ID NO:30, the complement thereof, or an equivalent sequence containing thymine bases substituted for uracil bases, and which preferentially hybridizes to the target nucleic acid or its complement under stringent hybridization conditions.

The base sequence of the detection probe preferably consists of or is contained within and includes at least 18, 20 or 22 contiguous bases of the base sequence of SEQ ID NO:30, the complement thereof, or an equivalent sequence containing thymine bases substituted for uracil bases, and which preferentially hybridizes to the target nucleic acid or its complement under stringent hybridization conditions. In certain embodiments the probe optionally includes one or more detectable labels, e.g., an AE substituent.

For certain amplification reactions in which the target nucleic acid contains a 16S rRNA sequence of *Mycobacterium tuberculosis*, the present invention is further directed to a detection probe up to 35, 50 or 100 bases in length. A preferred detection probe includes a target binding region which comprises, consists of, consists essentially of, overlaps with, or is contained within and includes at least 22, 25 or 28 contiguous bases of a base sequence that is at least 80%, 90% or 100% identical to the base sequence of SEQ ID NO:31 ccgagaucccacaccgcuaaagccucgg, the complement thereof, or an equivalent sequence containing thymine bases substituted for uracil bases, and which preferentially hybridizes to the target nucleic acid or its complement (e.g., not nucleic acid from a *Mycobacterium avium* complex organism) under stringent hybridization conditions. The detection probe preferably does not include a region in addition to the target binding region that hybridizes to the target nucleic acid or its complement under stringent hybridization conditions. More preferably, the detection probe comprises, consists of, or consists essentially of a base sequence substantially corresponding to the base sequence of SEQ ID NO:31, the complement thereof, or an equivalent sequence containing thymine bases substituted for uracil bases, and which preferentially hybridizes to the target nucleic acid or its complement under stringent hybridization conditions. The base sequence of the detection probe preferably consists of or is contained within and includes at least 22, 25 or 28 contiguous bases of the base sequence of SEQ ID NO:31, the complement thereof, or an equivalent sequence containing thymine bases substituted for uracil bases, and which preferentially hybridizes to the target nucleic acid or its complement under stringent hybridization conditions. In certain embodiments the probe optionally includes one or more detectable labels, e.g., a fluorophore/quencher dye pair.

For certain amplification reactions in which the target nucleic acid contains a 16S rRNA sequence of *Mycobacterium tuberculosis*, the present invention is further directed to a detection probe up to 35, 50 or 100 bases in length. A preferred detection probe includes a target binding region which comprises, consists of, consists essentially of, overlaps with, or is contained within and includes at least 18, 20 or 22 contiguous bases of a base sequence that is at least 80%, 90% or 100% identical to the base sequence of SEQ ID NO:32 gctcatcccacaccgctaaagc, the complement thereof, or an equivalent sequence containing uracil bases substituted for thymine bases, and which preferentially hybridizes to the target nucleic acid or its complement (e.g., not nucleic acid from a *Mycobacterium avium* complex organism) under stringent hybridization conditions. The detection probe preferably does not include a region in addition to the target binding region that hybridizes to the target nucleic acid or its complement under stringent hybridization conditions. More preferably, the detection probe comprises, consists of, or consists essentially of a base sequence substantially corresponding to the base sequence of SEQ ID NO:32, the complement thereof, or an equivalent sequence containing uracil bases substituted for thymine bases, and which preferentially hybridizes to the target nucleic acid or its complement under stringent hybridization conditions. The base sequence of the detection probe preferably consists of or is contained within and includes at least 18, 20 or 22 contiguous bases of the base sequence of SEQ ID NO:32, the complement thereof, or an equivalent sequence containing uracil bases substituted for thymine bases, and which preferentially hybridizes to the target nucleic acid or its complement under stringent hybridization conditions. In certain embodiments the probe optionally includes one or more detectable labels, e.g., an AE substituent.

For certain amplification reactions in which the target nucleic acid contains the orfX gene of a *Staphylococcus aureus* (e.g. a methicillin-resistant strain), the present invention includes a promoter oligonucleotide comprising a promoter sequence and a hybridizing sequence up to 40 or 50 bases in length. The promoter sequence is recognized by an RNA polymerase, such as a T7, T3 or SP6 RNA polymerase, and preferably includes the T7 RNA polymerase promoter sequence of SEQ ID NO:3 aatttaatacgactcactataggaga. The hybridizing sequence of the preferred promoter oligonucleotide comprises, consists of, consists essentially of, overlaps with, or is contained within and includes at least 10, 15, 20, 25 or 29 contiguous bases of a base sequence that is at least 80%, 90% or 100% identical to the base sequence of SEQ ID NO:33 tgacccaagggcaaagcgactttg or an equivalent sequence containing uracil bases substituted for thymine bases, and which hybridizes to the target nucleic acid under amplification conditions. The promoter oligonucleotide preferably does not include a region in addition to the hybridizing sequence that hybridizes to the target nucleic acid under amplification conditions. More preferably, the promoter oligonucleotide comprises, consists of, or consists essentially of a base sequence substantially corresponding to the base sequence of SEQ ID NO:34 aatttaatacgactcactataggagatgacccaagggcaaagcgactttg or an equivalent sequence containing uracil bases substituted for thymine bases, and which hybridizes to the target nucleic acid under amplification conditions. The base sequence of the promoter oligonucleotide preferably consists of a promoter sequence, such as SEQ ID NO:3, and a hybridizing sequence consisting of or contained within and including at least 10, 15, 20, 25 or 29 contiguous bases of the base sequence of SEQ ID NO:33 or an equivalent sequence containing uracil bases substituted for thymine bases, and which hybridizes to the target nucleic acid under amplification conditions.

For certain amplification reactions in which the target nucleic acid contains the orfX gene of a *Staphylococcus aureus* (e.g. a methicillin-resistant strain), the present invention includes a priming oligonucleotide up to 40 or 50 bases in length. A preferred priming oligonucleotide includes an oligonucleotide comprising, consisting of, consisting essentially of, overlapping with, or contained within and including at least 10, 15, 20, 25 or 26 contiguous bases of a base sequence that is at least 80%, 90% or 100% identical to the base sequence of SEQ ID NO:35 gtgcgtagttactgcgttgtaagacgtc or an equivalent sequence containing uracil bases substituted for thymine bases, and which hybridizes to the target nucleic acid under amplification conditions. More preferably, the priming oligonucleotide comprises, consists of, or consists essentially of a base sequence substantially corresponding to the base sequence of SEQ ID NO:35 or an equivalent sequence containing uracil bases substituted for thymine bases, and which hybridizes under amplification conditions to the target nucleic acid. The base sequence of the priming oligonucleotide preferably consists of or is contained within and includes at least 10, 15, 20, 25 or 26 contiguous bases of the base sequence of SEQ ID NO:35 or an equivalent sequence containing uracil bases substituted for thymine bases, and which hybridizes to the target nucleic acid under amplification conditions.

For certain amplification reactions in which the target nucleic acid contains the orfX gene of a *Staphylococcus aureus* (e.g. a methicillin-resistant strain), the present invention includes a priming oligonucleotide up to 40 or 50 bases in length. A preferred priming oligonucleotide includes an oligonucleotide comprising, consisting of, consisting essentially of, overlapping with, or contained within and including at least 10, 15, 20, 25 or 26 contiguous bases of a base sequence that is at least 80%, 90% or 100% identical to the base sequence of SEQ ID NO:36 ctgaatgatagtgcgtagttactgcg or an equivalent sequence containing uracil bases substituted for thymine bases, and which hybridizes to the target nucleic acid under amplification conditions. More preferably, the priming oligonucleotide comprises, consists of, or consists essentially of a base sequence substantially corresponding to the base sequence of SEQ ID NO:36 or an equivalent sequence containing uracil bases substituted for thymine bases, and which hybridizes under amplification conditions to the target nucleic acid. The base sequence of the priming oligonucleotide preferably consists of or is contained within and includes at least 10, 15, 20, 25 or 26 contiguous bases of the base sequence of SEQ ID NO:36 or an equivalent sequence containing uracil bases substituted for thymine bases, and which hybridizes to the target nucleic acid under amplification conditions.

For certain amplification reactions in which the target nucleic acid contains the orfX gene of a *Staphylococcus aureus* (e.g. a methicillin-resistant strain), the present invention is further directed to a detection probe up to 35, 50 or 100 bases in length. A preferred detection probe includes a target binding region which comprises, consists of, consists essentially of, overlaps with, or is contained within and includes at least 10, 12, 15 or 17 contiguous bases of a base sequence that is at least 80%, 90% or 100% identical to the base sequence of SEQ ID NO:37 ccgucauuggcggauca, the complement thereof, or an equivalent sequence containing thymine bases substituted for uracil bases, and which preferentially hybridizes to the target nucleic acid or its complement under stringent hybridization conditions. The detection probe preferably does not include a region in addition to the target binding region that hybridizes to the target nucleic acid or its complement under stringent hybridization conditions. More preferably, the base sequence of the target binding region of the detection probe comprises, consists of, or consists essentially of a base sequence substantially corresponding to the base sequence of SEQ ID NO:38, the complement thereof, or an equivalent sequence containing thymine bases substituted for uracil bases, and which preferentially hybridizes to the target nucleic acid or its complement under stringent hybridization conditions. The detection probe may be capable of forming a hairpin molecule through self-hybridization at its end portions, such as a "molecular beacon" or "molecular torch," as described infra, under the stringent hybridization conditions. In certain embodiments the probe optionally includes one or more detectable labels, e.g., a pair of interacting fluorescent labels.

For amplification reactions which do not form part of the present invention, the above-described promoter oligonucleotides may be modified to exclude the promoter sequence and/or the priming oligonucleotides may be modified to include a promoter sequence. Additionally, where the desired specificity for a target sequence can be achieved, the promoter oligonucleotides and/or the priming oligonucleotides described above may be modified and used as detection probes. Also, the above-described detection probes may be adapted for use as amplification oligonucleotides.

Other features and advantages of the invention will be apparent from the following description of the preferred embodiments thereof and from the claims.

BRIEF DESCRIPTION OF THE DRAWINGS

FIG. 7A depicts reactions without added template, and FIG. 7B depicts reactions with added template.

DETAILED DESCRIPTION OF THE INVENTION

Figure 1A:
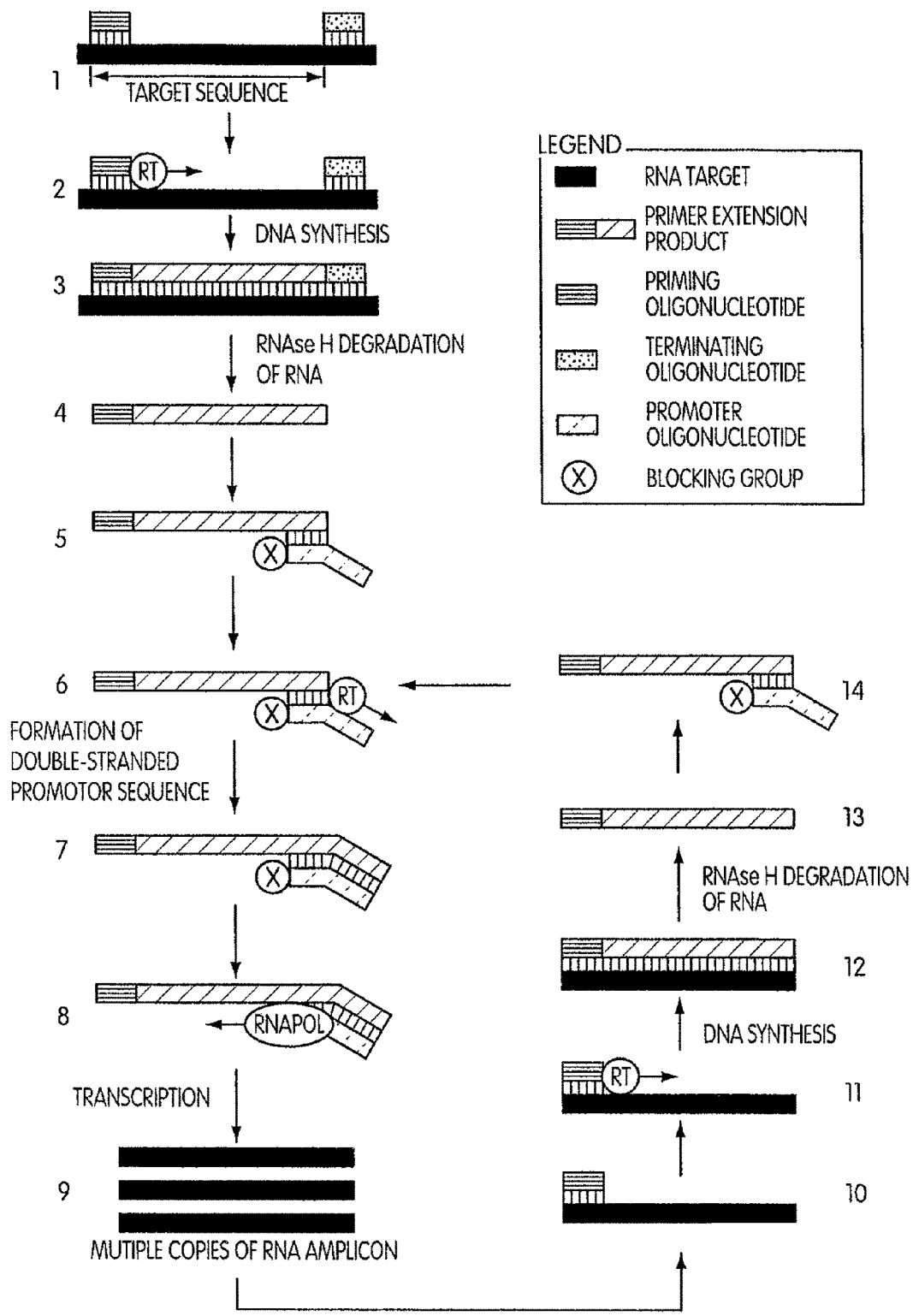
FIGS. 1A-1D depict four general methods of the present invention.

In accordance with the present invention, novel methods, reaction mixtures, compositions and kits are provided for the amplification of specific nucleic acid target sequences for use in assays for the detection and/or quantitation of such nucleic acid target sequences or for the production of large numbers of copies of DNA and/or RNA of specific target sequences for a variety of uses. In particular, the embodiments of the present invention provide for amplification of nucleic acid target sequences with enhanced specificity and sensitivity. Amplification methods of the present invention are preferably carried out using priming oligonucleotides that target only one sense of a target nucleic acid, with all other oligonucleotides used in the amplification methods preferably comprising a blocking moiety at their 3'-termini so that they cannot be extended by a nucleic acid polymerase.

Definitions

The following terms have the following meanings unless expressly stated to the contrary. It is to be noted that the term "a" or "an" entity refers to one or more of that entity; for example, "a nucleic acid," is understood to represent one or more nucleic acids. As such, the terms "a" (or "an"), "one or more," and "at least one" can be used interchangeably herein.

1. Nucleic Acid

The term "nucleic acid" is intended to encompass a singular "nucleic acid" as well as plural "nucleic acids," and refers to any chain of two or more nucleotides, nucleosides, or nucleobases (e.g., deoxyribonucleotides or ribonucleotides) covalently bonded together. Nucleic acids include, but are not limited to, virus genomes, or portions thereof, either DNA or RNA, bacterial genomes, or portions thereof, fungal, plant or animal genomes, or portions thereof, messenger RNA (mRNA), ribosomal RNA (rRNA), transfer RNA (tRNA), plasmid DNA, mitochondrial DNA, or synthetic DNA or RNA. A nucleic acid may be provided in a linear (e.g., mRNA), circular (e.g., plasmid), or branched form, as well as a double-stranded or single-stranded form. Nucleic acids may include modified bases to alter the function or behavior of the nucleic acid, e.g., addition of a 3'-terminal dideoxynucleotide to block additional nucleotides from being added to the nucleic acid. As used herein, a "sequence" of a nucleic acid refers to the sequence of bases which make up a nucleic acid. The term "polynucleotide" may be used herein to denote a nucleic acid chain. Throughout this application, nucleic acids are designated as having a 5'-terminus and a 3'-terminus. Standard nucleic acids, e.g., DNA and RNA, are typically synthesized "5'-to-3'," i.e., by the addition of nucleotides to the 3'-terminus of a growing nucleic acid.

A "nucleotide" is a subunit of a nucleic acid consisting of a phosphate group, a 5-carbon sugar and a nitrogenous base. The 5-carbon sugar found in RNA is ribose. In DNA, the 5-carbon sugar is 2'-deoxyribose. The term also includes analogs of such subunits, such as a methoxy group at the 2' position of the ribose (2'-O-Me). As used herein, methoxy oligonucleotides containing "T" residues have a methoxy group at the 2' position of the ribose moiety, and a uracil at the base position of the nucleotide.

A "non-nucleotide unit" is a unit which does not significantly participate in hybridization of a polymer. Such units must not, for example, participate in any significant hydrogen bonding with a nucleotide, and would exclude units having as a component one of the five nucleotide bases or analogs thereof.

2. Oligonucleotide

As used herein, the term "oligonucleotide" or "oligomer" is intended to encompass a singular "oligonucleotide" as well as plural "oligonucleotides," and refers to any polymer of two or more of nucleotides, nucleosides, nucleobases or related compounds used as a reagent in the amplification methods of the present invention, as well as subsequent detection methods. The oligonucleotide may be DNA and/or RNA and/or analogs thereof. The term oligonucleotide does not denote any particular function to the reagent, rather, it is used generically to cover all such reagents described herein. An oligonucleotide may serve various different functions, e.g., it may function as a primer if it is capable of hybridizing to a complementary strand and can further be extended in the presence of a nucleic acid polymerase, it may provide a promoter if it contains a sequence recognized by an RNA polymerase and allows for transcription, and it may function to prevent hybridization or impede primer extension if appropriately situated and/or modified. Specific oligonucleotides of the present invention are described in more detail below. As used herein, an oligonucleotide can be virtually any length, limited only by its specific function in the amplification reaction or in detecting an amplification product of the amplification reaction. Oligonucleotides of a defined sequence and chemical structure may be produced by techniques known to those of ordinary skill in the art, such as by chemical or biochemical synthesis, and by in vitro or in vivo expression from recombinant nucleic acid molecules, e.g., bacterial or viral vectors. As intended by this disclosure, an oligonucleotide does not consist solely of wild-type chromosomal DNA or the in vivo transcription products thereof.

Oligonucleotides may be modified in any way, as long as a given modification is compatible with the desired function of a given oligonucleotide. One of ordinary skill in the art can easily determine whether a given modification is suitable or desired for any given oligonucleotide of the present invention. Modifications include base modifications, sugar modifications or backbone modifications. Base modifications include, but are not limited to the use of the following bases in addition to adenine, cytidine, guanosine, thymine and uracil: C-5 propyne, 2-amino adenine, 5-methyl cytidine, inosine, and dP and dK bases. The sugar groups of the nucleoside subunits may be ribose, deoxyribose and analogs thereof, including, for example, ribonucleosides having a 2'-O-methyl substitution to the ribofuranosyl moiety. See Becker et al., U.S. Pat. No. 6,130,038. Other sugar modifications include, but are not limited to 2'-amino, 2'-fluoro, (L)-alpha-threofuranosyl, and pentopuranosyl modifications. The nucleoside subunits may by joined by linkages such as phosphodiester linkages, modified linkages or by non-nucleotide moieties which do not prevent hybridization of the oligonucleotide to its complementary target nucleic acid sequence. Modified linkages include those linkages in which a standard phosphodiester linkage is replaced with a different linkage, such as a phosphorothioate linkage or a methylphosphonate linkage. The nucleobase subunits may be joined, for example, by replacing the natural deoxyribose phosphate backbone of DNA with a pseudo peptide backbone, such as a 2-aminoethylglycine backbone which couples the nucleobase subunits by means of a carboxymethyl linker to the central secondary amine. (DNA analogs having a pseudo peptide backbone are referred to as "peptide nucleic acids" or "PNA" and disclosed by Nielsen et al., "Peptide Nucleic Acids," U.S. Pat. No. 5,539,082.) Other linkage modifications include, but are not limited to, morpholino bonds.

Non-limiting examples of oligonucleotides or oligomers contemplated by the present invention include nucleic acid analogs containing bicyclic and tricyclic nucleoside and nucleotide analogs (LNAs). See Imanishi et al., U.S. Pat. No. 6,268,490; and Wengel et al., U.S. Pat. No. 6,670,461.) Any nucleic acid analog is contemplated by the present invention provided the modified oligonucleotide can perform its intended function, e.g., hybridize to a target nucleic acid under stringent hybridization conditions or amplification conditions, or interact with a DNA or RNA polymerase, thereby initiating extension or transcription. In the case of detection probes, the modified oligonucleotides must also be capable of preferentially hybridizing to the target nucleic acid under stringent hybridization conditions.

While design and sequence of oligonucleotides for the present invention depend on their function as described below, several variables must generally be taken into account. Among the most critical are: length, melting temperature (Tm), specificity, complementarity with other oligonucleotides in the system, G/C content, polypyrimidine (T, C) or polypurine (A, G) stretches, and the 3'-end sequence. Controlling for these and other variables is a standard and well known aspect of oligonucleotide design, and various computer programs are readily available to screen large numbers of potential oligonucleotides for optimal ones.

The 3'-terminus of an oligonucleotide (or other nucleic acid) can be blocked in a variety of ways using a blocking moiety, as described below. A "blocked" oligonucleotide cannot be extended by the addition of nucleotides to its 3'-terminus, by a DNA- or RNA-dependent DNA polymerase, to produce a complementary strand of DNA. As such, a "blocked" oligonucleotide cannot be a "priming oligonucleotide."

As used in this disclosure, the phrase "an oligonucleotide having a nucleic acid sequence 'comprising,' 'consisting of,' or 'consisting essentially of' a sequence selected from" a group of specific sequences means that the oligonucleotide, as a basic and novel characteristic, is capable of stably hybridizing to a nucleic acid having the exact complement of one of the listed nucleic acid sequences of the group under stringent hybridization conditions. An exact complement includes the corresponding DNA or RNA sequence.

The phrase "an oligonucleotide substantially corresponding to a nucleic acid sequence" means that the referred to oligonucleotide is sufficiently similar to the reference nucleic acid sequence such that the oligonucleotide has similar hybridization properties to the reference nucleic acid sequence in that it would hybridize with the same target nucleic acid sequence under stringent hybridization conditions.

One skilled in the art will understand that "substantially corresponding" oligonucleotides of the invention can vary from the referred to sequence and still hybridize to the same target nucleic acid sequence. This variation from the nucleic acid may be stated in terms of a percentage of identical bases within the sequence or the percentage of perfectly complementary bases between the probe or primer and its target sequence. Thus, an oligonucleotide of the present invention substantially corresponds to a reference nucleic acid sequence if these percentages of base identity or complementarity are from 100% to about 80%. In preferred embodiments, the percentage is from 100% to about 85%. In more preferred embodiments, this percentage can be from 100% to about 90%; in other preferred embodiments, this percentage is from 100% to about 95%. One skilled in the art will understand the various modifications to the hybridization conditions that might be required at various percentages of complementarity to allow hybridization to a specific target sequence without causing an unacceptable level of non-specific hybridization.

3. Blocking Moiety

As used herein, a "blocking moiety" is a substance used to "block" the 3'-terminus of an oligonucleotide or other nucleic acid so that it cannot be extended by a nucleic acid polymerase. A blocking moiety may be a small molecule, e.g., a phosphate or ammonium group, or it may be a modified nucleotide, e.g., a 3'2' dideoxynucleotide or 3' deoxyadenosine 5'-triphosphate (cordycepin), or other modified nucleotide. Additional blocking moieties include, for example, the use of a nucleotide or a short nucleotide sequence having a 3'-to-5' orientation, so that there is no free hydroxyl group at the 3'-terminus, the use of a 3' alkyl group, a 3' non-nucleotide moiety (see, e.g., Arnold et al., "Non-Nucleotide Linking Reagents for Nucleotide Probes," U.S. Pat. No. 6,031,091, the contents of which are hereby incorporated by reference herein), phosphorothioate, alkane-diol residues, peptide nucleic acid (PNA), nucleotide residues lacking a 3' hydroxyl group at the 3'-terminus, or a nucleic acid binding protein. Preferably, the 3'-blocking moiety comprises a nucleotide or a nucleotide sequence having a 3'-to-5' orientation or a 3' non-nucleotide moiety, and not a 3'2'-dideoxynucleotide or a 3' terminus having a free hydroxyl group. Additional methods to prepare 3'-blocking oligonucleotides are well known to those of ordinary skill in the art.

4. Binding Molecule

As used herein, a "binding molecule" is a substance which hybridizes to or otherwise binds to a target nucleic acid adjacent to or near the 5'-end of the desired target sequence, so as to limit a DNA primer extension product to a desired length, i.e., a primer extension product having a generally defined 3'-end. As used herein, the phrase "defined 3'-end" means that the 3'-end of a primer extension product is not wholly indeterminate, as would be the case in a primer extension reaction which occurs in the absence of a binding molecule, but rather that the 3'-end of the primer extension product is generally known to within a small range of bases. In certain embodiments, a binding molecule comprises a base region. The base region may be DNA, RNA, a DNA:RNA chimeric molecule, or an analog thereof. Binding molecules comprising a base region may be modified in one or more ways, as described herein. Exemplary base regions include terminating and digestion oligonucleotides, as described below. In other embodiments, a binding molecule may comprise, for example, a protein or drug capable of binding RNA with sufficient affinity and specificity to limit a DNA primer extension product to a pre-determined length.

5. Terminating Oligonucleotide

In the present invention, a "terminating oligonucleotide" is an oligonucleotide comprising a base sequence that is complementary to a region of the target nucleic acid in the vicinity of the 5'-end of the target sequence, so as to "terminate" primer extension of a nascent nucleic acid that includes a priming oligonucleotide, thereby providing a defined 3'-end for the nascent nucleic acid strand. A terminating oligonucleotide is designed to hybridize to the target nucleic acid at a position sufficient to achieve the desired 3'-end for the nascent nucleic acid strand. The positioning of the terminating oligonucleotide is flexible depending upon its design. A terminating oligonucleotide may be modified or unmodified. In certain embodiments, terminating oligonucleotides are synthesized with at least one or more 2'-O-methyl ribonucleotides. These modified nucleotides have demonstrated higher thermal stability of complementary duplexes. The 2'-O-methyl ribonucleotides also function to increase the resistance of oligonucleotides to exonucleases, thereby increasing the half-life of the modified oligonucleotides. See, e.g., Majlessi et al. (1988) *Nucleic Acids Res.* 26, 2224-9, the contents of which are hereby incorporated by reference herein. Other modifications as described elsewhere herein may be utilized in addition to or in place of 2'-O-methyl ribonucleotides. For example, a terminating oligonucleotide may comprise PNA or an LNA. See, e.g., Petersen et al. (2000) *J. Mol. Recognit.* 13, 44-53, the contents of which are hereby incorporated by reference herein. Although not required, a terminating oligonucleotide of the present invention preferably includes a blocking moiety at its 3'-terminus to prevent extension. A terminating oligonucleotide may also comprise a protein or peptide joined to the oligonucleotide so as to terminate further extension of a nascent nucleic acid chain by a polymerase. A terminating oligonucleotide of the present invention is typically at least 10 bases in length, and may extend up to 15, 20, 25, 30, 35, 40, 50 or more nucleotides in length. Suitable and preferred terminating oligonucleotides are described herein. It should be noted that while a terminating oligonucleotide typically or necessarily includes a 3'-blocking moiety, "3'-blocked" oligonucleotides are not necessarily terminating oligonucleotides. Other oligonucleotides of the present invention, e.g., promoter oligonucleotides and capping oligonucleotides are typically or necessarily 3'-blocked as well.

6. Modifying Oligonucleotide/Digestion Oligonucleotide

A modifying oligonucleotide provides a mechanism by which the 3'-terminus of the primer extension product is determined. A modifying oligonucleotide typically comprises a motif which hybridizes to one or more bases in the vicinity of the 5'-end of a target sequence, and which facilitates termination of primer extension by means of a modifying enzyme, e.g., a nuclease. Alternatively, a modifying oligonucleotide might comprise a base region which hybridizes in the vicinity of the 3'-end of a target sequence, and is tethered to a specific modifying enzyme or to a chemical which can then terminate primer extension.

One specific modifying oligonucleotide is a digestion oligonucleotide. A digestion oligonucleotide is comprised of DNA, preferably a stretch of at least about 6 deoxyribonucleotides. The digestion oligonucleotide hybridizes to the RNA template, and the RNA of a RNA:DNA hybrid is digested by a selective RNAse as described herein, e.g., by an enzyme having an RNAse H activity.

7. Promoter Oligonucleotide/Promoter Sequence

As is well known in the art, a "promoter" is a specific nucleic acid sequence that is recognized by a DNA-dependent RNA polymerase ("transcriptase") as a signal to bind to the nucleic acid and begin the transcription of RNA at a specific site. For binding, it was generally thought that such transcriptases required DNA which had been rendered double-stranded in the region comprising the promoter sequence via an extension reaction, however, the present inventors have determined that efficient transcription of RNA can take place even under conditions where a double-stranded promoter is not formed through an extension reaction with the template nucleic acid. The template nucleic acid (the sequence to be transcribed) need not be double-stranded. Individual DNA-dependent RNA polymerases recognize a variety of different promoter sequences which can vary markedly in their efficiency in promoting transcription. When an RNA polymerase binds to a promoter sequence to initiate transcription, that promoter sequence is not part of the sequence transcribed. Thus, the RNA transcripts produced thereby will not include that sequence.

According to the present invention, a "promoter oligonucleotide" refers to an oligonucleotide comprising first and second regions, and which is modified to prevent the initiation of DNA synthesis from its 3'-terminus. The "first region" of a promoter oligonucleotide of the present invention comprises a base sequence which hybridizes to a DNA template, where the hybridizing sequence is situated 3', but not necessarily adjacent to, a promoter region. The hybridizing portion of a promoter oligonucleotide of the present invention is typically at least 10 nucleotides in length, and may extend up to 15, 20, 25, 30, 35, 40, 50 or more nucleotides in length. The "second region" comprises a promoter for an RNA polymerase. A promoter oligonucleotide of the present invention is engineered so that it is incapable of being extended by an RNA- or DNA-dependent DNA polymerase, e.g., reverse transcriptase, preferably comprising a blocking moiety at its 3'-terminus as described above. Suitable and preferred promoter oligonucleotides are described herein.

Promoter oligonucleotides of the present invention may be provided to a reaction mixture with an oligodeoxynucleotide bound to a ribonucleotide-containing section of the first region. The ribonucleotide-containing section preferably comprises at least 6 contiguous ribonucleotides positioned at or near the 3'-end of the first region, and the oligodeoxynucleotide is preferably the same length as and fully complementary to the ribonucleotide-containing section of the first region. Upon exposure to an enzyme capable of cleaving the RNA of an RNA:DNA duplex (e.g., an RNAse H activity), a blocking moiety at the 3'-end of the promoter oligonucleotide is released and the remainder of the first region is in a single-stranded form which is available for hybridization to a DNA template. The remaining, uncleaved portion of the first region is preferably 10 to 50 nucleotides in length, as described above.

Promoter oligonucleotides of the present invention may be used in methods disclosed herein to distinguish between regions of variability in the target sequence or between the target sequence and non-target nucleic acid which may be present in a reaction mixture (e.g., single nucleotide polymorphisms ("SNPs") or mismatches between closely related organisms or strains). When a primer extension product or nucleic acid sharing a high degree of sequence identity with a target nucleic acid contains one or more base mismatches with the target binding portion of a promoter oligonucleotide, the complements of these mismatched bases are integrated into the transcription products and the mismatched bases are then reproduced in initial and/or subsequent rounds of primer extension, thereby affecting the efficiency and sensitivity of the amplification reaction. Additionally, mismatches between the target binding portion of the promoter oligonucleotide and the primer extension product may interfere with the formation of a double-stranded promoter sequence in the presence of a reverse transcriptase, thereby further affecting the efficiency of the amplification reaction. These deleterious effects on an amplification reaction can be exploited to distinguish between nucleic acids exhibiting sequence variability in the region targeted by the promoter oligonucleotide.

8. Insertion Sequence

As used herein, an "insertion sequence" is a sequence positioned between the first region (i.e., template binding portion) and the second region of a promoter oligonucleotide. Insertion sequences are preferably 5 to 20 nucleotides in length, more preferably 6 to 18 nucleotides in length, and most preferably 6 to 12 nucleotides in length. The inclusion of insertion sequences in promoter oligonucleotides increases the rate at which RNA amplification products are formed. Exemplary insertion sequences are described herein.

9. Extender Oligonucleotide

An extender oligonucleotide is an oligonucleotide which hybridizes to a DNA template adjacent to or near the 3'-end of the first region of a promoter oligonucleotide. An extender oligonucleotide preferably hybridizes to a DNA template such that the 5'-terminal base of the extender oligonucleotide is within 3, 2 or 1 bases of the 3'-terminal base of a promoter oligonucleotide. Most preferably, the 5'-terminal base of an extender oligonucleotide is adjacent to the 3'-terminal base of a promoter oligonucleotide when the extender oligonucleotide and the promoter oligonucleotide are hybridized to a DNA template. To prevent extension of an extender oligonucleotide, a 3'-terminal blocking moiety is typically included. An extender oligonucleotide is preferably 10 to 50 nucleotides in length, more preferably 20 to 40 nucleotides in length, and most preferably 30 to 35 nucleotides in length.

10. Priming Oligonucleotide

A priming oligonucleotide is an oligonucleotide, at least the 3'-end of which is complementary to a nucleic acid template, and which hybridizes to the template to give a priming oligonucleotide:template hybrid suitable for initiation of synthesis by an RNA- or DNA-dependent DNA polymerase. A priming oligonucleotide is extended by the addition of covalently bonded nucleotides to its 3'-terminus, which nucleotides are complementary to the template. The result is a primer extension product. A priming oligonucleotide of the present invention is typically at least 10 nucleotides in length, and may extend up to 15, 20, 25, 30, 35, 40, 50 or more nucleotides in length. Suitable and preferred priming oligonucleotides are described herein. Virtually all DNA polymerases (including reverse transcriptases) that are known require hybridization of an oligonucleotide to a single-stranded template ("priming") to initiate DNA synthesis, whereas RNA replication and transcription (copying of RNA from DNA) generally do not require a primer. Because of its function, a priming oligonucleotide cannot comprise a 3'-blocking moiety that prevents extension in the presence of a DNA polymerase. Priming oligonucleotides are preferably designed to preferentially hybridize to a target nucleic acid, and so that it cannot be cleaved by a ribonuclease when hybridized to the target nucleic acid.

11. Displacer Oligonucleotide

A "displacer oligonucleotide" is a priming oligonucleotide which hybridizes to a template nucleic acid upstream from a neighboring priming oligonucleotide hybridized to the 3'-end of a target sequence (referred to herein as the "forward priming oligonucleotide"). By "upstream" is meant that a 3'-end of the displacer oligonucleotide complexes with the template nucleic acid 5' to a 3'-end of the forward priming oligonucleotide. When hybridized to the template nucleic acid, the 3'-terminal base of the displacer oligonucleotide is preferably adjacent to or spaced from the 5-terminal base of the forward priming oligonucleotide. More preferably, the 3'-terminal base of the displacer oligonucleotide is spaced from 5 to 35 bases from the 5'-terminal base of the forward priming oligonucleotide. The displacer oligonucleotide may be provided to a reaction mixture contemporaneously with the forward priming oligonucleotide or after the forward priming oligonucleotide has had sufficient time to hybridize to the template nucleic acid. Extension of the forward priming oligonucleotide can be initiated prior to or after the displacer oligonucleotide is provided to a reaction mixture. Under amplification conditions, the displacer oligonucleotide is extended in a template-dependent manner, thereby displacing a primer extension product comprising the forward priming oligonucleotide which is complexed with the template nucleic acid. Once displaced from the template nucleic acid, the primer extension product comprising the forward priming oligonucleotide is available for complexing with a promoter oligonucleotide. The forward priming oligonucleotide and the displacer oligonucleotide both preferentially hybridize to the target nucleic acid.

12. Cap or Capping Oligonucleotide

As used herein, a "cap" comprises an oligonucleotide complementary to the 3'-end of a priming oligonucleotide, where the 5'-terminal base of the cap hybridizes to the 3'-terminal base of the priming oligonucleotide. A cap according to present invention is designed to preferentially hybridize to the 3'-end of the priming oligonucleotide, e.g., not with a promoter oligonucleotide, but such that the cap will be displaced by hybridization of the priming oligonucleotide to the target nucleic acid. A cap may take the form of a discrete capping oligonucleotide or it may be joined to the 5'-end of the priming oligonucleotide via a linker region, thereby forming a stem-loop structure with the priming oligonucleotide under amplification conditions. Such a linker region can comprise conventional nucleotides, abasic nucleotides or otherwise modified nucleotides, or a non-nucleotide region. As described in more detail herein, a suitable cap is at least three bases in length, and is no longer than about 14 bases in length. Typical caps are about 5 to 7 bases in length.

13. Probe

By "probe" or "detection probe" is meant a molecule comprising an oligonucleotide having a base sequence partly or completely complementary to a region of an amplification product containing either sense of a target sequence sought to be detected, so as to hybridize thereto under stringent hybridization conditions. As would be understood by someone having ordinary skill in the art, a probe comprises an isolated nucleic acid molecule, or an analog thereof, in a form not found in nature without human intervention (e.g., recombined with foreign nucleic acid, isolated, or purified to some extent).

The probes of this invention may have additional nucleotides outside of the targeted region so long as such nucleotides do not substantially affect hybridization under stringent hybridization conditions and, in the case of detection probes, do not prevent preferential hybridization to the target sequence. A non-complementary sequence may also be included, such as a target capture sequence (generally a homopolymer tract, such as a poly-A, poly-T or poly-U tail), promoter sequence, a binding site for RNA transcription, a restriction endonuclease recognition site, or may contain sequences which will confer a desired secondary or tertiary structure, such as a catalytic active site or a hairpin structure on the probe, on the target nucleic acid, or both.

The probes preferably include at least one detectable label. The label may be any suitable labeling substance, including but not limited to a radioisotope, an enzyme, an enzyme cofactor, an enzyme substrate, a dye, a hapten, a chemiluminescent molecule, a fluorescent molecule, a phosphorescent molecule, an electrochemiluminescent molecule, a chromophore, a base sequence region that is unable to stably hybridize to the target nucleic acid under the stated conditions, and mixtures of these. In one particularly preferred embodiment, the label is an acridinium ester. Probes may also include interacting labels which emit different signals, depending on whether the probes have hybridized to target sequences. Examples of interacting labels include enzyme/substrates, enzyme/cofactor, luminescent/quencher, luminescent/adduct, dye dimers, and Förrester energy transfer pairs. Certain probes of the present invention do not include a label. For example, non-labeled "capture" probes may be used to enrich for target sequences or replicates thereof, which may then be detected by a second "detection" probe. See, e.g., Weisburg et al., "Two-Step Hybridization and Capture of a Polynucleotide," U.S. Pat. No. 6,534,273, the contents of which are hereby incorporated by reference herein. While detection probes are typically labeled, certain detection technologies do not require that the probe be labeled for detection of the amplification product. See, e.g., Nygren et al., "Devices and Methods for Optical Detection of Nucleic Acid Hybridization, U.S. Pat. No. 6,060,237.

By "stable" or "stable for detection" is meant that the temperature of a reaction mixture is at least 2° C. below the melting temperature of a nucleic acid duplex. The temperature of the reaction mixture is more preferably at least 5° C. below the melting temperature of the nucleic acid duplex, and even more preferably at least 10° C. below the melting temperature of the nucleic acid duplex.

By "preferentially hybridize" is meant that under stringent hybridization conditions, probes of the present invention hybridize to an amplification product containing either sense of the target sequence to form stable probe:target hybrids, while at the same time formation of stable probe:non-target hybrids is minimized. Thus, a probe hybridizes to a target sequence or replicate thereof to a sufficiently greater extent than to a non-target sequence, to enable one having ordinary skill in the art to accurately quantitate the RNA replicates or complementary DNA (cDNA) of the target sequence formed during the amplification.

Probes of a defined sequence may be produced by techniques known to those of ordinary skill in the art, such as by chemical synthesis, and by in vitro or in vivo expression from recombinant nucleic acid molecules. Preferably probes are 10 to 100 nucleotides in length, more preferably 12 to 50 bases in length, and even more preferably 18 to 35 bases in length.

14. Hybridize/Hybridization

Nucleic acid hybridization is the process by which two nucleic acid strands having completely or partially complementary nucleotide sequences come together under predetermined reaction conditions to form a stable, double-stranded hybrid. Either nucleic acid strand may be a deoxyribonucleic acid (DNA) or a ribonucleic acid (RNA) or analogs thereof. Thus, hybridization can involve RNA:RNA hybrids, DNA:DNA hybrids, RNA:DNA hybrids, or analogs thereof. The two constituent strands of this double-stranded structure, sometimes called a hybrid, are held together by hydrogen bonds. Although these hydrogen bonds most commonly form between nucleotides containing the bases adenine and thymine or uracil (A and T or U) or cytosine and guanine (C and G) on single nucleic acid strands, base pairing can also form between bases which are not members of these "canonical" pairs. Non-canonical base pairing is well-known in the art. (See, e.g., ROGER L. P. ADAMS ET AL., THE BIOCHEMISTRY OF THE NUCLEIC ACIDS ($11^{th}$ ed. 1992).)

"Stringent hybridization conditions" or "stringent conditions" refer to conditions wherein a specific detection probe is able to hybridize to an amplification product containing either sense of a target sequence over other nucleic acids present in a reaction mixture. It will be appreciated that these conditions may vary depending upon factors including the GC content and length of the probe, the hybridization temperature, the composition of the hybridization reagent or solution, and the degree of hybridization specificity sought. Specific stringent hybridization conditions are provided in the disclosure below.

By "nucleic acid hybrid" or "hybrid" or "duplex" is meant a nucleic acid structure containing a double-stranded, hydrogen-bonded region wherein each strand is complementary to the other, and wherein the region is sufficiently stable under stringent hybridization conditions to be detected by means including, but not limited to, chemiluminescent or fluorescent light detection, autoradiography, or gel electrophoresis. Such hybrids may comprise RNA:RNA, RNA:DNA, or DNA:DNA duplex molecules.

By "complementary" is meant that the nucleotide sequences of similar regions of two single-stranded nucleic acids, or to different regions of the same single-stranded nucleic acid have a nucleotide base composition that allow the single-stranded regions to hybridize together in a stable, double-stranded hydrogen-bonded region under stringent hybridization or amplification conditions. When a contiguous sequence of nucleotides of one single-stranded region is able to form a series of "canonical" hydrogen-bonded base pairs with an analogous sequence of nucleotides of the other single-stranded region, such that A is paired with U or T and C is paired with G, the nucleotides sequences are "perfectly" complementary.

By "preferentially hybridize" is meant that under stringent hybridization conditions, certain complementary nucleotide sequences hybridize to form a stable hybrid preferentially over other, less stable duplexes.

15. Nucleic Acid "Identity"

In certain embodiments, a nucleic acid of the present invention comprises a contiguous base region that is at least 80%, 90%, or 100% identical to a contiguous base region of a reference nucleic acid. For short nucleic acids, e.g., certain oligonucleotides of the present invention, the degree of identity between a base region of a "query" nucleic acid and a base region of a reference nucleic acid can be determined by manual alignment. "Identity" is determined by comparing just the sequence of nitrogenous bases, irrespective of the sugar and backbone regions of the nucleic acids being compared. Thus, the query:reference base sequence alignment may be DNA:DNA, RNA:RNA, DNA:RNA, RNA:DNA, or any combinations or analogs thereof. Equivalent RNA and DNA base sequences can be compared by replacing uridine residues (in RNA) with thymidine residues (in DNA).

16. Target Nucleic Acid/Target Sequence

A "target nucleic acid" is a nucleic acid comprising a "target sequence" to be amplified. Target nucleic acids may be DNA or RNA as described herein, and may be either single-stranded or double-stranded. The target nucleic acid may include other sequences besides the target sequence which may not be amplified. Typical target nucleic acids include virus genomes, bacterial genomes, fungal genomes, plant genomes, animal genomes, rRNA, tRNA, or mRNA from viruses, bacteria or eukaryotic cells, mitochondrial DNA, or chromosomal DNA.

Target nucleic acids may be isolated from any number of sources based on the purpose of the amplification assay being carried out. Sources of target nucleic acids include, but are not limited to, clinical specimens, e.g., blood, urine, saliva, feces, semen, or spinal fluid, from criminal evidence, from environmental samples, e.g., water or soil samples, from food, from industrial samples, from cDNA libraries, or from total cellular RNA. By "isolated" it is meant that a sample containing a target nucleic acid is taken from its natural milieu, but the term does not connote any degree of purification. If necessary, target nucleic acids of the present invention are made available for interaction with the various oligonucleotides of the present invention. This may include, for example, cell lysis or cell permeabilization to release the target nucleic acid from cells, which then may be followed by one or more purification steps, such as a series of isolation and wash steps. See, e.g., Clark et al., "Method for Extracting Nucleic Acids from a Wide Range of Organisms," U.S. Pat. No. 5,786,208, the contents of which are hereby incorporated by reference herein. This is particularly important where the sample may contain components that can interfere with the amplification reaction, such as, for example, heme present in a blood sample. See Ryder et at., "Amplification of Nucleic Acids from Mononuclear Cells Using Iron Complexing and Other Agents," U.S. Pat. No. 5,639,599, the contents of which are hereby incorporated by reference herein. Methods to prepare target nucleic acids from various sources for amplification are well known to those of ordinary skill in the art. Target nucleic acids of the present invention may be purified to some degree prior to the amplification reactions described herein, but in other cases, the sample is added to the amplification reaction without any further manipulations.

The term "target sequence" refers to the particular nucleotide sequence of the target nucleic acid which is to be amplified. The "target sequence" includes the complexing sequences to which oligonucleotides (e.g., priming oligonucleotides and/or promoter oligonucleotides) complex during the processes of the present invention. Where the target nucleic acid is originally single-stranded, the term "target sequence" will also refer to the sequence complementary to the "target sequence" as present in the target nucleic acid. Where the "target nucleic acid" is originally double-stranded, the term "target sequence" refers to both the sense (+) and antisense (−) strands. In choosing a target sequence, the skilled artisan will understand that a "unique" sequence should be chosen so as to distinguish between unrelated or closely related target nucleic acids. As will be understood by those of ordinary skill in the art, "unique" sequences are judged from the testing environment. At least the sequences recognized by the detection probe (as described in more detail elsewhere herein) should be unique in the environment being tested, but need not be unique within the universe of all possible sequences. Furthermore, even though the target sequence should contain a "unique" sequence for recognition by a detection probe, it is not always the case that the priming oligonucleotide and/or promoter oligonucleotide are recognizing "unique" sequences. In some embodiments, it may be desirable to choose a target sequence which is common to a family of related organisms, for example, a sequence which is common to all HIV strains that might be in a sample. In other situations, a very highly specific target sequence, or a target sequence having at least a highly specific region recognized by the detection probe, would be chosen so as to distinguish between closely related organisms, for example, between pathogenic and non-pathogenic E. coli. A target sequence of the present invention may be of any practical length. A minimal target sequence includes the region which hybridizes to the priming oligonucleotide (or the complement thereof), the region which hybridizes to the hybridizing region of the promoter oligonucleotide (or the complement thereof), and a region used for detection, e.g., a region which hybridizes to a detection probe, described in more detail elsewhere herein. The region which hybridizes to the detection probe may overlap with or be contained within the region which hybridizes with the priming oligonucleotide (or its complement) or the hybridizing region of the promoter oligonucleotide (or its complement). In addition to the minimal requirements, the optimal length of a target sequence depends on a number of considerations, for example, the amount of secondary structure, or self-hybridizing regions in the sequence. Determining the optimal length is easily accomplished by those of ordinary skill in the art using routine optimization methods. Typically, target sequences of the present invention range from about 100 nucleotides in length to from about 150 to about 250 nucleotides in length. The optimal or preferred length may vary under different conditions, which can easily be tested by one of ordinary skill in the art according to the methods described herein. The term "amplicon" refers to a nucleic acid molecule that is generated during an amplification procedure and is substantially complementary or identical to a sequence contained within the target sequence.

17. Template

A "template" is a nucleic acid molecule that is being copied by a nucleic acid polymerase. A template may be single-stranded, double-stranded or partially double-stranded, depending on the polymerase. The synthesized copy is complementary to the template or to at least one strand of a double-stranded or partially double-stranded template. Both RNA and DNA are typically synthesized in the 5'-to-3' direction and the two strands of a nucleic acid duplex are aligned so that the 5'-termini of the two strands are at opposite ends of the duplex (and, by necessity, so then are the 3'-termini). While according to the present invention, a "target sequence" is always a "template," templates can also include secondary primer extension products and amplification products.

18. DNA-dependent DNA Polymerase

A "DNA-dependent DNA polymerase" is an enzyme that synthesizes a complementary DNA copy from a DNA template. Examples are DNA polymerase I from E. coli, bacteriophage T7 DNA polymerase, or DNA polymerases from bacteriophages T4, Phi-29, M2, or T5. DNA-dependent DNA polymerases of the present invention may be the naturally occurring enzymes isolated from bacteria or bacteriophages or expressed recombinantly, or may be modified or "evolved" forms which have been engineered to possess certain desirable characteristics, e.g., thermostability, or the ability to recognize or synthesize a DNA strand from various modified templates. All known DNA-dependent DNA polymerases require a complementary primer to initiate synthesis. It is known that under suitable conditions a DNA-dependent DNA polymerase may synthesize a complementary DNA copy from an RNA template. RNA-dependent DNA polymerases (described below) typically also have DNA-dependent DNA polymerase activity.

19. DNA-dependent RNA Polymerase (Transcriptase)

A "DNA-dependent RNA polymerase" or "transcriptase" is an enzyme that synthesizes multiple RNA copies from a double-stranded or partially-double-stranded DNA molecule having a promoter sequence that is usually double-stranded. The RNA molecules ("transcripts") are synthesized in the 5'-to-3' direction beginning at a specific position just downstream of the promoter. Examples of transcriptases are the DNA-dependent RNA polymerase from E. coli and bacteriophages T7, T3, and SP6.

20. RNA-dependent DNA polymerase (Reverse Transcriptase)

An "RNA-dependent DNA polymerase" or "reverse transcriptase" ("RT") is an enzyme that synthesizes a complementary DNA copy from an RNA template. All known reverse transcriptases also have the ability to make a complementary DNA copy from a DNA template; thus, they are both RNA- and DNA-dependent DNA polymerases. RTs may also have an RNAse H activity. Preferred is reverse transcriptase derived from Maloney murine leukemia virus (MMLV-RT). A primer is required to initiate synthesis with both RNA and DNA templates.

21. Selective RNAses

As used herein, a "selective RNAse" is an enzyme that degrades the RNA portion of an RNA:DNA duplex but not single-stranded RNA, double-stranded RNA or DNA. An exemplary selective RNAse is RNAse H. Enzymes other than RNAse H which possess the same or similar activity are also contemplated in the present invention. Selective RNAses may be endonucleases or exonucleases. Most reverse transcriptase enzymes contain an RNAse H activity in addition to their polymerase activities. However, other sources of the RNAse H are available without an associated polymerase activity. The degradation may result in separation of RNA from a RNA:DNA complex. Alternatively, a selective RNAse may simply cut the RNA at various locations such that portions of the RNA melt off or permit enzymes to unwind portions of the RNA. Other enzymes which selectively degrade RNA target sequences or RNA products of the present invention will be readily apparent to those of ordinary skill in the art.

22. Sense/Antisense Strand(s)

Discussions of nucleic acid synthesis are greatly simplified and clarified by adopting terms to name the two complementary strands of a nucleic acid duplex. Traditionally, the strand encoding the sequences used to produce proteins or structural RNAs are designated as the "sense (+)" strand and its complement the "antisense (−)" strand. It is now known that in many cases, both strands are functional, and the assignment of the designation "sense" to one and "antisense" to the other must then be arbitrary. Nevertheless, the terms are very useful for designating the sequence orientation of nucleic acids and will be employed herein for that purpose.

23. Specificity of the System

The term "specificity," in the context of an amplification system, is used herein to refer to the characteristic of an amplification system which describes its ability to distinguish between target and non-target sequences dependent on sequence and assay conditions. In terms of a nucleic acid amplification, specificity generally refers to the ratio of the number of specific amplicons produced to the number of side-products (i.e., the signal-to-noise ratio), described in more detail below.

24. Sensitivity

The term "sensitivity" is used herein to refer to the precision with which a nucleic acid amplification reaction can be detected or quantitated. The sensitivity of an amplification reaction is generally a measure of the smallest copy number of the target nucleic acid that can be reliably detected in the amplification system, and will depend, for example, on the detection assay being employed, and the specificity of the amplification reaction, i.e., the ratio of specific amplicons to side-products.

25. Amplification Conditions

By "amplification conditions" is meant conditions permitting nucleic acid amplification according to the present invention. Amplification conditions may, in some embodiments, be less stringent than "stringent hybridization conditions" as described herein. Oligonucleotides used in the amplification reactions of the present invention hybridize to their intended targets under amplification conditions, but may or may not hybridize under stringent hybridization conditions. On the other hand, detection probes of the present invention hybridize under stringent hybridization conditions. While the Examples section infra provides preferred amplification conditions for amplifying target nucleic acid sequences according to the present invention, other acceptable conditions to carry out nucleic acid amplifications according to the present invention could be easily ascertained by someone having ordinary skill in the art depending on the particular method of amplification employed.

* * *

The present invention provides an autocatalytic amplification method which synthesizes large numbers of RNA copies of an RNA or DNA target sequence with high specificity and sensitivity. An important aspect of the present invention is the minimal production of side-products during the amplification. Examples of side-products include oligonucleotide dimers and self-replicating molecules. The target nucleic acid contains the target sequence to be amplified. The target sequence is that region of the target nucleic acid which is defined on either end by priming oligonucleotides, promoter oligonucleotides, and, optionally, a binding molecule, e.g., a terminating oligonucleotide or a modifying oligonucleotide (described in more detail below), and/or the natural target nucleic acid termini, and includes both the sense and antisense strands. Promoter oligonucleotides of the present invention are modified to prevent the synthesis of DNA therefrom. Preferably, the promoter oligonucleotides comprise a blocking moiety attached at their 3'-termini to prevent primer extension in the presence of a polymerase. Indeed, according to the present invention, at least about 80% of the oligonucleotides present in the amplification reaction which comprise a promoter further comprise a 3'-blocking moiety. In further embodiments, at least about 85%, 90%, 95%, 96%, 97%, 98%, 99% or 100% of the oligonucleotides provided to the amplification reaction which comprise a promoter are further modified to comprise a 3'-blocking moiety. In a specific embodiment, any oligonucleotide used in an amplification reaction of the present invention which comprises a promoter sequence must further comprise a 3'-terminus blocking moiety.

One embodiment of the present invention comprises amplification of a target nucleic acid comprising an RNA target sequence. See FIGS. 1A and 1B. The target nucleic acid has indeterminate 3'- and 5'-ends relative to the desired RNA target sequence. The target nucleic acid is treated with a priming oligonucleotide which has a base region sufficiently complementary to a 3'-region of the RNA target sequence to hybridize therewith. See Step 1 of FIGS. 1A and 1B. Priming oligonucleotides are designed to hybridize to a suitable region of any desired target sequence, according to primer design methods well known to those of ordinary skill in the art. Suitable priming oligonucleotides are described in more detail herein. While a priming oligonucleotide of the present invention can optionally include a non-hybridizing base region situated 5' to the region which hybridizes with the target sequence, according to the present invention the 5' region of a priming oligonucleotide does not include a promoter sequence recognized by an RNA polymerase. Additionally, the 5'-end of the priming oligonucleotide may include one or modifications which improve the binding properties (e.g., hybridization or base stacking) of the priming oligonucleotide to a target sequence or RNA amplification product, as discussed more fully infra, provided the modifications do not substantially interfere with the priming function of the priming oligonucleotide or cleavage of a template RNA to which the priming oligonucleotide is hybridized. In the presence of nucleoside triphosphates and buffers, salts and cofactors, the 3'-end of the priming oligonucleotide is extended by an appropriate DNA polymerase, e.g., an RNA-dependent DNA polymerase ("reverse transcriptase") in an extension reaction using the RNA target sequence as a template to give a DNA primer extension product which is complementary to the RNA template. See Steps 2 and 3 of FIGS. 1A and 1B.

The DNA primer extension product is separated (at least partially) from the RNA template using an enzyme which degrades the RNA template. See Step 4 of FIGS. 1A and 1B. Suitable enzymes, i.e., "selective RNAses," are those which act on the RNA strand of an RNA:DNA complex, and include enzymes which comprise an RNAse H activity. Some reverse transcriptases include an RNAse H activity, including those derived from Moloney murine leukemia virus ("MMLV") and avian myeloblastosis virus ("AMV"). According to this method, the selective RNAse may be provided as an RNAse H activity of a reverse transcriptase, or may be provided as a separate enzyme, e.g., as an *E. coli* RNAse H or a *T. thermophilus* RNAse H. Other enzymes which selectively degrade RNA present in an RNA:DNA duplex may also be used.

In certain specific embodiments, the method of the present invention further comprises treating the target nucleic acid as described above to limit the length of the DNA primer extension product to a certain desired length. Such length limitation is typically carried out through use of a "binding molecule" which hybridizes to or otherwise binds to the RNA target nucleic acid adjacent to or near the 5'-end of the desired target sequence. See Step 1 of FIG. 1A. In certain embodiments, a binding molecule comprises a base region. The base region may be DNA, RNA, a DNA:RNA chimeric molecule, or an analog thereof. Binding molecules comprising a base region may be modified in one or more ways, as described elsewhere herein. Suitable binding molecules include, but are not limited to, a binding molecule comprising a terminating oligonucleotide or a terminating protein that binds RNA and prevents primer extension past its binding region, or a binding molecule comprising a modifying molecule, for example, a modifying oligonucleotide such as a "digestion" oligonucleotide that directs hydrolysis of that portion of the RNA target hybridized to the digestion oligonucleotide, or a sequence-specific nuclease that cuts the RNA target.

A terminating oligonucleotide of the present invention has a 5'-base region sufficiently complementary to the target nucleic acid at a region adjacent to, near to, or overlapping with the 5'-end of the target sequence, to hybridize therewith. In certain embodiments, a terminating oligonucleotide is synthesized to include one or more modified nucleotides. For example, certain terminating oligonucleotides of the present invention comprise one or more 2'-O-methyl ribonucleotides, or are synthesized entirely of 2'-O-methyl ribonucleotides. See, e.g., Majlessi et al. (1998) *Nucleic Acids Res.,* 26, 2224-2229. A terminating oligonucleotide of the present invention typically also comprises a blocking moiety at its 3'-end to prevent the terminating oligonucleotide from functioning as a primer for a DNA polymerase. In some embodiments, the 5'-end of a terminating oligonucleotide of the present invention overlaps with and is complementary to at least about 2 nucleotides of the 5'-end of the target sequence. Typically, the 5'-end of a terminating oligonucleotide of the present invention overlaps with and is complementary to at least 3, 4, 5, 6, 7, or 8 nucleotides of the 5'-end of the target sequence, but no more than about 10 nucleotides of the 5'-end of the target sequence. (As used herein, the term "end" refers to a 5'- or 3'-region of an oligonucleotide, nucleic acid or nucleic acid region which includes, respectively, the 5'- or 3'-terminal base of the oligonucleotide, nucleic acid or nucleic acid region.) Suitable terminating oligonucleotides are described in more detail herein.

Figure 5:
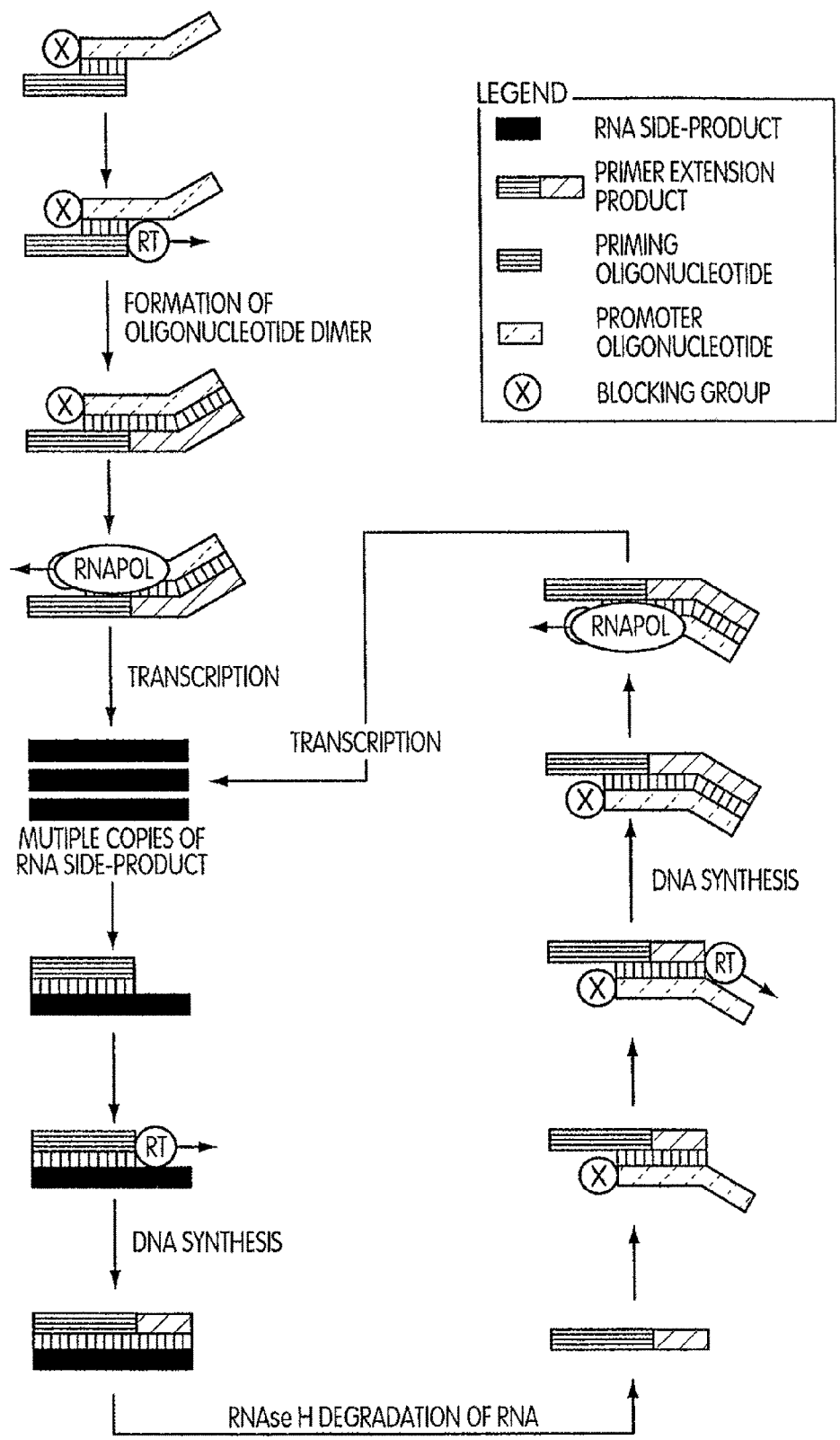
FIG. 5 illustrates the formation of primer-dependent side-products.

To the extent that a terminating oligonucleotide has a 5' base region which overlaps with the target sequence, it may be desirable to introduce one or more base mismatches into the 5'-end of the first region of a promoter oligonucleotide in order to minimize or prevent hybridization of the terminating oligonucleotide to the promoter oligonucleotide, as the formation of terminating oligonucleotide:promoter oligonucleotide hybrids may negatively affect the rate of an amplification reaction. While one base mismatch in the region of overlap generally should be sufficient, the exact number needed will depend upon factors such as the length and base composition of the overlapping region, as well as the conditions of the amplification reaction. Despite the possible benefits of a modified promoter oligonucleotide, it should be noted that mutations in the first region of the promoter oligonucleotide could render it a poorer template for amplification. Moreover, it is entirely possible that in a given amplification system the formation of terminating oligonucleotide:promoter oligonucleotide hybrids advantageously prevents or interferes with the formation of priming oligonucleotide:promoter oligonucleotides hybrids with a 3'-end available for primer extension. See FIG. 5 (formation of primer-dependent side-products).

A modifying oligonucleotide provides a mechanism by which the 3'-terminus of the primer extension product is determined. A modifying oligonucleotide may provide a motif comprising one or more bases in the vicinity of the 5'-end of the RNA target sequence which facilitates termination of primer extension by means of a modifying enzyme, e.g., a nuclease. Alternatively, a modifying oligonucleotide might be tethered to a specific modifying enzyme or to a chemical which can then terminate primer extension.

One specific modifying oligonucleotide is a digestion oligonucleotide. A digestion oligonucleotide is comprised of DNA, preferably a stretch of at least about 6 deoxyribonucleotides. The digestion oligonucleotide hybridizes to the RNA template and the RNA of the RNA:DNA hybrid is digested by a selective RNAse as described herein, e.g., by an RNAse H activity.

The single-stranded DNA primer extension product, or "first" DNA primer extension product, which has either a defined 3'-end or an indeterminate 3'-end, is then treated with a promoter oligonucleotide which comprises a first region sufficiently complementary to a 3'-region of the DNA primer extension product to hybridize therewith, a second region comprising a promoter for an RNA polymerase, e.g., T7 polymerase, which is situated 5' to the first region, e.g., immediately 5' to or spaced from the first region, and modified to prevent the promoter oligonucleotide from functioning as a primer for a DNA polymerase (e.g., the promoter oligonucleotide includes a blocking moiety attached at its 3'-terminus). See Step 5 of FIGS. 1A and 1B. Upon identifying a desired hybridizing "first region," suitable promoter oligonucleotides can be constructed by one of ordinary skill in the art using only routine procedures. Those of ordinary skill in the art will readily understand that a promoter region has certain nucleotides which are required for recognition by a given RNA polymerase. In addition, certain nucleotide variations in a promoter sequence might improve the functioning of the promoter with a given enzyme, including the use of insertion sequences.

Insertion sequences are positioned between the first and second regions of promoter oligonucleotides and function to increase amplification rates. The improved amplification rates may be attributable to several factors. First, because an insertion sequence increases the distance between the 3'-end and the promoter sequence of a promoter oligonucleotide, it is less likely that a polymerase, e.g., reverse transcriptase, bound at the 3'-end of the promoter oligonucleotide will interfere with binding of the RNA polymerase to the promoter sequence, thereby increasing the rate at which transcription can be initiated. Second, the insertion sequence selected may itself improve the transcription rate by functioning as a better template for transcription than the target sequence. Third, since the RNA polymerase will initiate transcription at the insertion sequence, the primer extension product synthesized by the priming oligonucleotide, using the RNA transcription product as a template, will contain the complement of the insertion sequence toward the 3'-end of the primer extension product. By providing a larger target binding region, i.e., one which includes the complement of the insertion sequence, the promoter oligonucleotide may bind to the primer extension product faster, thereby leading to the production of additional RNA transcription products sooner. Insertion sequences are preferably 5 to 20 nucleotides in length and should be designed to minimize intramolecular folding and intermolecular binding with other oligonucleotides present in the amplification reaction mixture. Programs which aid in minimizing secondary structure are well known in the art and include Michael Zucker's mfold software for predicting RNA and DNA secondary structure using nearest neighbor thermodynamic rules. The latest version of Michael Zucker's mfold software can be accessed on the Web at www.bioinfo.rpi.edu/applications/mfold using a hypertext transfer protocol (http) in the URL. Currently preferred insertion sequences include the nucleotide sequences of SEQ ID Nos. 1 and 2 in combination with the T7 RNA polymerase promoter sequence of SEQ ID NO:3. See Ikeda et al. (1992) *J. Biol. Chem.* 267, 2640-2649. Other useful insertion sequences may be identified using in vitro selection methods well known in the art.

Assaying promoter oligonucleotides with variations in the promoter sequences is easily carried out by the skilled artisan using routine methods. Furthermore, if it is desired to utilize a different RNA polymerase, the promoter sequence in the promoter oligonucleotide is easily substituted by a different promoter. Substituting different promoter sequences is well within the understanding and capabilities of those of ordinary skill in the art. It is important to note that according to the present invention, promoter oligonucleotides provided to the amplification reaction mixture are modified to prevent the initiation of DNA synthesis from their 3'-termini, and preferably comprise a blocking moiety attached at their 3'-termini. Furthermore, terminating oligonucleotides and capping oligonucleotides, and even probes used in the methods of the present invention also optionally comprise a blocking moiety attached at their 3'-termini.

Where a terminating oligonucleotide is used, the first region of the promoter oligonucleotide is designed to hybridize with a desired 3'-end of the DNA primer extension product with substantial, but not necessarily exact, precision. Subsequently, the second region of the promoter oligonucleotide may act as a template, allowing the first DNA primer extension product to be further extended to add a base region complementary to the second region of the promoter oligonucleotide, i.e., the region comprising the promoter sequence, rendering the promoter double-stranded. See Steps 6 and 7 of FIG. 1A. An RNA polymerase which recognizes the promoter binds to the promoter sequence, and initiates transcription of multiple RNA copies complementary to the DNA primer extension product, which copies are substantially identical to the target sequence. By "substantially identical" it is meant that the multiple RNA copies may have additional nucleotides either 5' or 3' relative to the target sequence, or may have fewer nucleotides either 5' or 3' relative to the target sequence, depending on, e.g., the boundaries of "the target sequence," the transcription initiation point, or whether the priming oligonucleotide comprises additional nucleotides 5' of the primer region (e.g., a linked "cap" as described herein). Where a target sequence is DNA, the sequence of the RNA copies is described herein as being "substantially identical" to the target sequence. It is to be understood, however, that an RNA sequence which has uridine residues in place of the thymidine residues of the DNA target sequence still has a "substantially identical" sequence. The RNA transcripts so produced may automatically recycle in the above system without further manipulation. Thus, this reaction is autocatalytic. In those embodiments where a binding molecule or other means for terminating a primer extension reaction is not used, the first region of the promoter oligonucleotide is designed to hybridize with a selected region of the first DNA primer extension product which is expected to be 5' to the 3'-terminus of the first DNA primer extension product, but since the 3'-terminus of the first DNA primer extension product is indeterminate, the region where the promoter oligonucleotide hybridizes probably will not be at the actual 3'-end of the first DNA primer extension product. According to this embodiment, it is generally the case that at least the 3'-terminal base of the first DNA primer extension product does not hybridize to the promoter oligonucleotide. See Step 5 of FIG. 1B. Thus, according to this embodiment the first DNA primer extension product will likely not be further extended to form a double-stranded promoter.

Figure 1B:
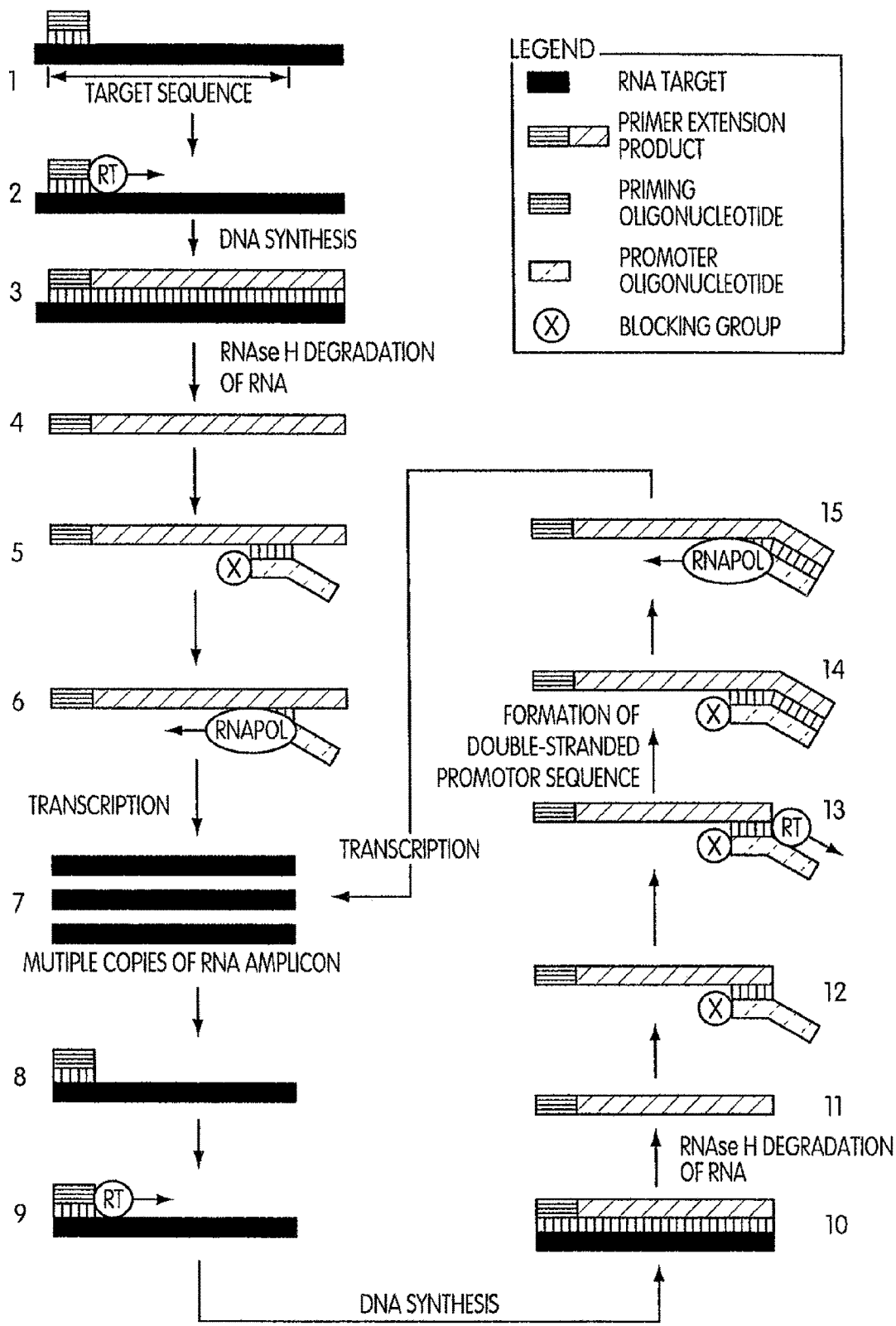

Surprisingly, the inventors discovered that the formation of a double-stranded promoter sequence through extension of a template nucleic acid is not necessary to permit initiation of transcription of RNA complementary to the first DNA primer extension product. See Step 6 of FIG. 1B. The resulting "first" RNA products are substantially identical to the target sequence, having a 5'-end defined by the transcription initiation point, and a 3'-end defined by the 5'-end of the first DNA primer extension product. See Step 7 of FIG. 1B. As illustrated in FIG. 1B, a sufficient number of first RNA products are produced to automatically recycle in the system without further manipulation. The priming oligonucleotide hybridizes to the 3'-end of the first RNA products, and is extended by a DNA polymerase to form a second DNA primer extension product. Unlike the first DNA primer extension product formed without the use of a terminating oligonucleotide or other binding molecule, the second DNA primer extension product has a defined 3'-end which is complementary to the 5'-ends of the first RNA products. See Steps 8-10 of FIG. 1B. The second DNA primer extension product is separated (at least partially) from the RNA template using an enzyme which selectively degrades the RNA template. See Step 11 of FIG. 1B. The single-stranded second DNA primer extension product is then treated with a promoter oligonucleotide as described above, and the second region of the promoter oligonucleotide acts as a template, allowing the second DNA primer extension product to be further extended to add a base region complementary to the second region of the promoter oligonucleotide, i.e., the region comprising the promoter sequence, rendering the promoter double-stranded. See Steps 12-14 of FIG. 1B. An RNA polymerase which recognizes the promoter binds to the promoter sequence, and initiates transcription of multiple "second" RNA products complementary to the second DNA primer extension product, and substantially identical to the target sequence. See Step 15 of FIG. 1B. The second RNA transcripts so produced automatically recycle in the above system without further manipulation. Thus, this reaction is autocatalytic. See Steps 7-15 of FIG. 1B.

Figure 1C:
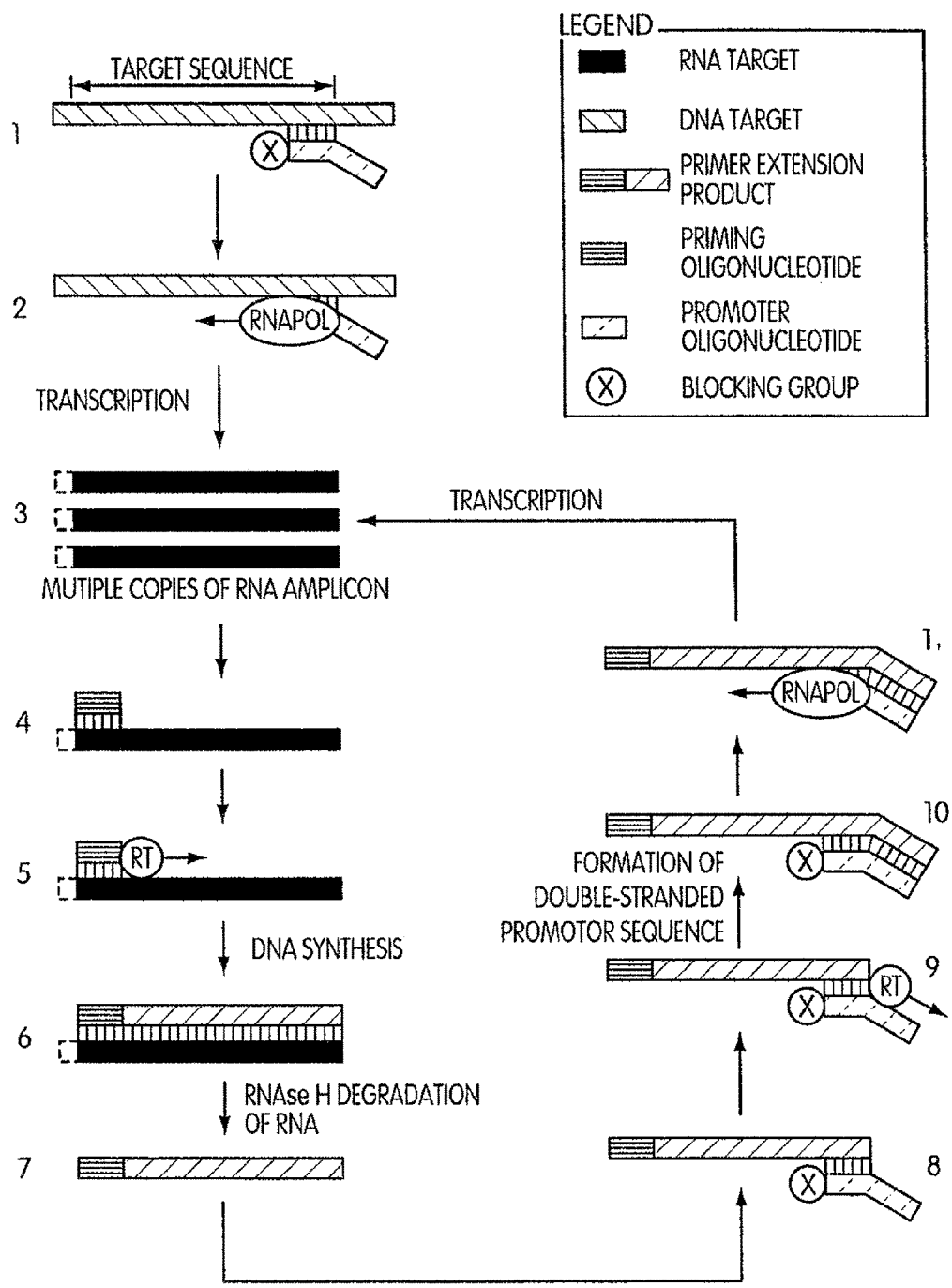

In another embodiment, the present invention is drawn to a method of synthesizing multiple copies of a target sequence from a target nucleic acid comprising a DNA target sequence. This embodiment is diagramed in FIG. 1C. The target nucleic acid may be either single-stranded, partially single-stranded, or double-stranded DNA. When the DNA is double-stranded, it is denatured, or partially denatured, prior to amplification. The DNA target nucleic acid need not have a defined 3'-end. The single-stranded, partially single-stranded, or denatured DNA target nucleic acid is treated with a promoter oligonucleotide as described above. The first region of the promoter oligonucleotide is designed to hybridize with a selected region of the target nucleic acid in the 3'-region of the desired target sequence, but since the 3'-end of the target nucleic acid need not be coterminal with the 3'-end of the target sequence, the region where the promoter oligonucleotide hybridizes will likely not be at or near the 3'-end of the target nucleic acid sequence. See Step 1 of FIG. 1C. Thus, the promoter region of the promoter oligonucleotide will likely remain single-stranded.

As noted above, the inventors surprisingly discovered that it is not necessary for the single-stranded promoter sequence on the promoter oligonucleotide to form a double-stranded promoter through extension of a template nucleic acid in order for the promoter sequence to be recognized by the corresponding RNA polymerase and, in this case, initiate transcription of RNA complementary to the DNA target sequence. See Step 2 of FIG. 1C. The resulting "first RNA products" have a 5'-end defined by the transcription initiation point for the promoter, however, the 3'-region will remain indeterminate. See Step 3 of FIG. 1C. These first RNA products are then treated with a priming oligonucleotide. The priming oligonucleotide hybridizes to a region of the first RNA products at a position complementary to a 5' region of the desired target sequence, and is extended by a DNA polymerase to form a DNA primer extension product. See Steps 4-6 of FIG. 1C. This DNA primer extension product has a 5'-end coinciding with the 5'-end of the priming oligonucleotide, and a 3'-end coinciding with the 5'-end of the first RNA products. See Step 6 of FIG. 1C. The DNA primer extension product is separated (at least partially) from its RNA template using an enzyme which selectively degrades the RNA template, as described above. See Step 7 of FIG. 1C. The DNA primer extension product is then treated with the promoter oligonucleotide, as described above, and the second region of the promoter oligonucleotide acts as a template, allowing the DNA primer extension product to be further extended to add a base region complementary to the second region of the promoter oligonucleotide, i.e., the region comprising the promoter, rendering the promoter double-stranded. See Steps 8-10 of FIG. 1C. An RNA polymerase which recognizes the promoter binds to the promoter sequence, and initiates transcription of multiple RNA products complementary to the DNA primer extension product. See Step 11 of FIG. 1C. The sequence of these "second RNA products" is substantially complementary to the desired target sequence. The RNA products so produced automatically recycle in the above system without further manipulation. Thus, this reaction is autocatalytic. See Steps 3-11 of FIG. 1C.

Figure 1D:
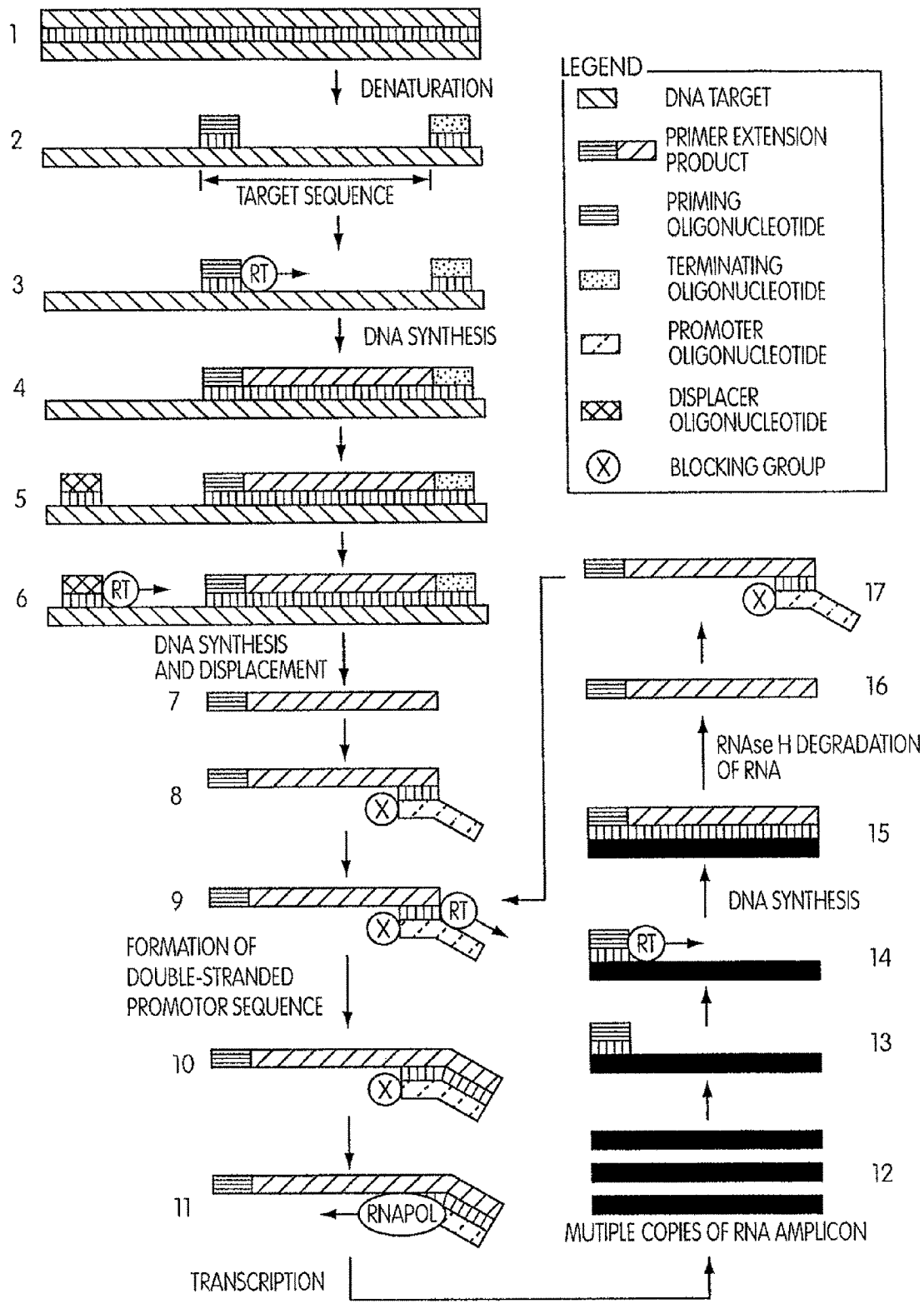
Figure 2A:
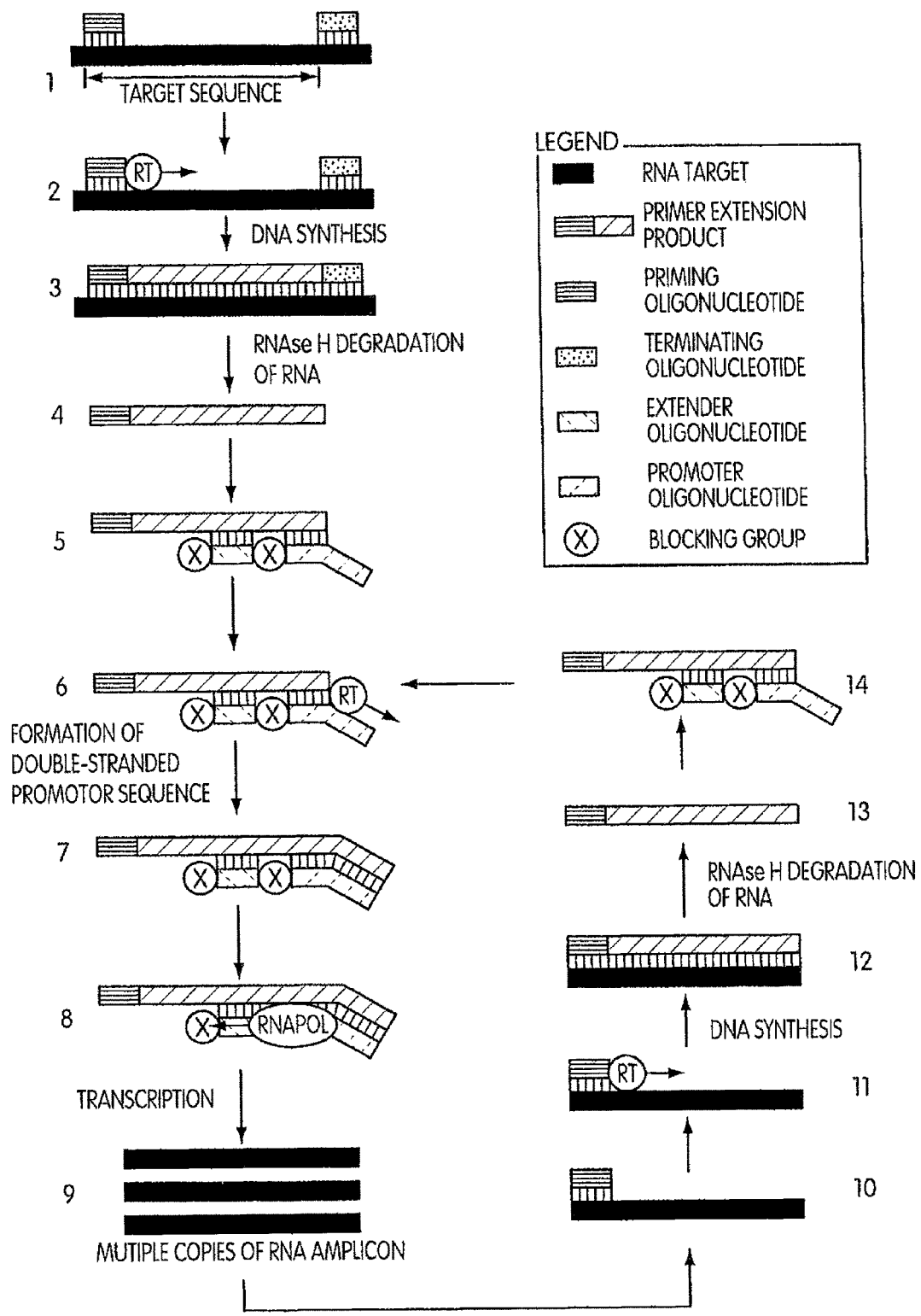
FIGS. 2A-2D depict the general methods of FIGS. 1A-1D with the further inclusion of an extender oligonucleotide hybridized to an extension product or target sequence 3' to the blocked promoter oligonucleotide.
Figure 2B:
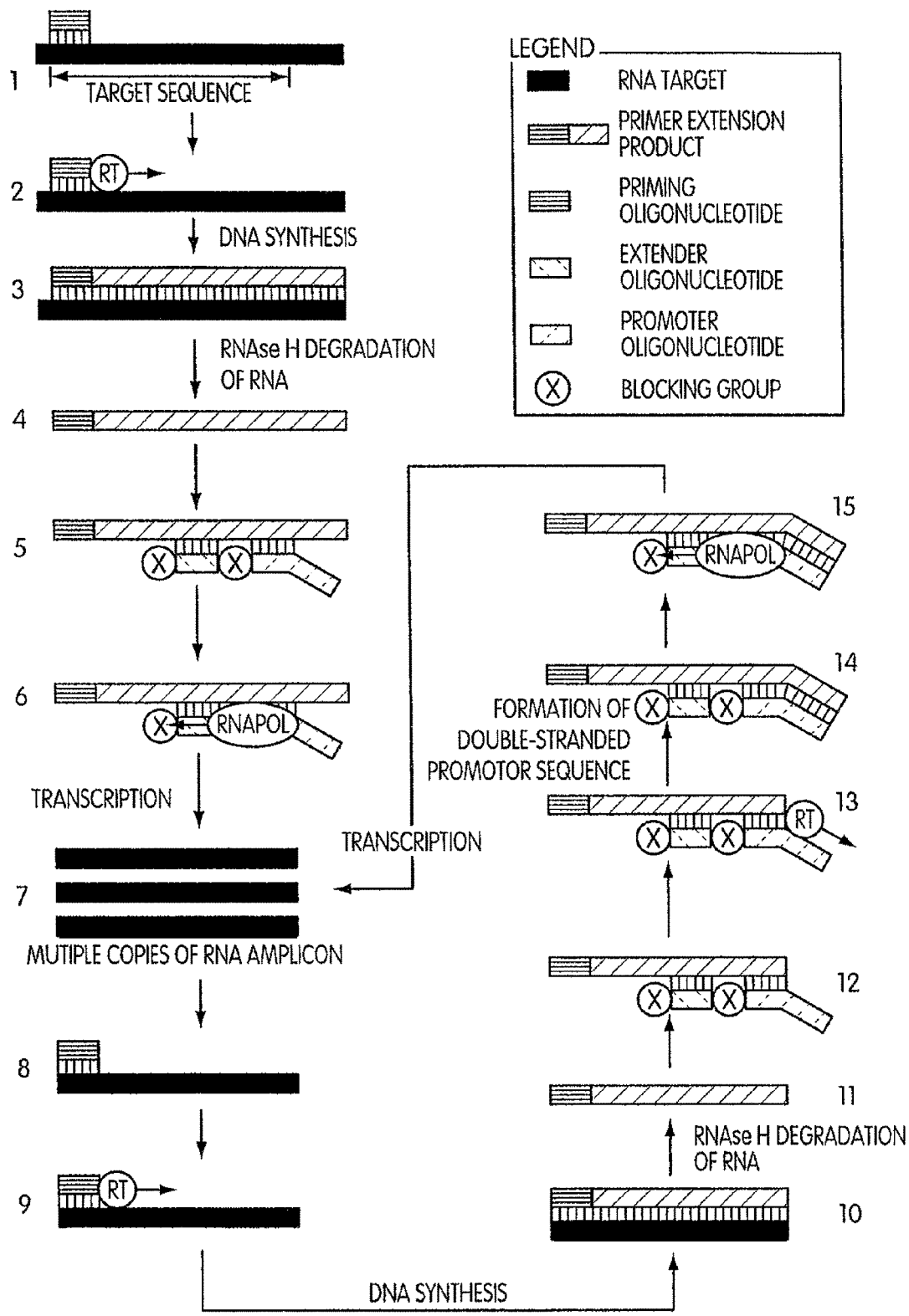
Figure 2C:
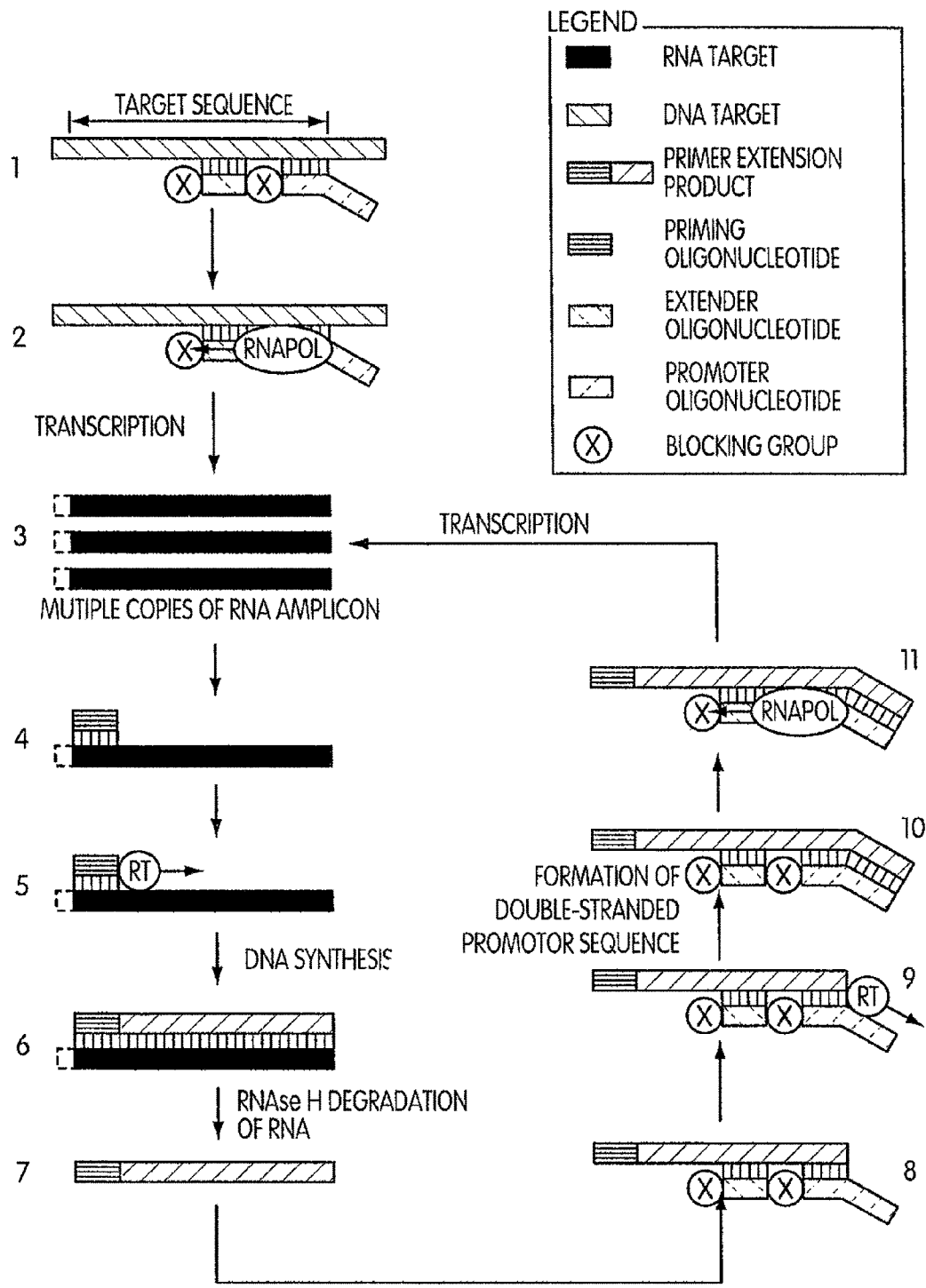
Figure 2D:
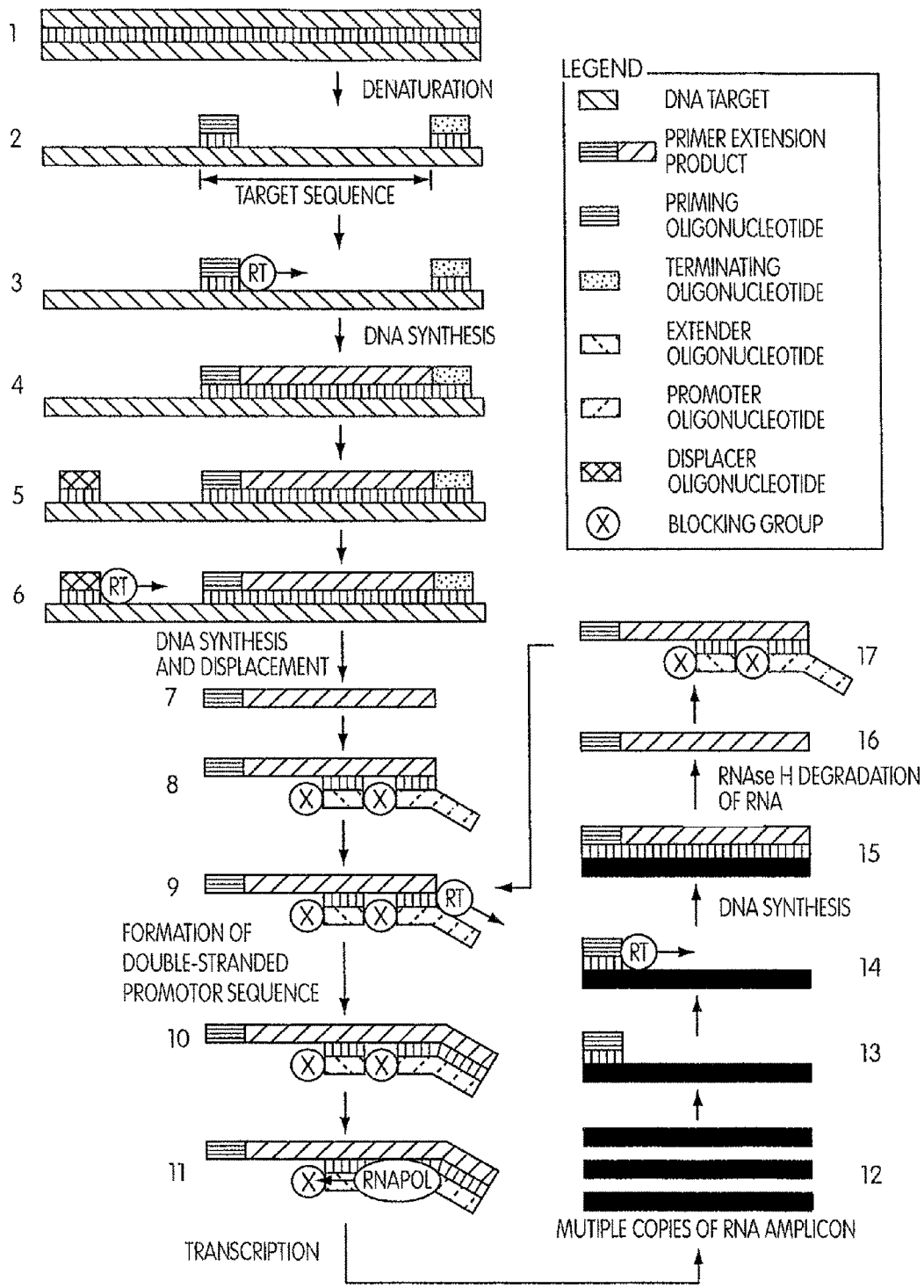

In yet another embodiment, the present invention relates to a method of synthesizing multiple copies of a target sequence from a target nucleic acid comprising a DNA target sequence. One aspect of this embodiment is illustrated in FIG. 1D. Prior to amplification, the target nucleic acid in this embodiment may be single-stranded, partially single-stranded, or double-stranded. If a region of the target nucleic acid containing the target sequence is double-stranded, then the target nucleic acid may be denatured, or partially denatured, prior to initiating amplification to render the target sequence accessible to the priming oligonucleotide. See Step 1 of FIG. 1D. Denaturation may be effected by heat, high pH, and/or low ionic strength. (Useful chemical denaturants include imidazole, dimethyl sulfoxide, formamide, urea and/or sodium hydryoxide.) The accessible target sequence is treated with a priming oligonucleotide, as described infra, which hybridizes to a 3'-end of the target sequence. See Step 2 of FIG. 1D. In the presence of nucleoside triphosphates and buffers, salts and cofactors, the 3'-end of the priming oligonucleotide is extended by a DNA polymerase in an extension reaction using the DNA target sequence as a template to give a first DNA primer extension product that is complementary to the template. See Steps 3 and 4 of FIG. 1D. In one aspect of this embodiment, a binding molecule is included which limits the length of the first DNA primer extension product by hybridizing or otherwise binding to the target nucleic acid adjacent to or near the 5'-end of the target sequence. The binding molecule may be any of the binding molecules described herein that is appropriate for a target nucleic acid containing a DNA target sequence, but is preferably a terminating oligonucleotide. See Steps 2 to 4 of FIG. 1D. One advantage of a terminating oligonucleotide is that it does not require the use of a restriction endonuclease to create a defined 3'-end on the first DNA primer extension product.

To separate the first DNA primer extension product from the template, the target nucleic acid can be treated with a displacer oligonucleotide in another aspect of this embodiment. See Step 5 of FIG. 1D. The displacer oligonucleotide has a priming function and is designed to hybridize to the target nucleic acid upstream from the priming oligonucleotide (referred to as the "forward priming oligonucleotide" in this embodiment). By "upstream" is meant that a 3'-end of the displacer oligonucleotide hybridizes to the target nucleic acid upstream from a 3'-end of the forward priming oligonucleotide. Thus, the displacer oligonucleotide and the forward priming oligonucleotide may hybridize to overlapping or distinct regions of the target nucleic acid. In preferred embodiments, the 3'-terminus of the displacer oligonucleotide is adjacent to or spaced up to 5 to 35 bases from the 5'-terminus of the forward priming oligonucleotide relative to the target nucleic acid (i.e., the target nucleic acid has up to 5 to 35, contiguous unbound nucleotides situated between the 3'-terminal base of the displacer oligonucleotide and the 5'-terminal base of the priming oligonucleotide when both oligonucleotides are hybridized to the target nucleic acid). The displacer oligonucleotide is generally from 10 to 50 nucleotides in length and may include one or more modifications at the 5'-end which improve the binding properties (e.g., hybridization or base stacking) of the displacer oligonucleotide to the target nucleic acid, provided that the modifications do not substantially interfere with the priming function of the displacer oligonucleotide. The displacer oligonucleotide and the forward priming oligonucleotide are designed to hybridize to the target nucleic acid under the same conditions. The target nucleic acid is preferably treated with the displacer oligonucleotide after the forward priming oligonucleotide has had sufficient time to hybridize to the target nucleic acid. Alternatively, the target nucleic acid is treated with both the displacer oligonucleotide and the forward priming oligonucleotide before exposing the mixture to a polymerase suitable for extending the 3'-ends of the displacer oligonucleotide and the forward priming oligonucleotide. In the presence of the DNA polymerase, the 3'-end of the displacer oligonucleotide is extended in a template-dependent manner to form a second DNA primer extension product which displaces the first DNA primer extension product from the target nucleic acid, thereby making it available for hybridization to a promoter oligonucleotide. See Steps 6 and 7 of FIG. 1D. In an alternative approach, conditions could be established whereby the promoter oligonucleotide gains access the first DNA primer extension product through stand invasion facilitated by, for example, DNA breathing (e.g., AT rich regions), low salt conditions, and/or the use of DMSO and/or osmolytes, such as betaine. The promoter oligonucleotide of this embodiment is the same as that described above and, likewise, is modified to prevent the promoter oligonucleotide from functioning as a priming oligonucleotide for a DNA polymerase (e.g., the promoter oligonucleotide includes a blocking moiety at its 3'-terminus).

Where a terminating oligonucleotide or other binding molecule capable of determining the 3'-end of the first DNA primer extension product is used, a first region of the promoter oligonucleotide is designed to hybridize to the 3'-end of the first DNA primer extension product with sufficient precision that a second region of the promoter oligonucleotide acts as a template, allowing the first DNA primer extension product to be further extended to add a base region complementary to the second region of the promoter oligonucleotide. See Steps 8-10 of FIG. 1D. This extension reaction renders a region containing the promoter sequence double-stranded. An RNA polymerase which recognizes the promoter then binds to the promoter sequence and initiates transcription of multiple RNA copies complementary to the first DNA primer extension product, where the RNA copies are substantially identical to the target sequence, as this term is defined hereinabove. See Steps 11 and 12 of FIG. 1D. The RNA transcripts so produced may automatically recycle in the method of this embodiment and, thus, the reaction is autocatalytic. See Steps 9-17 of FIG. 1D. In the subsequent rounds of amplification, a third DNA primer extension product comprising the promoter oligonucleotide and complementary to the RNA transcript is formed, and this DNA primer extension product is then separated from the RNA transcript (at least partially) using an enzyme which selectively degrades the RNA transcript (e.g., an enzyme having an RNase H activity, such as a reverse transcriptase derived from MMLV or AMV). See Steps 13-16 of FIG. 1D.

In those aspects of this embodiment where a binding molecule or other means for terminating a primer extension reaction are not used, the first region of the promoter oligonucleotide is designed to hybridize to a selected region of the first DNA primer extension product which is expected to be 5' to the 3'-terminus of the first DNA primer extension product. Since the 3'-terminus of the first DNA primer extension product is indeterminate, the region where the promoter oligonucleotide hybridizes probably will not be at the actual 3'-end of the first DNA primer extension product. According to this embodiment, it is generally the case that at least the 3'-terminal base of the first DNA primer extension product does not hybridize to the promoter oligonucleotide. Thus, according to this embodiment the first DNA primer extension product will likely not be further extended to form a double-stranded promoter. As discussed above, the inventors surprisingly discovered that the formation of a double-stranded promoter sequence through extension of a template nucleic acid is not necessary to permit initiation of transcription of RNA complementary to the first DNA primer extension product. In subsequent rounds of amplification, however, the RNA transcripts will include a defined 3'-end and DNA primer extension products complementary to the RNA transcripts will hybridize to the promoter oligonucleotide and be extended to add a sequence complementary to a region of the promoter oligonucleotide containing the promoter sequence.

The inventors also discovered that the rate of amplification could be enhanced by providing an extender oligonucleotide to a reaction mixture, as diagramed in FIGS. 2A-2D. (Step 5 of FIGS. 2A and 2B, Step 4 of FIG. 2C, and Step 8 of FIG. 2D.) An extender oligonucleotide is generally 10 to 50 nucleotides in length and hybridizes to a DNA template (i.e., the DNA target sequence or any of the DNA primer extension products described herein) downstream from a promoter oligonucleotide. When included, the 5'-terminal base of the extender oligonucleotide is positioned near or adjacent to the 3'-terminal base of the promoter oligonucleotide when both oligonucleotides are hybridized to a DNA template. (By "adjacent to" is meant that the DNA template has no unbound bases situated between the 3'-terminal base of the promoter oligonucleotide and the 5'-terminal base of the extender oligonucleotide when both oligonucleotides are hybridized to the DNA template.) Most preferably, the extender oligonucleotide hybridizes to a DNA template such that the 5'-terminal base of the extender oligonucleotide is spaced no more than three nucleotides from the 3'-terminal base of the promoter oligonucleotide relative to the DNA template (i.e., the DNA template has a maximum of three, contiguous unbound nucleotides situated between the 3'-terminal base of the promoter oligonucleotide and the 5'-terminal base of the extender oligonucleotide when both oligonucleotides are hybridized to the DNA template). To prevent the extender oligonucleotide from functioning as a priming oligonucleotide in a primer extension reaction, the extender oligonucleotide preferably includes a 3'-terminal blocking moiety. While not wishing to be bound by theory, it is believed that the phosphate at the 3'-end of the extender oligonucleotide functions to draw the DNA-dependent DNA polymerase (e.g., reverse transcriptase) farther away from the promoter sequence of the promoter oligonucleotide, thereby minimizing interference with the binding and progress of the RNA polymerase in transcription. It is also possible that the extender oligonucleotide facilitates faster transcription reactions by limiting secondary structure within the target sequence.

In one aspect, the present invention relates to minimizing side-product formation in nucleic acid amplification reactions. One type of side-product is referred to herein as an "oligonucleotide dimer." This side-product occurs when a priming oligonucleotide base-pairs non-specifically with another nucleic acid in the amplification reaction, e.g., the promoter oligonucleotide. Since the priming oligonucleotide can be extended via a DNA polymerase, a double-stranded form of the promoter oligonucleotide can result, which can be transcribed into non-specific, amplifiable side-products. To prevent priming oligonucleotides from participating in the formation of oligonucleotide dimers, one option is to add a short complementary nucleotide "cap" to the 3'-end of the priming oligonucleotide. See FIGS. 6A and 6B. A cap is thought to reduce non-specific hybridization between the priming oligonucleotide and other nucleic acids in the reaction, e.g., the promoter oligonucleotide, thereby eliminating or substantially reducing the production of "oligonucleotide-dimer" side-products as compared to amplification reactions carried out under identical conditions, but without the use of a cap. As used herein, a cap comprises a base region complementary to a region at the 3'-end of the priming oligonucleotide which is preferably pre-hybridized to the priming oligonucleotide prior to its introduction into an amplification reaction mixture. A suitable cap length will vary based on base content, stringency conditions, etc., but will typically hybridize to up to 3, 6, 9, 12, 15, 18, or 20 contiguous or non-contiguous nucleotides at the '3-end of the priming oligonucleotide. Suitable caps preferably range from 5 to 10 bases in length. The length of the complementary cap region is dependent on several variables, for example, the melting temperature of the double-stranded hybrid formed with the 3'-end of the priming oligonucleotide. In general, an efficient cap will specifically hybridize to a region at the 3'-end of the priming oligonucleotide more strongly than any non-specific reactions with other oligonucleotides present in the amplification reaction, but will be readily displaced in favor of specific hybridization of the priming oligonucleotide with the desired template. Exemplary caps comprise, or alternately consist essentially of, or alternately consist of an oligonucleotide from 5 to 7 bases in length which hybridizes to a region at the 3'-end of the priming oligonucleotide, such that the 5'-terminal base of the cap hybridizes to the 3'-terminal base of the priming oligonucleotide. Typically, a cap will hybridize to no more than 8, 9, or 10 nucleotides of a region at the 3'-end of the priming oligonucleotide.

Figure 6A:
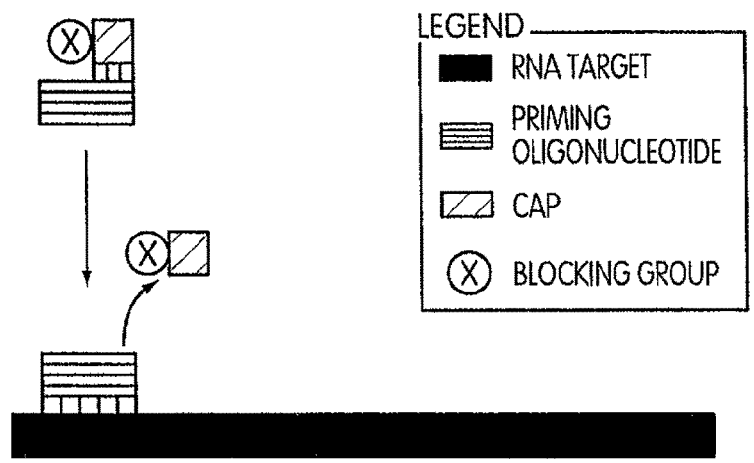
FIGS. 6A and 6B illustrate the use of caps to limit side-product formation. The cap and priming oligonucleotide are separate molecules in FIG. 6A, and in FIG. 6B they are linked to each other.
Figure 6B:
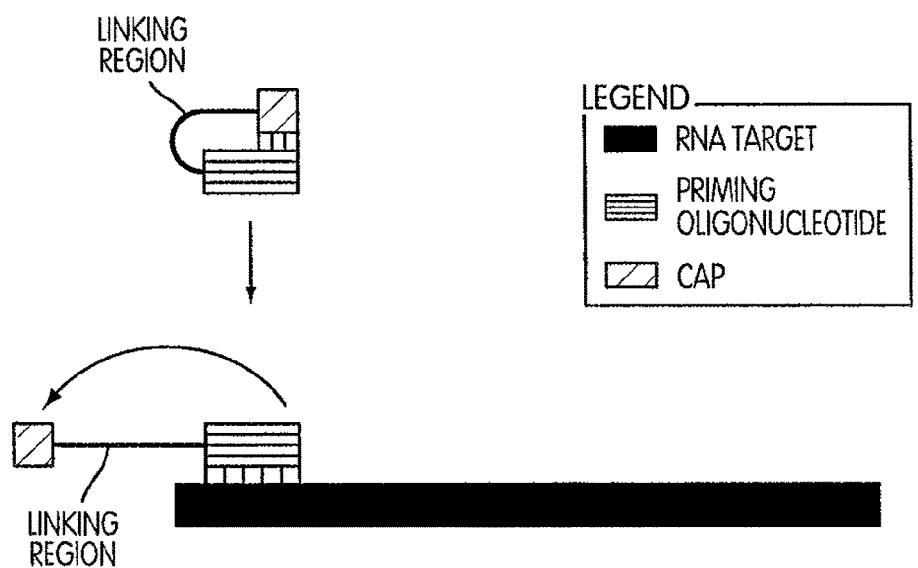

A cap may take the form of a capping oligonucleotide or a base region attached to the 5'-end of the priming oligonucleotide, either directly or through a linker. See FIGS. 6A and 6B. A capping oligonucleotide is synthesized as a separate oligonucleotide from the priming oligonucleotide, and normally comprises a blocking moiety at its 3'-terminus to prevent primer extension by a DNA polymerase, as illustrated in FIG. 6A. Alternatively, the cap comprises a base region complementary to a region at the 3'-end of the priming oligonucleotide, which is connected to the 5'-end of the priming oligonucleotide via a linking region comprising, alternately consisting essentially of, or alternately consisting of 3, 4, 5, 6, 7, 8, 9, or 10 nucleotides. See FIG. 6B. Typically, the nucleotides in the linking region are abasic nucleotides. By "abasic nucleotide" is meant a nucleotide comprising a phosphate group and a sugar group, but not a base group. Constructing a priming oligonucleotide with a cap attached to its 5'-end simplifies oligonucleotide synthesis by requiring the synthesis of only a single oligonucleotide comprising both the priming portion and the cap.

The caps described herein may also be used with other oligonucleotides provided to a reaction mixture, including displacer and extender oligonucleotides, which have free 3'-hydroxyls that are capable of participating in an extension reaction in the presence of a DNA polymerase. The importance of caps increases with the number of oligonucleotides having free 3'-hydroxyls.

In any of the embodiments described above, once a desired region for the target sequence is identified, that region can be analyzed to determine where selective RNAse degradation will optimally cause cuts or removal of sections of RNA from the RNA:DNA duplex. Analyses can be conducted to determine the effect of the RNAse degradation of the target sequence by RNAse H activity present in AMV reverse transcriptase or MMLV reverse transcriptase, by an exogenously added selective enzyme with an RNAse activity, e.g., $E.$ $coli$ RNAse H, or selective enzymes with an RNAse activity from other sources, and by combinations thereof. Following such analyses, the priming oligonucleotide can be selected for so that it will hybridize to a section of RNA which is substantially nondegraded by the selective RNAse present in the reaction mixture, because substantial degradation at the binding site for the priming oligonucleotide could inhibit initiation of DNA synthesis and prevent optimal extension of the primer. In other words, a priming oligonucleotide is typically selected to hybridize to a region of an RNA target nucleic acid or the complement of a DNA target nucleic acid, located so that when the RNA is subjected to selective RNAse degradation, there is no substantial degradation which would prevent formation of the primer extension product.

Conversely, the site for hybridization of the promoter oligonucleotide may be chosen so that sufficient degradation of the RNA strand occurs to permit efficient hybridization of the promoter oligonucleotide to the DNA strand. Typically, only portions of RNA are removed from the RNA:DNA duplex through selective RNAse degradation and, thus, some parts of the RNA strand will remain in the duplex. Selective RNAse degradation on the RNA strand of an RNA:DNA hybrid results in the dissociation of small pieces of RNA from the hybrid. Positions at which RNA is selectively degraded may be determined through standard hybridization analyses. Thus, a promoter oligonucleotide may be selected which will more efficiently bind to the DNA after selective RNAse degradation, i.e., will bind at areas where RNA fragments are selectively removed.

FIGS. 1A-1D and 2A-2D do not show the RNA portions which may remain after selective RNAse degradation. It is to be understood, however, that even though FIGS. 1A-1D and 2A-2D show complete removal of RNA from the DNA:RNA duplex, under certain conditions only partial removal actually occurs. Indeed, amplification as depicted in FIGS. 1A-1D and 2A-2D may be inhibited if a substantial portion of the RNA strand of an RNA:DNA hybrid remains undegraded, thus preventing hybridization of the promoter oligonucleotide and/or the optional extender oligonucleotide. However, based upon principles and methods disclosed in this application, as well as those disclosed by Kacian et al, U.S. Pat. No. 5,339,491, routine modifications can be made by those skilled in the art according to the teachings of this invention to provide an effective and efficient procedure for amplification of RNA.

In summary, the present invention provides methods for autocatalytically synthesizing multiple copies of a target sequence from a target nucleic acid without repetitive manipulation of reaction conditions such as temperature, ionic strength and pH, which comprises combining into a reaction mixture a target nucleic acid which comprises either an RNA target sequence, or a single-stranded or partially single-stranded DNA target sequence or a double-stranded DNA sequence which has been rendered at least partially single-stranded; a priming oligonucleotide, a promoter oligonucleotide, and, optionally, a displacer oligonucleotide, an extender oligonucleotide and/or a binding molecule or other means for terminating a primer extension reaction, all as described above; a reverse transcriptase or an RNA-dependent DNA polymerase and a DNA-dependent DNA polymerase; an enzyme activity which selectively degrades the RNA strand of an RNA:DNA complex (such as an RNAse H activity); and an RNA polymerase which recognizes the promoter sequence in the promoter oligonucleotide. The reaction mixture also includes the necessary building blocks for nucleic acid amplification, e.g., nucleoside triphosphates, buffers, salts, and stabilizing agents. The components of the reaction mixture may be combined stepwise or at once. The reaction mixture is incubated under conditions whereby an oligonucleotide:target nucleic acid is formed, and DNA priming and nucleic acid synthesis can occur for a period of time sufficient to allow multiple copies of the target sequence or its complement to be produced. The reaction advantageously takes place under conditions suitable for maintaining the stability of reaction components, such as the enzymes, and without requiring modification or manipulation of reaction conditions during the course of the amplification reaction. Accordingly, the reaction of some embodiments may take place under conditions that are substantially isothermal and include substantially constant ionic strength and pH.

As such, the amplification methods of the present invention do not require repeated denaturation steps to separate the RNA:DNA complexes produced upon extension of the priming oligonucleotide. A denaturation step would require manipulation of reaction conditions, such as by substantially increasing the temperature of the reaction mixture (generally from ambient temperature to a temperature between about 80° C. and about 105° C.), reducing its ionic strength (generally by 10× or more) or changing pH (usually increasing pH to 10 or greater). Such manipulations of the reaction conditions often deleteriously affect enzyme activities, requiring addition of additional enzyme and also necessitate further manipulations of the reaction mixture to return it to conditions suitable for further nucleic acid synthesis. In those embodiments where the target nucleic acid is double-stranded DNA, an initial denaturation step is often required. Denaturation may be carried out by altering temperature, ionic strength, and/or pH as described above, prior to adding the remaining components of the reaction mixture. Once the remaining components are added, no additional manipulations of the reaction mixture are needed.

The methods of the present invention are designed to decrease, diminish, or substantially eliminate side-product formation in the amplification reactions. For example, side-products are decreased, diminished, or substantially eliminated through the utilization of promoter oligonucleotides modified to prevent primer extension by a DNA polymerase, generally by including a blocking moiety at the 3'-termini of the promoter oligonucleotides. Further embodiments decrease, diminish, or substantially eliminate side-products through the use of a cap which hybridizes to a region at the 3'-end of the priming oligonucleotide, thereby preventing oligonucleotide dimer formation. According to the present invention, most, e.g., at least about 90%, of the oligonucleotides present in the amplification reaction which comprise a promoter further comprise a 3'-blocking moiety to prevent primer extension. In a specific embodiment, any oligonucleotide used in the amplification reaction which comprises a promoter, not just the promoter oligonucleotide, further comprises a 3'-blocking moiety. In certain preferred embodiments, most, e.g., at least about 80%, 90%, 95%, 96%, 97%, 98% or 99%, or all oligonucleotides required for the amplification reaction, other than the priming oligonucleotides (including displacer oligonucleotides, if used), comprise a 3'-blocking moiety. Thus, in certain embodiments, most if not all DNA polymerase activity in the amplification reactions is limited to the formation of DNA primer extension products which comprise the priming oligonucleotides.

Promoters or promoter sequences suitable for incorporation in promoter oligonucleotides used in the methods of the present invention are nucleic acid sequences (either naturally occurring, produced synthetically or a product of a restriction digest) that are specifically recognized by an RNA polymerase that recognizes and binds to that sequence and initiates the process of transcription, whereby RNA transcripts are produced. Typical, known and useful promoters include those which are recognized by certain bacteriophage polymerases, such as those from bacteriophage T3, T7, and SP6, and a promoter from *E. coli*. The sequence may optionally include nucleotide bases extending beyond the actual recognition site for the RNA polymerase which may impart added stability or susceptibility to degradation processes or increased transcription efficiency. Promoter sequences for which there is a known and available polymerase that is capable of recognizing the initiation sequence are particularly suitable to be employed.

Suitable DNA polymerases include reverse transcriptases. Particularly suitable DNA polymerases include AMV reverse transcriptase and MMLV reverse transcriptase. Some of the reverse transcriptases suitable for use in the methods of the present invention, such as AMV and MMLV reverse transcriptases, have an RNAse H activity. Indeed, according to certain embodiments of the present invention, the only selective RNAse activity in the amplification reaction is provided by the reverse transcriptase—no additional selective RNAse is added. However, in some situations it may also be useful to add an exogenous selective RNAse, such as *E. coli* RNAse H. Although the addition of an exogenous selective RNAse is not required, under certain conditions, the RNAse H activity present in, e.g., AMV reverse transcriptase may be inhibited or inactivated by other components present in the reaction mixture. In such situations, addition of an exogenous selective RNAse may be desirable. For example, where relatively large amounts of heterologous DNA are present in the reaction mixture, the native RNAse H activity of the AMV reverse transcriptase may be somewhat inhibited and thus the number of copies of the target sequence produced accordingly reduced. In situations where the target nucleic acid comprises only a small portion of the nucleic acid present (e.g., where the sample contains significant amounts of heterologous DNA and/or RNA), it is particularly useful to add an exogenous selective RNAse. See, e.g., Kacian et al, U.S. Pat. No. 5,399,491, the contents of which are hereby incorporated by reference herein (see Example 8).

RNA amplification products produced by the methods described above may serve as templates to produce additional amplification products related to the target sequence through the above-described mechanisms. The system is autocatalytic and amplification by the methods of the present invention occurs without the need for repeatedly modifying or changing reaction conditions such as temperature, pH, ionic strength and the like. These methods do not require an expensive thermal cycling apparatus, nor do they require several additions of enzymes or other reagents during the course of an amplification reaction.

The methods of the present invention are useful in assays for detecting and/or quantitating specific nucleic acid target sequences in clinical, environmental, forensic, and similar samples or to produce large numbers of RNA amplification products from a specific target sequence for a variety of uses. For example, the present invention is useful to screen clinical samples (e.g., blood, urine, feces, saliva, semen, or spinal fluid), food, water, laboratory and/or industrial samples for the presence of specific nucleic acids. The present invention can be used to detect the presence of, for example, viruses, bacteria, fungi, or parasites. The present invention is also useful for the detection of human, animal, or plant nucleic acids for genetic screening, or in criminal investigations, archeological or sociological studies.

In a typical assay, a sample containing a target nucleic acid to be amplified is mixed with a buffer concentrate containing the buffer, salts, magnesium, triphosphates, oligonucleotides, e.g., a priming oligonucleotide, a promoter oligonucleotide, and, optionally, a displacer oligonucleotide, an extender oligonucleotide and/or a binding molecule, e.g., a terminating oligonucleotide or a digestion oligonucleotide, and/or a capping oligonucleotide, and other reagents. The reaction may optionally be incubated at a temperature, e.g., 60-100° C., for a period of time sufficient to denature any secondary structures in the target nucleic acid or to denature a double-stranded DNA target nucleic acid. After cooling, reverse transcriptase, an RNA polymerase, and, if desired, a separate selective RNAse, e.g., RNAse H, are added and the reaction is incubated for a specified amount of time, e.g., from about 10 minutes to about 120 minutes, at an optimal temperature, e.g., from about 20° C. to about 55° C., or more, depending on the reagents and other reaction conditions. The displacer oligonucleotide, if used, may be provided with the enzymes to permit sufficient time for the priming oligonucleotide to hybridize to the target nucleic acid before initiating amplification.

The amplification product can be detected by hybridization with an optionally labeled detection probe and measurement of the resulting hybrids can be performed in any conventional manner. Design criteria in selecting probes for detecting particular target sequences are well known in the art and are described in, for example, Hogan et al., "Methods for Making Oligonucleotide Probes for the Detection and/or Quantitation of Non-Viral Organisms," U.S. Pat. No. 6,150,517, the contents of which are hereby incorporated by reference herein. Hogan teaches that probes should be designed to maximize homology for the target sequence(s) and minimize homology for possible non-target sequences. To minimize stability with non-target sequences, Hogan instructs that guanine and cytosine rich regions should be avoided, that the probe should span as many destabilizing mismatches as possible, and that the length of perfect complementarity to a non-target sequence should be minimized. Contrariwise, stability of the probe with the target sequence(s) should be maximized, adenine and thymine rich regions should be avoided, probe: target hybrids are preferably terminated with guanine and cytosine base pairs, extensive self-complementarity is generally to be avoided, and the melting temperature of probe: target hybrids should be about 2-10° C. higher than the assay temperature.

In particular, the amplification product can be assayed by the Hybridization Protection Assay ("HPA"), which involves hybridizing a chemiluminescent oligonucleotide probe to the target sequence, e.g., an acridinium ester-labeled ("AE") probe, selectively hydrolyzing the chemiluminescent label present on unhybridized probe, and measuring the chemiluminescence produced from the remaining probe in a luminometer. See, e.g., Arnold et al., "Homogenous Protection Assay," U.S. Pat. No. 5,283,174 and NORMAN C. NELSON ET AL., NONISOTOPIC PROBING, BLOTTING, AND SEQUENCING, ch. 17 (Larry J. Kricka ed., 2d ed. 1995), each of which is hereby incorporated by reference in its entirety. Particular methods of carrying out HPA using AE probes are disclosed in the Examples section hereinbelow.

In further embodiments, the present invention provides quantitative evaluation of the amplification process in real-time by methods described herein. Evaluation of an amplification process in "real-time" generally involves making periodic determinations of the amount of signal associated with probe:amplicon complexes in the reaction mixture during the amplification reaction, and the determined values are used to calculate the amount of target sequence initially present in the sample. There are a variety of methods for determining the amount of initial target sequence present in a sample based on real-time amplification. These include those disclosed by Light et al., "Method for Determining the Amount of an Analyte in a Sample," U.S. Patent Application Publication No. US 2006-0276972 (paragraphs 505 to 549); Lee et al., "Methods for Quantitative Analysis of a Nucleic Acid Amplification Reaction," U.S. Patent Application Publication No. US 2006-0286587; Carrick et al., "Method and Algorithm for Quantitating Polynucleotides," U.S. Patent Application Publication No. US 2006-0292619; Wittwer et al., "Method for Quantification of an Analyte," U.S. Pat. No. 6,303,305; and Yokoyama et al., "Method for Assaying Nucleic Acid," U.S. Pat. No. 6,541,205. (Each of these references or the indicated portion is hereby incorporated by reference herein.) Another method for determining the quantity of target sequence initially present in a sample, but which is not based on a real-time amplification, is disclosed by Ryder et al., "Method for Determining Pre-Amplification Levels of a Nucleic Acid Target Sequence from Post-Amplification Levels of Product," U.S. Pat. No. 5,710,029, the contents of which are hereby incorporated by reference herein. The present invention is particularly suited to real-time evaluation, because the production of side-products is decreased, diminished, or substantially eliminated.

Amplification products may be detected in real-time through the use of various self-hybridizing probes, most of which have a stem-loop structure. Such self-hybridizing probes are labeled so that they emit differently detectable signals, depending on whether the probes are in a self-hybridized state or an altered state through hybridization to a target sequence. By way of example, "molecular torches" are a type of self-hybridizing probe which includes distinct regions of self-complementarity (referred to as "the target binding domain" and "the target closing domain") which are connected by a joining region (e.g., non-nucleotide linker) and which hybridize to each other under predetermined hybridization assay conditions. In a preferred embodiment, molecular torches contain single-stranded base regions in the target binding domains that are from 1 to about 10 bases in length and are accessible for hybridization to a target sequence present in an amplification product under strand displacement conditions. The single-stranded region may be, for example, a terminal region or an internal region, such as a loop region. Alternatively, the strand displacement conditions may cause "breathing" in a double-stranded terminal region of the molecular torch, thereby resulting in a transient single-stranded region of the terminal region which is accessible for hybridization to the target sequence. Under strand displacement conditions, hybridization of the two complementary regions (which may be fully or partially complementary) of the molecular torch is favored, except in the presence of the target sequence, which will bind to the single-stranded region present in the target binding domain and displace all or a portion of the target closing domain. The target binding domain and the target closing domain of a molecular torch include a detectable label or a pair of interacting labels (e.g., luminescent/quencher) positioned so that a different signal is produced when the molecular torch is self-hybridized than when the molecular torch is hybridized to the target sequence, thereby permitting detection of probe:target duplexes in a test sample in the presence of unhybridized molecular torches. Molecular torches and a variety of types of interacting label pairs are disclosed by Becker et al., "Molecular Torches," U.S. Pat. No. 6,534,274, the contents of which are hereby incorporated by reference herein.

Another example of a detection probe exhibiting self-complementarity is a "molecular beacon." Molecular beacons include nucleic acid molecules having a target complement sequence, an affinity pair (or nucleic acid arms) holding the probe in a closed conformation in the absence of a target sequence present in an amplification product, and a label pair that interacts when the probe is in a closed conformation. Hybridization of the target sequence and the target complement sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Molecular beacons are disclosed by Tyagi et al., "Detectably Labeled Dual Confirmation Oligonucleotide Probes, Assays and Kits," U.S. Pat. No. 5,925,517, and Tyagi et al., "Nucleic Acid Detection Probes Having Non-FRET Fluorescence Quenching and Kits and Assays Including Such Probes," U.S. Pat. No. 6,150,097, each of which is hereby incorporated by reference herein in its entirety.

Other self-hybridizing probes for use in the present invention are well known to those of ordinary skill in the art. By way of example, probe binding pairs having interacting labels, such as those disclosed by Morrison, "Competitive Homogenous Assay," U.S. Pat. No. 5,928,862 (the contents of which are hereby incorporated by reference herein), might be adapted for use in the present invention. Probe systems used to detect single nucleotide polymorphisms (snps) might also be utilized in the present invention. Additional detection systems include "molecular switches," as disclosed by Arnold et al., "Oligonucleotides Comprising a Molecular Switch," U.S. Patent Application Publication No. US 2005-0042638, the contents of which are hereby incorporated by reference herein. And other probes, such as those comprising intercalating dyes and/or fluorochromes, might be useful for detection of amplification products in the present invention. See, e.g., Ishiguro et al., "Method of Detecting Specific Nucleic Acid Sequences," U.S. Pat. No. 5,814,447, the contents of which are hereby incorporated by reference herein.

In those methods of the present invention where the initial target sequence and the RNA transcription product share the same sense, it may be desirable to initiate amplification before adding probe for real-time detection. Adding probe prior to initiating an amplification reaction may slow the rate of amplification since probe which binds to the initial target sequence has to be displaced or otherwise remove during the primer extension step to complete a primer extension product having the complement of the target sequence. The initiation of amplification is judged by the addition of amplification enzymes (e.g., a reverse transcriptase and an RNA polymerase).

In addition to the methods described herein, the present invention is drawn to kits comprising one or more of the reagents required for carrying out the methods of the present invention. Kits comprising various components used in carrying out the present invention may be configured for use in any procedure requiring amplification of nucleic acid target molecules, and such kits can be customized for various different end-users. Suitable kits may be prepared, for example, for blood screening, disease diagnosis, infection control, environmental analysis, criminal investigations or other forensic analyses, genetic analyses, archeological or sociological analyses, or for general laboratory use. Kits of the present invention provide one or more of the components necessary to carry out nucleic acid amplifications according to the invention. Kits may include reagents suitable for amplifying nucleic acids from one particular target or may include reagents suitable for amplifying multiple targets. Kits of the present invention may further provide reagents for real-time detection of one or more nucleic acid targets in a single sample, for example, one or more self-hybridizing probes as described above. Kits may comprise a carrier that may be compartmentalized to receive in close confinement one or more containers such as vials, test tubes, wells, and the like. Preferably at least one of such containers contains one or more components or a mixture of components needed to perform the amplification methods of the present invention.

A kit according to the present invention can include, for example, in one or more containers, a priming oligonucleotide, a promoter oligonucleotide modified to prevent primer extension by a DNA polymerase (e.g., modified to include a 3'-blocking moiety), a binding molecule or other means for terminating a primer extension reaction, and, optionally, a displacer oligonucleotide, an extender oligonucleotide and/or a capping oligonucleotide as described herein. If real-time detection is used, the one or more containers may include one or more reagents for real-time detection of at least one nucleic acid target sequence in a single sample, for example, one or more self-hybridizing probes as described above. Another container may contain an enzyme reagent, for example a mixture of a reverse transcriptase (either with or without RNAse H activity), an RNA polymerase, and optionally an additional selective RNAse enzyme. (If included, the displacer oligonucleotide may be provided in the container containing the enzyme reagent.) These enzymes may be provided in concentrated form or at working concentration, usually in a form which promotes enzyme stability. The enzyme reagent may also be provided in a lyophilized form. See Shen et al., "Stabilized Enzyme Compositions for Nucleic Acid Amplification," U.S. Pat. No. 5,834,254, the contents of which are hereby incorporated by reference herein. Another one or more containers may contain an amplification reagent in concentrated form, e.g., 10×, 50×, or 100×, or at working concentration. An amplification reagent will contain one or more of the components necessary to run the amplification reaction, e.g., a buffer, $MgCl_2$, KCl, dNTPs, rNTPs, EDTA, stabilizing agents, etc. Certain of the components, e.g., $MgCl_2$ and rNTPs, may be provided separately from the remaining components, allowing the end user to titrate these reagents to achieve more optimized amplification reactions. Another one or more containers may include reagents for detection of amplification products, including one or more optionally labeled detection probes. In some embodiments, a kit of the present invention will also include one or more containers containing one or more positive and negative control target nucleic acids which can be utilized in amplification experiments in order to validate the test amplifications carried out by the end user. In some instances, one or more of the reagents listed above may be combined with an internal control. It is also possible to combine one or more of these reagents in a single tube or other containers.

Supports suitable for use with the invention (e.g., test tubes, multi-tube units, multi-well plates, cuvettes, flexible containers, microfluidic devices, including analytical cards or discs for use in centrifugal analyzers, etc.) may also be supplied with reagents of the invention. Finally, a kit of the present invention may include one or more instruction manuals provided in written or electronic form, including CD-ROMs, DVDs and video tapes. Kits of the invention may contain virtually any combination of the components set out above or described elsewhere herein. As one skilled in the art would recognize, the components supplied with kits of the invention will vary with the intended use for the kits, and the intended end user. Thus, kits may be specifically designed to perform various functions set out in this application and the components of such kits will vary accordingly.

The present invention is further drawn to various oligonucleotides, including the priming oligonucleotides, promoter oligonucleotides, terminating oligonucleotides, displacer oligonucleotides, extender oligonucleotides, capping oligonucleotides and detection probes described herein. It is to be understood that the oligonucleotides of the present invention may be DNA, RNA, DNA:RNA chimerics and analogs thereof, and, in any case, the present invention includes RNA equivalents of DNA oligonucleotides and DNA equivalents of RNA oligonucleotides. Except for the preferred priming oligonucleotides (including displacer oligonucleotides) and detection probes described supra, the oligonucleotides described hereinabove preferably comprise a blocking moiety at their 3'-termini.

Detection probes of the present invention may be labeled in a number of alternative ways, e.g., with radioactive isotopes, fluorescent labels, chemiluminescent labels, nuclear tags, bioluminescent labels, intercalating dyes, or enzyme labels. The detection probes may include groups of interacting labels which emit a detectable change in signal when the probes are hybridized to a target sequence or its complement. In various embodiments, these labeled probes optionally or preferably are synthesized to include at least one modified nucleotide, e.g., a 2'-O-methyl ribonucleotide; or these labeled oligonucleotide probes optionally or preferably are synthesized entirely of modified nucleotides, e.g., 2'-O-methyl ribonucleotides.

It will be understood by one of ordinary skill in the relevant arts that other suitable modifications and adaptations to the methods and compositions described herein are readily apparent from the description of the invention contained herein in view of information known to the ordinarily skilled artisan, and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Examples are provided below illustrating different aspects and embodiments of the invention. It is believed that these examples accurately reflect the details of experiments actually performed, however, it is possible that some minor discrepancies may exist between the work actually performed and the experimental details set forth below which do not affect the conclusions of these experiments. Skilled artisans will appreciate that these examples are not intended to limit the invention to the specific embodiments described therein. Additionally, those skilled in the art, using the techniques, materials and methods described herein, could easily devise and optimize alternative amplification systems for detecting and/or quantifying any target sequence.

The practice of the present invention will employ, unless otherwise indicated, conventional techniques of molecular biology, recombinant DNA, and chemistry, which are within the skill of the art. Such techniques are explained fully in the literature. See, for example, *Molecular Cloning A Laboratory Manual*, 2nd Ed., Sambrook et al., ed., Cold Spring Harbor Laboratory Press: (1989); *DNA Cloning*, Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); B. Perbal, *A Practical Guide To Molecular Cloning* (1984); the treatise, *Methods In Enzymology* (Academic Press, Inc., N.Y.); and in Ausubel et al., *Current Protocols in Molecular Biology*, John Wiley and Sons, Baltimore, Md. (1989).

Unless otherwise indicated, oligonucleotides and modified oligonucleotides in the following examples were synthesized using standard phosphoramidite chemistry, various methods of which are well known in the art. See e.g., Carruthers, et al., 154 Methods in Enzymology, 287 (1987), the contents of which are hereby incorporated by reference herein. Unless otherwise stated herein, modified nucleotides were 2'-O-methyl ribonucleotides, which were used in the synthesis as their phosphoramidite analogs. Applicant prepared the oligonucleotides using an Expedite™ 8909 DNA Synthesizer (PerSeptive Biosystems, Framingham, Mass.).

Various reagents are identified in the examples below, which include an amplification reagent, an enzyme reagent, a hybridization reagent, a selection reagent, and detection reagents. Unless otherwise indicated, the formulations and pH values (where relevant) of these reagents were as follows.

Amplification Reagent. The "Amplification Reagent" comprised 11.6 mM Trizma® base buffer, 15 mM Trizma® hydrochloride buffer, 22.7 mM $MgCl_2$, 23.3 mM KCl, 3.33% (v/v) glycerol, 0.05 mM zinc acetate, 0.665 mM dATP, 0.665 mM dCTP, 0.665 mM dGTP, 0.665 mM dTTP, 0.02% (v/v) ProClin 300 Preservative (Supelco, Bellefonte, Pa.; Cat. No. 48126), 5.32 mM ATP, 5.32 mM CTP, 5.32 mM GTP, 5.32 mM UTP, and 6 M HCl to pH 7.81 to 8.0 at 22° C.

Enzyme Reagent. The "Enzyme Reagent" comprised 70 mM N-acetyl-L-cysteine, 10% (v/v) TRITON® X-102 detergent, 16 mM HEPES, 3 mM EDTA, 0.05% (w/v) sodium azide, 20 mM Trizma® base buffer, 50 mM KCl, 20% (v/v) glycerol, 150 mM trehalose, 4M NaOH to pH 7, and containing 224 RTU/µL Moloney murine leukemia virus ("MMLV") reverse transcriptase and 140 U/µL T7 RNA polymerase, where one RTU of RT activity incorporates 1 nmol of dTMP into DE81 filter-bound product in 20 minutes at 37° C. using poly(rA)-p(dT)$_{12-18}$ as the substrate, and one U of T7 RNA polymerase activity produces 5 fmol of RNA transcript in 20 minutes at 37° C.

Hybridization Reagent. The "Hybridization Reagent" comprised 100 mM succinic acid, 2% (w/v) lithium lauryl sulfate, 230 mM LiOH, 15 mM aldrithiol-2, 1.2 M LiCl, 20 mM EDTA, 20 mM EGTA, 3.0% (v/v) ethyl alcohol, and 2M LiOH to pH 4.7.

Selection Reagent. The "Selection Reagent" comprised 600 mM $H_3BO_3$, 182 mM NaOH, 1% (v/v) TRITON® X-100 detergent, and 4 M NaOH to pH 8.5.

Detection Reagent I. "Detection Reagent I" comprised 1 mM $HNO_3$ and 30 mM $H_2O_2$.

Detection Reagent II. "Detection Reagent II" comprised 1 M NaOH and 2% (w/v) Zwittergent® 3-14 detergent.

Oil Reagent: The "Oil Reagent" comprised a silicone oil (United Chemical Technologies, Inc., Bristol, Pa.; Cat. No. PS038).

Example 1

Comparison of Blocked and Unblocked Promoter Oligonucleotides

This experiment was conducted to evaluate the specificity of an amplification method according to the present invention in which a region ("the target region") of a cloned transcript derived from the 5' untranslated region of the hepatitis C virus ("the transcript") was targeted for amplification. For this experiment we prepared two sets of priming and promoter oligonucleotides having identical base sequences. The two sets of oligonucleotides differed by the presence or absence of a 3'-terminal blocking moiety on the promoter oligonucleotide. The promoter oligonucleotide in each set targeted the complement of a sequence contained within the 5'-end of the target region and had the base sequence of SEQ ID NO:5 aatttaatacgactcactatagggagactagccatg gcgttagtatgagtgtcgtg-cag, where the underlined portion of the promoter oligonucleotide constitutes a T'7 promoter sequence (SEQ ID NO:3) and the non-underlined portion represents a hybridizing sequence (SEQ ID NO:4). The priming oligonucleotide in each set targeted a sequence contained within the 3'-end of the target region and had the base sequence of SEQ ID NO:6. Also included in the amplification method was a terminating oligonucleotide made up of 2'-O-methyl ribonucleotides having the base sequence of SEQ ID NO:38 ggcuagacgcuuu-cugcgugaaga. The terminating oligonucleotide had a 3'-terminal blocking moiety and targeted a region of the transcript just 5' to the target region. The 5'-ends of the terminating oligonucleotide and of the hybridizing sequence of the promoter oligonucleotide overlapped by six bases. The 3'-terminal blocking moiety of both the promoter oligonucleotide and the terminating oligonucleotide consisted of a 3'-to-3' linkage prepared using 3'-dimethyltrityl-N-benzoyl-2'-deoxycytidine, 5'-succinoyl-long chain alkylamino-CPG (Glen Research Corporation, Sterling, Va.; Cat. No. 20-0102-01).

For amplification, 75 µL of the Amplification Reagent was added to each of eight reaction tubes. The Amplification Reagent was then combined with 30 pmol of a promoter oligonucleotide, 30 pmol of the priming oligonucleotide and 5 pmol of the terminating oligonucleotide. One set of four of the tubes was provided with 30 pmol of the unblocked promoter oligonucleotide (group I), and another set of four tubes was provided with 30 pmol of the blocked promoter oligonucleotide (group II). Next, 1 µL of a 0.1% (w/v) lithium lauryl sulfate ("LLS") buffer containing 1000 copies/µL of the transcript was added to two of the tubes in each group, while the remaining two tubes in each group served as negative controls. The reaction mixtures were overlaid with 200 µL of the Oil Reagent, and the tubes were then sealed and hand-shaken horizontally for 5 to 10 seconds before the tubes were incubated in a 60° C. water bath for 10 minutes. The tubes were then transferred to a 41.5° C. water bath and incubated for 15 minutes before adding 25 µL of the Enzyme Reagent to each tube. After adding the Enzyme Reagent, the tubes were sealed, removed from the water bath and hand-shaken horizontally for 5 to 10 seconds to fully mix the components of the reaction mixtures. The tubes were returned to the 41.5° C. water bath and incubated for an additional 60 minutes to facilitate amplification of the target region in the presence of MMLV reverse transcriptase and T7 RNA polymerase. Following amplification, the tubes were removed from the 41.5° C. water bath and allowed to cool at room temperature for 10 to 15 minutes.

A 5 μL aliquot of each reaction mixture was taken from the tubes, diluted 1:1 with a 2×Novex® TBE-Urea Sample Buffer (Invitrogen Corporation, Carlsbad, Calif.; Cat. No. LC6876), and loaded onto a Novex® TBE-Urea Denaturing Gel (Invitrogen; Cat. No. EC6865BOX). The gel was held by an Xcell Surelock™ Mini-Cell (Invitrogen; Cat. No. EI0001) and run at 180 volts for 50 minutes using a 5× Novex® TBE Running Buffer (Invitrogen; Cat. No. LC6675) diluted 1:4 with deionized water. Afterwards, the gel was stained with 0.5 μg/mL of ethidium bromide in a 1×TBE (Tris-Borate-EDTA) solution, visualized on a FisherBiotech® Ultraviolet Transilluminator (Fisher Scientific International Inc., Hampton, N.H.; Model No. FB-TIV-816A), and photographed with a handheld camera using Polaroid 667 film.

Figure 3:
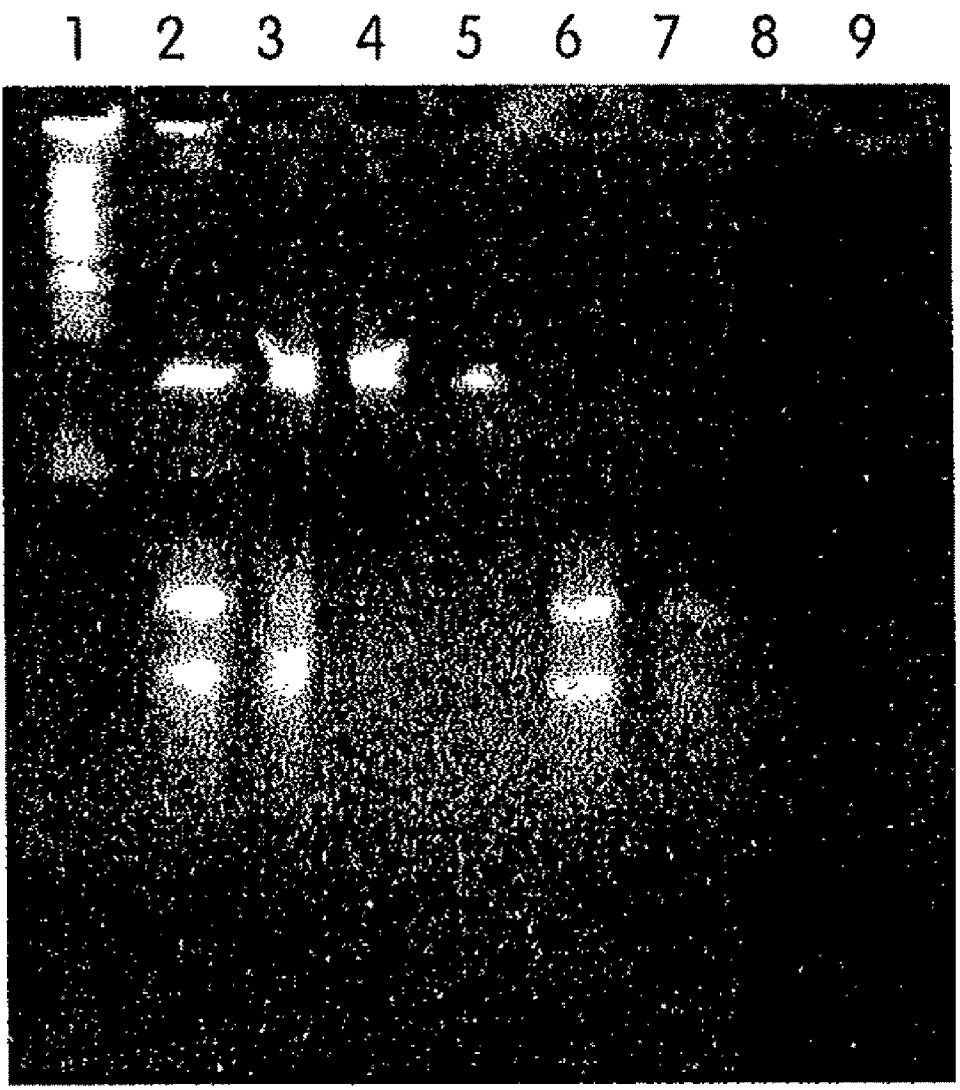
FIG. 3 depicts a denaturing agarose gel showing the effect of using a promoter oligonucleotide with a 3'-blocking moiety.
Figure 4A:
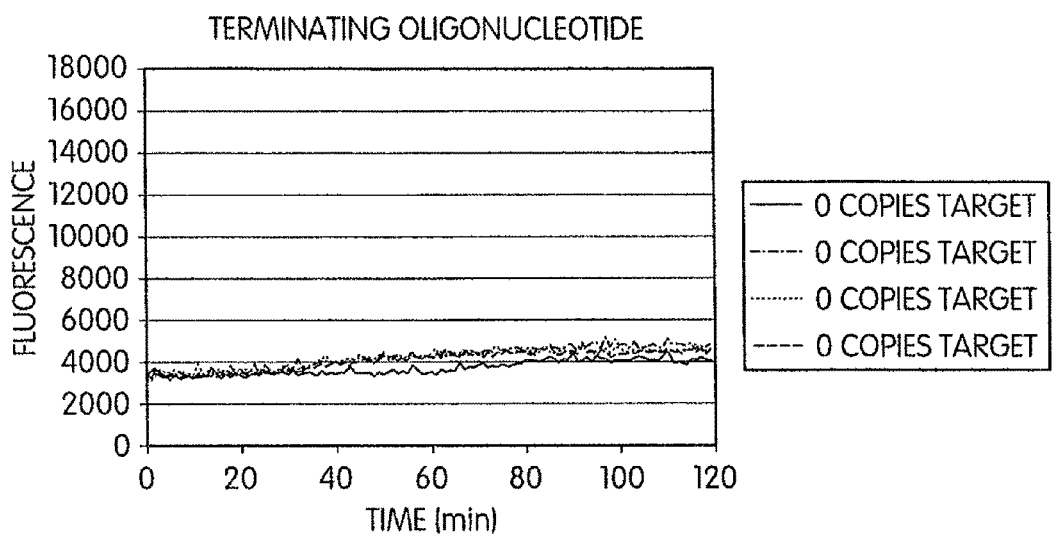
FIG. 4 shows the real-time accumulation of amplification products in a *Mycobacterium tuberculosis* system, both in the presence (FIGS. 4A, 4C and 4E) and in the absence (FIGS. 4B, 4D and 4F) of a terminating oligonucleotide modified to fully contain 2'-O-methyl ribonucleotides. The input target nucleic acid for these reactions was 0 copies (FIGS. 4A and 4B), 100 copies (FIGS. 4C and 4D) and 1000 copies (FIGS. 4E and 4F).
Figure 4B:
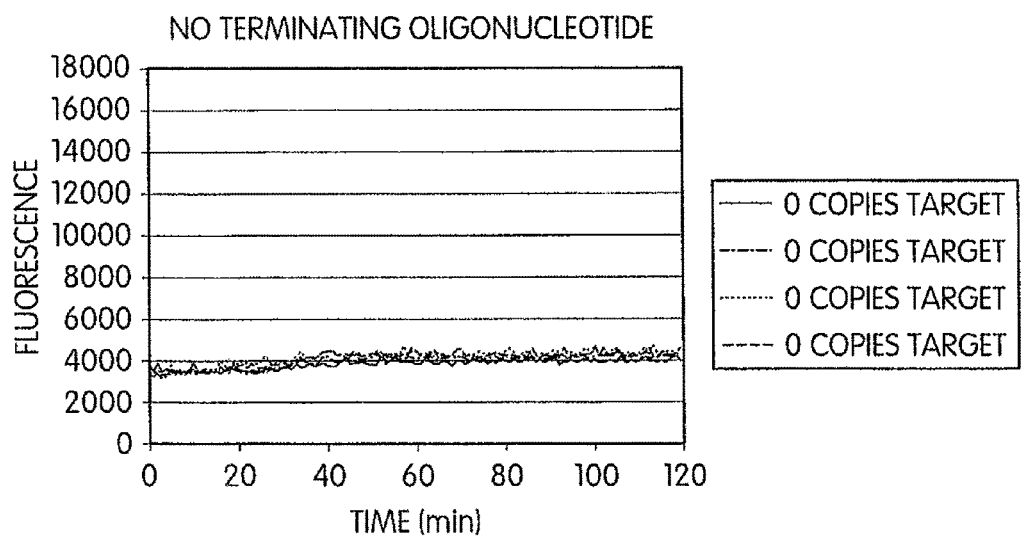
Figure 4C:
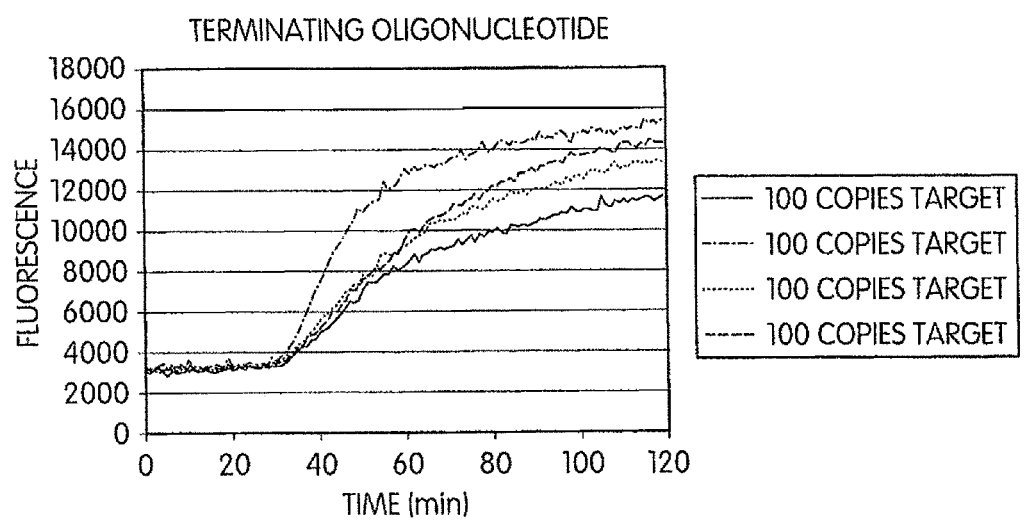
Figure 4D:
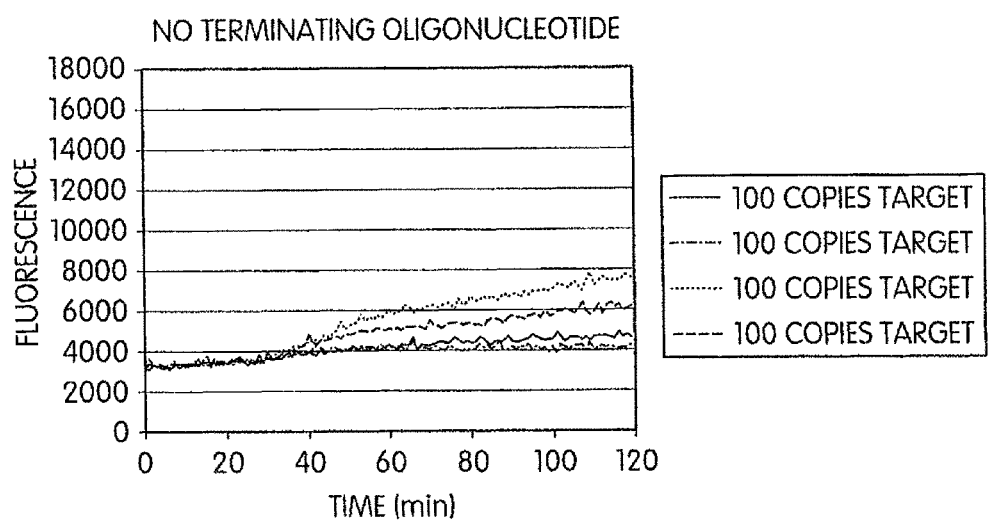
Figure 4E:
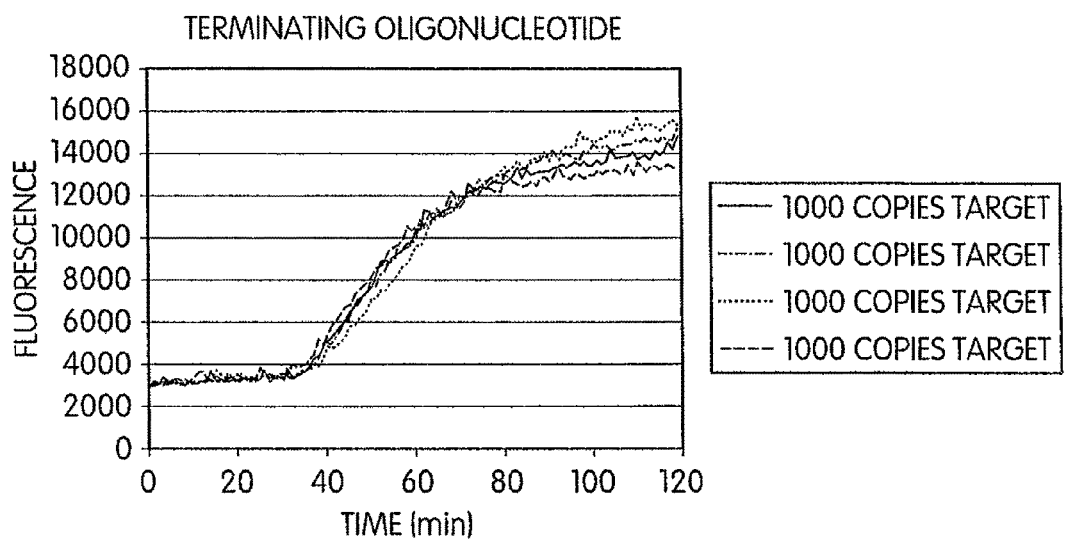
Figure 4F:
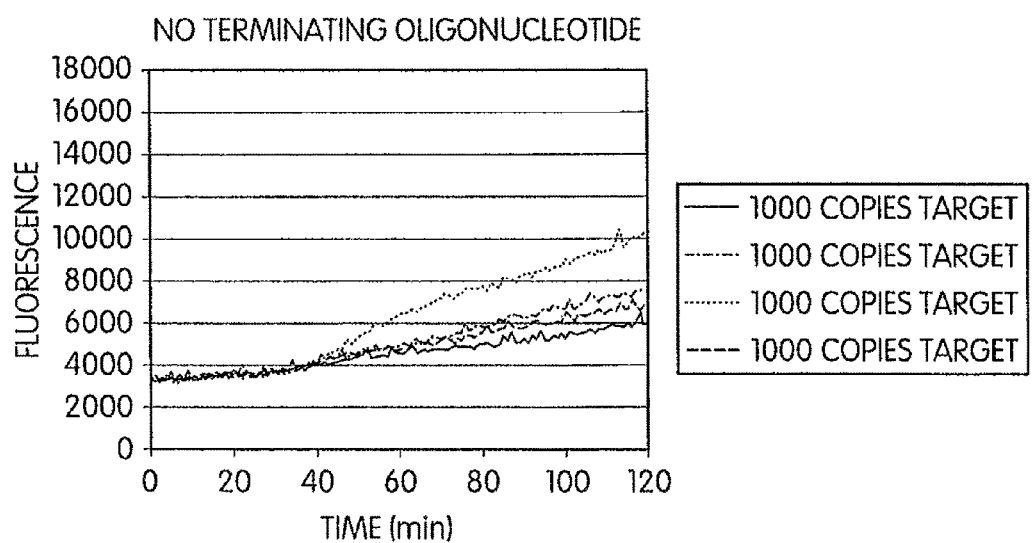

The results of this experiment are illustrated in the photographed gel of FIG. 3. Each number above the pictured gel represents a distinct lane, where lane 1 is an RNA ladder of 100, 200, 300, 400, 500, 750 and 1000 base oligonucleotides, and the remainder of the lanes correspond to the following reaction mixtures: (i) lanes 2 and 3 correspond to the transcript-containing replicates of group I (unblocked promoter oligonucleotide); (ii) lanes 4 and 5 correspond to the transcript-containing replicates of group II (blocked promoter oligonucleotide); (iii) lanes 6 and 7 correspond to the transcript-negative replicates of group I; and (iv) lanes 8 and 9 correspond to the transcript-negative replicates of group II. The first visible band in lanes 2-5 constitutes amplicon derived from amplification of the target region. The remainder of the bands in lanes 2, 3, 6 and 7 constitute non-specific amplification products. Thus, the results indicate that only amplification using the fully blocked promoter oligonucleotides was specific, as there was no visible side-product formation in either the transcript-containing or transcript negative reaction mixtures containing blocked promoter oligonucleotides, whereas visible side-products were formed in both the transcript-containing and transcript-negative reaction mixtures containing unblocked promoter oligonucleotides.

Example 2

Reduction in the Formation of Replicating Molecules

This experiment was designed to evaluate whether the use of a blocked promoter oligonucleotide in an amplification method of the present invention would lead to a reduction in the formation of replicating molecules over a standard transcription-based amplification procedure. Replicating molecules are generally believed to form when the 3'-end of a promoter oligonucleotide forms a hairpin structure and is extended in the presence of a polymerase, thereby forming a double-stranded promoter sequence. Transcription initiated from the double-stranded promoter sequence results in the formation of amplicon containing an antisense version of the promoter sequence.

In this experiment, we compared the production of replicating molecules in amplification reactions containing promoter oligonucleotides that were either blocked or unblocked at their 3'-terminal ends in the presence or absence of purified rRNA from *Mycobacterium tuberculosis* (ATCC No. 25177) using one of two detection probes targeting a region ("the target region") of the 16S rRNA of *Mycobacterium tuberculosis* ("the target nucleic acid"). The blocked and unblocked promoter oligonucleotides targeted sequences contained within the complement of the 5'-end of the target region. The blocked promoter oligonucleotide had the base sequence of SEQ ID NO:26 <u>aattctaatacgactcactatagggaga</u> actgggtctaatac-cggataggaccacgggatgcat, and the unblocked promoter oligonucleotide had the base sequence of SEQ ID NO:28 <u>aattctaatacgactcactatagggagaactgggtctaat</u> accggataggac-cacggga, where the underlined portion of each promoter oligonucleotide constitutes a T7 promoter sequence (SEQ ID NO:3) and the non-underlined portion represents a hybridizing sequence (SEQ ID NO:25 and SEQ ID NO:27). The priming oligonucleotide targeted a sequence contained within the 3'-end of the target region and had the base sequence of SEQ ID NO:29. Also included was a terminating oligonucleotide made up of 2'-O-methyl ribonucleotides having the base sequence of SEQ ID NO:39 cccaguuucccaggcu-uauccc. The terminating oligonucleotide targeted a region of the target nucleic acid just 5' to the target region and had a 3'-terminal blocking moiety. The 5'-ends of the terminating oligonucleotide and the hybridizing sequence of the promoter oligonucleotide overlapped by six bases. The 3'-terminal blocking moiety of both the blocked promoter oligonucleotide and the terminating oligonucleotide consisted of the 3'-to-3' linkage described in Example 1. And for detection, two detection probes were synthesized. The first detection probe ("detection probe I") comprised 2'-O-methyl ribonucleotides targeted a sequence contained within the target region and had the base sequence of SEQ ID NO:30 gcucauccca*caccgcuaaagc. The second detection probe ("detection probe II") targeted the antisense of a region contained within the T7 promoter sequence and had the base sequence of SEQ ID NO:40 atacgactc*actata. The asterisk in both detection probe sequences indicates the position of a 4-(2-succinimidyloxycarbonyl ethyl)-phenyl-10-methylacridinium-9-carboxylate fluorosulfonate acridinium ester label ("standard AE") joined to the probe by means of a non-nucleotide linker, as described by Arnold et al., "Linking Reagents for Nucleotide Probes," U.S. Pat. No. 5,585,481, the contents of which are hereby incorporated by reference herein.

A total of eight different amplification reactions were performed in replicates of five. All of the reaction tubes used for the amplification reactions were provided with 75 μL of the Amplification Reagent, followed by 5 pmol each of either the blocked or unblocked promoter oligonucleotide, the priming oligonucleotide, and the terminating oligonucleotide. Two sets of the tubes received 2 μL each of a 0.2% (w/v) LLS buffer containing 250 copies/μL of the target nucleic acid, and the other two sets of tubes received no target nucleic acid. The reaction mixtures were overlaid with 200 μL of the Oil Reagent, and the tubes were then sealed and hand-shaken horizontally for 5 to 10 seconds before being incubated in a 60° C. water bath for 10 minutes. The tubes were then transferred to a 41.5° C. water bath and incubated for 10 minutes before adding 25 μL of the Enzyme Reagent to each tube. After adding the Enzyme Reagent, the tubes were sealed, removed from the water bath and hand-shaken horizontally for 5 to 10 seconds to fully mix the components of the reaction mixtures. The tubes were returned to the 41.5° C. water bath and incubated for an additional 60 minutes to permit amplification of the target sequences. Following amplification, the tubes were removed from the 41.5° C. water bath and allowed to cool at room temperature for 10 to 15 minutes.

The detection step was performed in accordance with the Hybridization Protection Assay disclosed by Arnold et al., "Homogenous Protection Assay," U.S. Pat. No. 5,283,174. In this step, 100 μL of the Hybridization Reagent containing either 52 fmol of detection probe I or 10.2 fmol of detection probe II was added to each tube. After adding the detection probes, the tubes were sealed, hand-shaken horizontally for 5 to 10 seconds, and incubated in a 60° C. water bath for 15 minutes to permit hybridization of the detection probes to their corresponding target sequences. Following hybridization, 250 μL at of the Selection Reagent was added to the tubes and the tubes were sealed and hand-shaken horizontally for 5 to 10 seconds before being incubated in a 60° C. water bath for 10 minutes to hydrolyze acridinium ester labels associated with unhybridized probe. The samples were cooled at room temperature for at least 10 minutes before being analyzed in a LEADER® HC+ Luminometer (Gen-Probe Incorporated, San Diego, Calif.; Cat. No. 4747) equipped with automatic injection of Detection Reagent I, followed by automatic injection of Detection Reagent II. Signal emitted from the tubes was measured in relative light units ("RLU"), which is a measure of chemiluminescence.

The results were averaged for each set of reaction conditions and are presented in Table 1 below. From these results, it can be seen that those amplification reactions containing the blocked promoter oligonucleotide performed as well as those amplification reactions containing the unblocked promoter oligonucleotide at amplifying a targeted region of the target nucleic acid. However, those amplification reactions containing the blocked promoter oligonucleotide produced substantially fewer replicating molecules than did those amplification reactions containing the unblocked promoter oligonucleotide, both in the presence and in the absence of the transcript.

TABLE 1

Effect of 3'-Blocking Promoter Oligonucleotides on the Formation of Replicating Molecules

|  | Detection Probe I | | Detection Probe II | |
|---|---|---|---|---|
|  | No Target Nucleic Acid | Target Nucleic Acid | Target Nucleic Acid | No Target Nucleic Acid |
| Blocked Promoter Oligonucleotide | 1,047,084 | 4,222 | 64,874 | 10,063 |
| Unblocked Promoter Oligonucleotide | 976,156 | 98,067 | 526,657 | 456,130 |

Example 3

Sensitivity of Amplification Assay Using Blocked Promoter Oligonucleotide and Terminating Oligonucleotide This experiment examined the sensitivity of an amplification system according to the present invention in which a region ("the target region") of purified 23S rRNA from *Chlamydia trachomatis* (ATCC No. VR-878) ("the target nucleic acid") was targeted for amplification. Included in this experiment was a promoter oligonucleotide having a 3'-terminal blocking moiety, a priming oligonucleotide, a terminating oligonucleotide having a 3'-terminal blocking moiety, and a labeled detection probe. The promoter oligonucleotide targeted the complement of a sequence contained within the 5'-end of the target region and had the base sequence of SEQ ID NO:22 <u>aatttaatacgactcactatag</u>ggagacggagtaagttaag-cacgcggac gattgga, where the underlined portion of the promoter oligonucleotide constitutes a T7 promoter sequence (SEQ ID NO:3) and the non-underlined portion represents a hybridizing sequence (SEQ ID NO:21). The priming oligonucleotide targeted a sequence contained within the 3'-end of the target region and had the base sequence of SEQ ID NO:23. The terminating oligonucleotide was made up of 2'-O-methyl ribonucleotides having the base sequence of SEQ ID NO:41 uccgucauuccuucgcuauagu and targeted a region of the target nucleic acid just 5' to the target region. The 5'-ends of the terminating oligonucleotide and the hybridizing sequence of the promoter oligonucleotide overlapped by four bases. The 3'-terminal blocking moiety of both the promoter oligonucleotide and the terminating oligonucleotide consisted of the 3'-to-3' linkage described in Example 1. The detection probe targeted a sequence contained within the target region and was made up of 2'-O-methyl ribonucleotides having the base sequence of SEQ ID NO:24 cguucucaucgcucu*acggacucu, where the asterisk indicates the position of a standard AE label joined to the probe by means of a non-nucleotide linker. See Arnold et al., U.S. Pat. No. 5,585,481.

Amplification in this experiment was carried out essentially as described in Example 1. Each amplification reaction was performed in replicates of 3, and the target nucleic acid was added to each reaction tube in each set of replicates in copy numbers of 10, 100, 1000 or 10,000 from a 0.1% (w/v) LLS buffer containing 10, 100, 1000 or 10,000 copies/μL, respectively. The promoter and priming oligonucleotides were each added to the tubes in 30 pmol/reaction amounts, and 5 pmol of the terminating oligonucleotide was added to each tube. Using the *Chlamydia trachomatis* probe of this experiment, detection was carried out essentially as described in Example 2. The results of this experiment are set forth in Table 2 below and indicate 100 copy sensitivity for this amplification system, where an average RLU value of above 10,000 constituted a positive result.

TABLE 2

Sensitivity of *Chlamydia trachomatis* Amplification System

| Copy Number | Avg. RLU |
|---|---|
| 10 | 8504 |
| 100 | 51,574 |
| 1000 | 1,578,416 |
| 10,000 | 6,092,697 |

Example 4

Amplification of a Double-Stranded Target Sequence

This example examines an amplification system according to the present invention in which a region ("the target region") of a cloned, double-stranded transcript derived from the E6 and E7 genes of human papilloma virus type 16 ("HPV-16") ("the transcript") was targeted for amplification. See FIG. 1C. This experiment included a promoter oligonucleotide having a 3'-terminal blocking moiety, a priming oligonucleotide and a labeled detection probe. The promoter oligonucleotide targeted the complement of a sequence contained within the 5'-end of the target region and had the base sequence of SEQ ID NO: 14 aatttaatacgactcactatagggagagaacagatggggcacacaattcctagt, where the underlined portion of the promoter oligonucleotide constitutes a T7 promoter sequence (SEQ ID NO:3) and the non-underlined portion represents a hybridizing sequence (SEQ ID NO:13). The 3'-terminal blocking moiety of the promoter oligonucleotide consisted of the 3'-to-3' linkage described in Example 1. The priming oligonucleotide targeted a sequence contained within the 3'-end of the target region and had the base sequence of SEQ ID NO:15. The detection probe, which was comprised of 2'-O-methyl ribonucleotides, had the base sequence of SEQ ID NO:16 ggacaa*gcagaaccggaca and targeted a sequence contained within the target region. The asterisk indicates the position of a standard AE label joined to the probe by means of a non-nucleotide linker. See Arnold et al., U.S. Pat. No. 5,585,481.

The amplification reactions of this experiment were performed in replicates of 5, and each tube included 75 µL of the Amplification Reagent containing 0, 50, 100, 500, 1000 or 5000 copies of the transcript. Each tube was also provided with 40 pmol of the promoter oligonucleotide and 15 pmol of the priming oligonucleotide. The reaction mixtures were overlaid with 200 µL of the Oil Reagent, and the tubes were then sealed and hand-shaken horizontally for 5 to 10 seconds. To separate the complementary strands of the double-stranded transcript, the tubes were incubated in a heat block for 10 minutes at 95° C. At the end of this incubation, the tubes were removed from the heat block and rapidly cooled on ice for 5 minutes to promote association of the priming oligonucleotide and the targeted region of the transcript. The tubes were then incubated in a 41.5° C. water bath for 10 minutes. To initiate amplification, 25 µL of the Enzyme Reagent was added to the tubes, which were then sealed and hand-shaken horizontally for 5 to 10 seconds to fully mix the Amplification and Enzyme Reagents. Amplification was then carried out by returning the tubes to the 41.5° C. water bath for a 1 hour incubation.

Following amplification, detection of the amplification products was performed in the manner described in Example 2 using 100 fmol/reaction of the detection probe. The results of this experiment are set forth in Table 3 below and indicate 500 copy sensitivity for this amplification system, where an RLU value of 10,000 or greater constituted a positive result.

TABLE 3

Sensitivity of HPV-16 Amplification System

| Copy Number | Avg. RLU | % Positive Amplifications |
|---|---|---|
| 0 | 5410 | 0 |
| 50 | 5647 | 0 |
| 100 | 6018 | 0 |
| 500 | 19,928 | 80 |
| 1000 | 200,072 | 80 |
| 5000 | 371,641 | 100 |

Example 5

Comparison of Blocked and Unblocked Promoter Oligonucleotides

The purpose of this experiment was to evaluate the benefit of including a terminating oligonucleotide in the HCV amplification system of Example 1. See FIG. 1A. For this experiment, four different reaction mixtures were set up in replicates of 10 containing either 0 or 10 copies of the transcript of Example 1 in the presence or absence of a terminating oligonucleotide. The promoter, priming and terminating oligonucleotides were identical to those used in Example 1. Unlike Example 1, this experiment included two detection probes, both of which were made up of 2'-O-methyl ribonucleotides and targeted a sequence contained within the region of the transcript targeted for amplification. The first detection probe had the base sequence of SEQ ID NO:7 guacu*caccgguucc, and the second detection probe had the base sequence of SEQ ID NO:8 agaccacua*uggcucucccggg. Each detection probe had a "cold," or unlabeled version, and a "hot," or labeled version. (Cold probes were used in this experiment to prevent saturation of the hot probes in the presence of a vast excess of amplicon, thereby permitting the extent of amplification to be evaluated.) The asterisks indicate the positions of standard AE labels joined to the hot probes by means of non-nucleotide linkers. See Arnold et al., U.S. Pat. No. 5,585,481.

The amplification reactions were essentially carried out in the manner described in Example 2 using 30 pmol/reaction of the promoter oligonucleotide and 15 pmol/reaction of each of the priming and terminating oligonucleotides. Detection was performed as described in Example 2 using 100 fmol/reaction of each of the two hot probes and each of the two cold probes in amounts corresponding to the ratios indicated in Table 4 below. The averaged results are set forth in Table 4 in relative light units ("RLU") and demonstrate that only those reaction mixtures containing the terminating oligonucleotide had 10 copy level sensitivity in the HCV amplification system. The coefficient of variation values ("% CV") appearing in Table 4 for the different copy levels tested constitute the standard deviation of the replicates over the mean of the replicates as a percentage.

TABLE 4

Sensitivity of the HCV Amplification System in the Presence and Absence of a Terminating Oligonucleotide

| Copy Number | Terminating Oligonucleotide | Cold Prot/Hot Probe Ratio |
|---|---|---|
| 0 | + | 25:1 |
| 10 | + | 25:1 |
| 0 | − | 5:1 |
| 10 | − | 5:1 |

Example 6

Varying Length of Base Overlap Between Promoter Oligonucleotide and Terminating Oligonucleotide In this experiment, we studied the effect of varying the length of overlap between a blocked promoter oligonucleotide and a terminating oligonucleotide on amplification efficiency in the HCV amplification system of Example 1. The reaction mixtures were set up in replicates of four and each set was provided with 0 or 50 copies of the transcript of Example 1. The amount of overlap between the promoter oligonucleotide and the terminating oligonucleotide, if present, was 2, 4 or 6 bases for each set of reaction mixtures. The promoter oligonucleotide, the priming oligonucleotide, and the detection probes were identical to those used in Example 5. The cold probes and hot probes were used at a ratio of 4:1. The three terminating oligonucleotides of this experiment were made up of 2'-O-methyl ribonucleotides and had the following base sequences: (i) SEQ ID NO:42 agacgcuuucugcgugaagacagu (2 base overlap); (ii) SEQ ID NO:43 cuagacgcuuucugcgugaagaca (4 base overlap); and (iii) SEQ ID NO:38 (6 base overlap).

The amplification reactions were carried out in reaction tubes in the manner described in Example 5 using 30 pmol/reaction of the promoter oligonucleotide and 15 pmol/reaction each of the priming oligonucleotide and the terminating oligonucleotides. Detection was performed as described in Example 2 using 100 fmol/reaction of each of the two hot probes and 400 fmol/reaction of each of the two cold probes. The averaged results are set forth in Table 5 in relative light units ("RLU") and indicate that under the conditions tested, six bases of overlap between the promoter oligonucleotide and the terminating oligonucleotide is optimal for the HCV amplification system. The skilled artisan could apply this method to any amplification system to determine the optimal amount of overlap between a promoter oligonucleotide and a terminating oligonucleotide using nothing more than routine experimentation.

TABLE 5

Effect of Terminating Oligonucleotide/Promoter Oligonucleotide Base Overlap on Amplification Efficiency

| Copy Number | Terminating Oligonucleotide | Base Overlap | Avg. RLU |
|---|---|---|---|
| 0 | − | N/A | 29,593 |
|  | + | 2 | 25,430 |
|  | + | 4 | 27,128 |
|  | + | 6 | 27,732 |
| 50 | − | N/A | 265,250 |
|  | + | 2 | 339,833 |
|  | + | 4 | 253,577 |
|  | + | 6 | 1,904,911 |

Example 7

Comparison of Real-Time Amplification Assays in the Presence or Absence of a Terminating Oligonucleotide This experiment was conducted, to determine whether a terminating oligonucleotide improves amplification performance in a real-time amplification assay. For this experiment, we used the *Mycobacterium tuberculosis* amplification system of Example 2, which included the unblocked promoter oligonucleotide having the base sequence of SEQ ID NO:28, the priming oligonucleotide having the base sequence of SEQ ID NO:29, and the blocked terminating oligonucleotide having the base sequence of SEQ ID NO:39. Also included was a molecular beacon detection probe having the base sequence of SEQ ID NO:31. The detection probe was synthesized to include a BHQ-2 Black Hole Quencher™ Dye joined to its 3'-end using a BHQ-2 Glycolate CPG (Biosearch Technologies, Inc., Novato, Calif.; Cat. No. CG5-5042G-1) and a Cy™ 5 Dye joined to its 5'-end using a Cy™ 5-CE phosphoramidite (Glen Research; Cat. No. 105915-90). The reactions were run in the wells of a Thermo Labsystems White Cliniplate 96 (VWR International, Inc., West Chester, Pa.; Cat. No. 28298-610), and each reaction well contained 0, 100 or 1000 copies of the target nucleic acid of Example 2. For each copy number tested, there were four replicates which included the terminating oligonucleotide and four replicates which did not.

For amplification and detection, 75 μL of the Amplification Reagent was added to each reaction well, followed by the addition of 2 μL of a 0.1% (w/v) LLS buffer containing 50 copies/μL to each tube of one set of replicates and 2 μL of a 0.1% (w/v) LLS buffer containing 500 copies/μL to each tube of another set of replicates. The promoter oligonucleotide, the priming oligonucleotide and, when included, the terminating oligonucleotide were each added to the tubes in 5 pmol/reaction amounts, and 2 pmol/reaction of the detection probe was added to each tube. Target nucleic acid was provided to the reaction wells in the amounts indicated, and the reactions mixtures were overlaid with 80 μL of the Oil Reagent. The plate was sealed with a ThermalSeal RT™ Film (Sigma-Aldrich Corporation, St. Louis, Mo.; Product No. Z369675) and the contents of the plate were subjected to a 60° C. incubation for 15 minutes in a Solo HT Microplate Incubator (Thermo Electron Corporation, Waltham, Mass.; Model No. 5161580), followed by a 42° C. incubation for 10 minutes in the Solo HT Microplate Incubator. Next, 25 μL of the Enzyme Reagent (pre-heated to 42° C.) was added to each well and the contents were mixed several times using a pipette. The contents of the plate were then incubated at 42° C. for 120 minutes in a Biolumin™ 960 Micro Assay Reader (Molecular Dynamics Inc., Sunnyvale, Calif.) and fluorescence from the Cy™ 5 Dye channel was monitored as a function of time in one minute intervals. The results of this monitoring, which are graphically presented in FIGS. 4A-F, indicate that the terminating oligonucleotide dramatically enhanced amplification of the target sequence in the *Mycobacterium tuberculosis* real-time amplification assay.

Example 8

Terminating Oligonucleotides Versus Digestion Oligonucleotides

This experiment compared levels of amplification in the *Mycobacterium tuberculosis* amplification system of Example 2 using either a terminating oligonucleotide or a digestion oligonucleotide in the presence of a blocked or unblocked promoter oligonucleotide. The terminating oligonucleotide of this experiment was designed to bind to the targeted RNA and physically block the activity of the reverse transcriptase enzyme, while the digestion oligonucleotide, which was composed of DNA, was designed to bind to the targeted RNA and direct digestion of the substrate RNA by an RNAse H activity. Use of the terminating or digestion oligonucleotide results in the formation of a template-complementary strand, or cDNA, having a defined 3'-end. The promoter oligonucleotide is designed so that its template-binding portion hybridizes to a 3'-terminal sequence present in the template-complementary strand, thereby facilitating the formation of a double-stranded promoter sequence in the presence of the reverse transcriptase enzyme.

As in Example 2, the promoter oligonucleotide of this experiment had the base sequence of SEQ ID NO:28 and the priming oligonucleotide had the base sequence of SEQ ID NO:29. The terminating oligonucleotide was made up of 2'-O-methyl ribonucleotides having the base sequence of SEQ ID NO:44 caguuucccaggcuuauccc, and the digestion oligonucleotide had the base sequence of SEQ ID NO:45 gtattagacccagtttcccaggct. The 5'-ends of the terminating oligonucleotide the hybridizing sequence of the promoter oligonucleotide identified in Example 2 overlapped by four bases, and the first 14 bases extending from the 5'-end of the digestion oligonucleotide overlapped with the 5'-most 14 bases of the hybridizing sequence of the promoter oligonucleotide. The blocked promoter oligonucleotide, the terminating oligonucleotide, and the digestion oligonucleotide all included a 3'-terminal blocking moiety consisting of the 3'-to-3' linkage described in Example 1. And the detection probe had the base sequence of SEQ ID NO:32 gctcatccca*caccgctaaagc, where the asterisk indicates the position of a standard AE label joined to the probe by means of a non-nucleotide linker. See Arnold et al., U.S. Pat. No. 5,585,481.

A total of six different reactions were performed in replicates of two, as set forth in Table 6 below. Template positive reactions were each provided with 1 µL of a 0.1% (w/v) LLS buffer containing 50 copies/µL of the *Mycobacterium tuberculosis* target nucleic acid of Example 2, and template negative reactions included no target nucleic acid. Amplification and detection were essentially carried out as in Example 2 using 30 pmol/reaction each of the promoter and priming oligonucleotide, 5 pmol/reaction of the terminating oligonucleotides, 30 pmol/reaction of the digestion oligonucleotide, and 10 fmol/reaction of the detection probe. The results of these reactions, which were measured in relative light units ("RLU"), are presented in Table 6 and indicate that amplification in this amplification system was similar in the presence of either the terminating or the digestion oligonucleotide, although performance was somewhat better using the digestion oligonucleotide. Additionally, the results indicate that the level of amplification in this amplification system at this copy number was enhanced in the presence of the digestion oligonucleotide.

TABLE 6

Amplicon Production Using Terminating or Digestion Oligonucleotide

| Reaction | Template | Terminating (T) or Digestion (D) Oligonucleotide | Promoter Oligonucleotide | RLU |
| --- | --- | --- | --- | --- |
| 1 | Positive | T | Blocked | 319,449 |
| 2 | | T | Blocked | 254,181 |
| 3 | | T | Unblocked | 20,915 |
| 4 | | T | Unblocked | 3767 |
| 5 | | D | Blocked | 472,786 |
| 6 | | D | Blocked | 422,818 |
| 7 | | D | Unblocked | 162,484 |
| 8 | | D | Unblocked | 136,134 |
| 9 | | None | Blocked | 10,007 |
| 10 | | None | Blocked | 5052 |
| 11 | Negative | D | Blocked | 27,594 |
| 12 | | D | Blocked | 5157 |

Example 9

Capped Priming Oligonucleotides

This experiment studied the effect of including a priming oligonucleotide cap on side-product formation using the *Mycobacterium tuberculosis* amplification system of Example 2. A "cap" is a short oligonucleotide complementary to the 3'-terminal end of a priming oligonucleotide and includes a 3'-terminal blocking moiety to prevent extension from a terminal 3'-OH group. The cap is included to prevent the priming oligonucleotide from forming an oligonucleotide dimer with the promoter oligonucleotide, which could result in the formation of a functional double-stranded promoter sequence if the priming oligonucleotide is extended in the presence of a reverse transcriptase enzyme. As illustrated in FIG. 5A, the formation of an oligonucleotide dimer having a functional double-stranded promoter sequence could lead to the production of unwanted side-products in the presence of an RNA polymerase. While the cap inhibits oligonucleotide dimer formation, the cap can be readily displaced from the priming oligonucleotide through specific hybridization with the template sequence. A diagram of cap usage is shown in FIG. 6A.

For this experiment, we tested three different reaction conditions in replicates of two in the presence or absence of the *Mycobacterium tuberculosis* target nucleic acid of Example 2. The components of the three reaction conditions differed as follows: (i) the first set of reaction conditions included an unblocked promoter oligonucleotide, an uncapped priming oligonucleotide and a blocked terminating oligonucleotide; (ii) the second set of reaction conditions included a blocked promoter oligonucleotide, an uncapped priming oligonucleotide, and a blocked terminating oligonucleotide; and (iii) the third set of reaction conditions included a blocked promoter oligonucleotide, a priming oligonucleotide hybridized to a blocked cap at its 3'-terminal end, and a blocked terminating oligonucleotide. As in Example 2, the promoter oligonucleotide had the base sequence of SEQ ID NO:28 and the priming oligonucleotide had the base sequence of SEQ ID NO:29. The cap had the base sequence of SEQ ID NO:46 ctatc. The terminating oligonucleotide was made up of 2'-O-methyl ribonucleotides having the base sequence of SEQ ID NO:44 caguuucccaggcuuauccc. And the terminating oligonucleotide, the promoter oligonucleotide, when blocked, and the cap all included a 3'-terminal blocking moiety consisting of the 3'-to-3' linkage described in Example 1.

Prior to initiating amplification, the priming oligonucleotide and the cap were pre-hybridized in a 10 mM NaCl solution containing the priming oligonucleotide and the cap at a 1:1 ratio. The facilitate hybridization, the reaction tubes containing the solution were incubated in a 95° C. water bath for 10 minutes and then cooled at room temperature for 2 hours. Following this pre-hybridization step, amplification was carried out as in Example 2 using 30 pmol/reaction each of the promoter oligonucleotide and the capped priming oligonucleotide and 5 pmol/reaction of the terminating oligonucleotide, where each reaction mixture was also provided with 1 µL of a 0.1% (w/v) LLS buffer containing 10,000 copies/µL of the target nucleic acid. After amplification, a 5 µL sample was taken from each tube, diluted 1:1 with a 10× BlueJuice™ Gel Loading Buffer (Invitrogen; Cat. No. 10816-015) which was diluted to 2× with TBE (Tris-Borate-EDTA), and loaded onto an E-Gel® Single Comb Gel (4% high resolution agarose) which was pre-stained with ethidium bromide (Invitrogen; Cat. No. G5018-04). The gels were run on an E-Gel® Base (Invitrogen; Cat. No. G5100-01) at 80 volts for 30 minutes. The gels were then visualized on a FisherBiotech® Ultraviolet Transilluminator and photographed with a handheld camera using Polaroid 667 film.

Figure 7A:
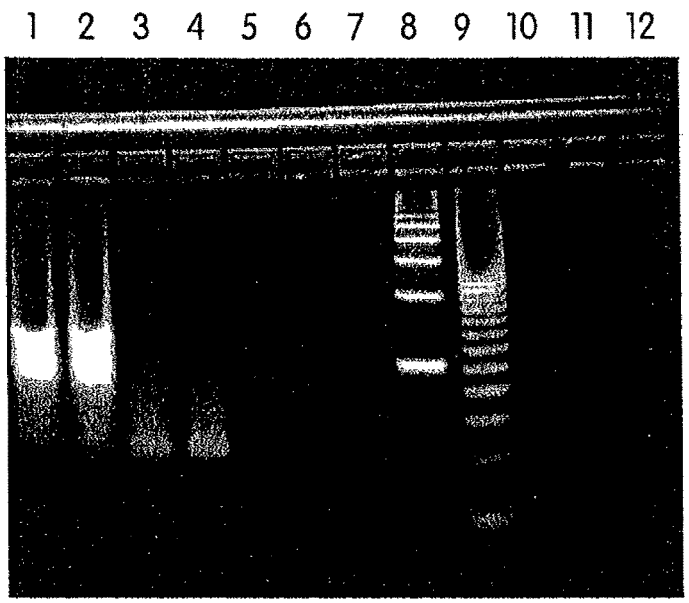
FIGS. 7A and 7B depict non-denaturing agarose gels showing the effect of a capping oligonucleotide on side-product formation.
Figure 7B:
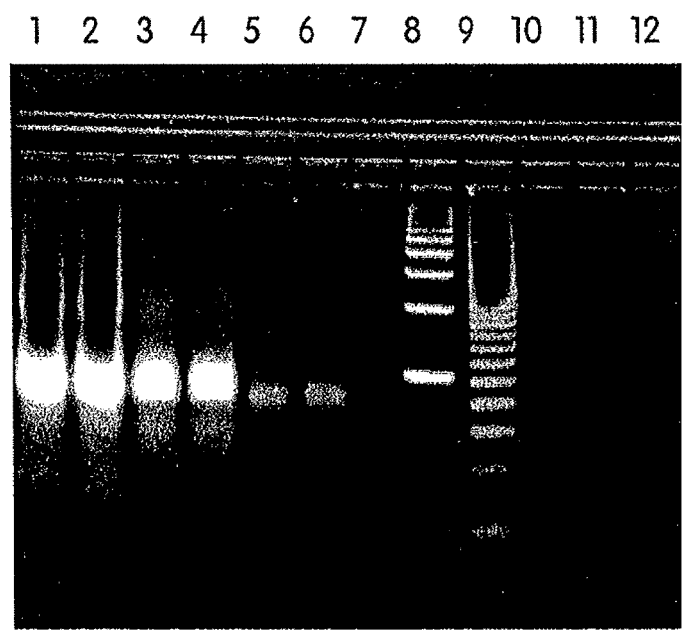

The results of this experiment are illustrated in the photographed gels of FIG. 7A (template negative gel) and FIG. 7B (template positive gel). The numbers above the pictured gels indicate distinct lanes, where lane 7 is blank, lane 8 is a 100 base pair RNA ladder, lane 9 is a 20 base pair RNA ladder, and the remainder of the lanes contain products from the following reaction mixtures: (i) lanes 1 and 2 correspond to reaction mixtures containing the unblocked promoter oligonucleotide, the uncapped priming oligonucleotide, and the blocked terminating oligonucleotide; (ii) lanes 3 and 4 correspond to reaction mixtures containing the blocked promoter oligonucleotide, the uncapped priming oligonucleotide, and the terminating oligonucleotide; and (iii) lanes 5 and 6 correspond to reaction mixtures containing the blocked promoter oligonucleotide, the capped priming oligonucleotide, and the terminating oligonucleotide. The results clearly show that capping the priming oligonucleotide resulted in a further reduction in side-product formation (the side-products, which are oligonucleotide dimers in these reactions, are in the 20-mer to 60-mer range, whereas the amplicon would be greater than 100 bases in length).

Example 10

Looped Priming Oligonucleotides

In this experiment, the effect of looped priming oligonucleotides on amplification in the *Mycobacterium tuberculosis* amplification system of Example 2 was examined. Looped priming oligonucleotides are a variety of the priming oligonucleotides and caps evaluated in Example 9. A looped priming oligonucleotide includes a cap which is joined at its 3'-end to the 5'-end of the priming oligonucleotide by means of a non-nucleotide linker (e.g., abasic nucleotides). One advantage of a looped priming oligonucleotide is that reassociation of the priming oligonucleotide and the cap, in the absence of the targeted template, is faster when the two oligonucleotides are maintained in close proximity to each other. Another advantage of a looped priming oligonucleotide is that the priming oligonucleotide and the cap can be generated in a single synthesis procedure, as opposed to the time intensive syntheses of separate priming and cap oligonucleotides.

Comparison was made between an uncapped priming oligonucleotide and looped priming oligonucleotides having caps of varying lengths. The promoter, priming and terminating oligonucleotides were the same as those used in Example 9, and the detection probe was the same as detection probe I used in Example 2. The detection probe was provided to the reaction mixtures in both "cold" and "hot" forms, for the reasons described in Example 5, and the cold:hot probe ratio of each reaction mixture was 250:1. The looped priming oligonucleotides had the following sequences, where each "n" represents an abasic nucleotide (Glen Research; Cat. No. 10-1924-xx):

```
Looped Priming Oligonucleotide I (LPO I):
                                       SEQ ID NO: 47
ctatttnngccgtcaccccaccaacaagctgatag;

Looped Priming Oligonucleotide II (LPO II):
                                       SEQ ID NO: 48
ctatcnnnnngccgtcaccccaccaacaagctgatag;

Looped Priming Oligonucleotide III (LPO III):
                                       SEQ ID NO: 49
ctatnnnnngccgtcaccccaccaacaagctgatag;

Looped Priming Oligonucleotide IV (LPO IV):
                                       SEQ ID NO: 50
ctatcannnnngccgtcaccccaccaacaagctgatag;

Looped Priming Oligonucleotide V (LPO V):
                                       SEQ ID NO: 51
ctatcnnnngccgtcaccccaccaacaagctgatag;

Looped Priming Oligonucleotide VI (LPO VI):
                                       SEQ ID NO: 52
ctatcannnngccgtcaccccaccaacaagctgatag;
and Looped Priming Oligonucleotide VII (LPO VII):
                                       SEQ ID NO: 53
ctatcagcttgttggnnnnngccgtcaccccaccaacaagctgatag.
```

A different reaction mixture was prepared for each priming oligonucleotide, and the reaction mixtures were tested in replicates of three using 1000 copies of the *Mycobacterium tuberculosis* target nucleic acid of Example 2 obtained from 0.1% (w/v) LLS buffer containing 1000 copies/µL of the target nucleic acid. The amplification and detection steps were carried out as in Example 2 using 30 pmol/reaction each of the promoter and priming oligonucleotides, 5 pmol/reaction of the terminating oligonucleotide, 10 fmol/reaction of the hot probe, and 2.5 pmol/reaction of the cold probe. Signal from the tubes was measured in relative light units ("RLU") and the average RLU values are presented in Table 7 below. The results indicate that the template can be amplified using a looped priming oligonucleotide, and that a looped priming oligonucleotide having four abasic groups and a five base cap is optimal for the *Mycobacterium tuberculosis* amplification system.

TABLE 7

Effect of Looped Priming Oligonucleotides on Amplification

| Priming Oligonucleotide | Avg. RLU |
|---|---|
| Uncapped | 430,060 |
| LPO I | 292,541 |
| LPO II | 260,559 |
| LPO III | 281,304 |
| LPO IV | 136,398 |
| LPO V | 372,119 |
| LPO VI | 171,382 |
| LPO VII | 20,045 |

Example 11

Comparison of Looped Priming Oligonucleotides and Caps

This experiment evaluated the ability of looped priming oligonucleotides to inhibit primer-dependent side-product formation. For this experiment, looped priming oligonucleotides LPO V and LPO VII of Example 10 were compared with an uncapped priming oligonucleotide and a priming oligonucleotide having a 14 base cap. The uncapped and capped priming oligonucleotides were the same as the uncapped priming oligonucleotide used in Example 10, and the cap had the base sequence of SEQ ID NO:54 ctatcagcttgttg (the cap and the priming oligonucleotide were pre-hybridized as in Example 9). The terminating oligonucleotide was the same as the terminating oligonucleotide used in Example 10, and the detection probe targeted the complement of the priming oligonucleotide and had the base sequence of SEQ ID NO:29 gccgtcacccc*accaacaagctgatag, where the asterisk indicates the position of a standard AE label joined to the probe by means of a non-nucleotide linker. See Arnold et al., U.S. Pat. No. 5,585,481. The detection probe was provided to the reaction mixtures in both "cold" and "hot" forms, for the reasons described in Example 5, and the cold:hot probe ratio of each reaction mixture was 4000:1. As with the promoter and terminating oligonucleotides, the cap had a 3'-terminal blocking moiety consisting of the 3' to 3' linkage described in Example 1.

The reaction mixtures were all template-free and tested in replicates of three, with a different set of reaction mixtures being prepared for each priming oligonucleotide. The amplification and detection steps were carried out as in Example 2 using 30 pmol/reaction each of the promoter and priming oligonucleotides, 5 pmol/reaction of the terminating oligonucleotide, 20 fmol/reaction of the hot probe, and 80 pmol/reaction of the cold probe. Signal from the tubes was measured in relative light units ("RLU") and the averages of those RLU values are set forth in Table 9 below. The results indicate that the capped priming oligonucleotide inhibited primer-dependent side-product formation to a greater extent than did the looped priming oligonucleotides, although use of the looped priming oligonucleotides resulted in less primer-dependent side-product formation than when the uncapped priming oligonucleotide was used in this amplification system.

TABLE 8

Inhibition of Primer-Dependent Side-product Formation Using Looped Priming Oligonucleotides and Caps

| Priming Oligonucleotide | Avg. RLU |
|---|---|
| Uncapped | 2,246,565 |
| LPO V | 1,497,699 |
| LPO VII | 1,040,960 |
| Capped | 106,134 |

Example 12

Comparison of RNA Transcript Production in the Presence and Absence of Extender Oligonucleotides This experiment examined the effect of extender oligonucleotides on amplicon production in amplification reaction mixtures containing a blocked promoter oligonucleotide. The extender oligonucleotides of this experiment were either blocked or unblocked and had the base sequence of SEQ ID NO:55 cctccaggacccccctcccgggagagccata. A 3'-end blocked terminating oligonucleotide was included that was made up of 2'-O-methyl ribonucleotides having the base sequence of SEQ ID NO:56 auggcuagacgcuuucugcgugaaga. The target nucleic acid ("target"), priming oligonucleotide and promoter oligonucleotide were the same as those used in Example 1. The blocking moiety of each blocked oligonucleotide used in this experiment was a 3'-terminal blocking moiety consisting of the 3'-to-3' linkage described in Example 1. Cold and hot probes were used for detection of transcription products and had the sequence of SEQ ID NO:7. The hot probe of this experiment was identical to the first detection probe used in Example 5.

Six groups of amplification reaction mixtures were tested in replicates of four as follows: (i) no extender oligonucleotide and no target (group I); (ii) no extender oligonucleotide and 100 copies of target (group II); (iii) blocked extender oligonucleotide and no target (group III); (iv) blocked extender oligonucleotide and 100 copies of target (group IV); (v) unblocked extender oligonucleotide and no target (group V); (iv) unblocked extender oligonucleotide and 100 copies of target (group VI). Reaction tubes from the six groups were set-up with 30 μL Amplification Reagent containing 6 pmol of the priming oligonucleotide, 4 pmol of the promoter oligonucleotide and 0.8 pmol of the terminating oligonucleotide. The reaction tubes of groups III and IV contained 4 pmol of the blocked extender oligonucleotide, and the reaction tubes of groups V and VI contained 4 pmol of the unblocked extender oligonucleotide. As indicated above, the reaction tubes of groups II, IV and VI further contained 100 copies of target, while those of groups I, III and V contained no target. The reaction mixtures were overlaid with 200 μL Oil Reagent, and the tubes were then sealed and vortexed for 10 seconds before being incubated in a 60° C. water bath for 10 minutes. The tubes were then transferred to a 41.5° C. water bath and incubated for 15 minutes before adding 10 μL Enzyme Reagent. After adding Enzyme Reagent, the tubes were again sealed and hand-shaken horizontally for 5 to 10 seconds to fully mix the components of the reaction mixtures. The tubes were returned to the 41.5° C. water bath and incubated for an additional 60 minutes to permit amplification of the target sequence. Following amplification, the tubes were removed from the 41.5° C. water bath and placed in an ice water bath for two minutes.

Detection of RNA transcription products was performed essentially as described in Example 2 (reaction tubes were vortexed rather than hand-shaken) using 100 fmol/reaction of the hot probe and 300 pmol/reaction of the cold probe. The averaged results are set forth in Table 9 in relative light units ("RLU") and demonstrate that the extender oligonucleotides of this experiment contributed to faster rates of amplification. The coefficient of variation values ("% CV") appearing in Table 9 for the different reaction conditions tested constitute the standard deviation of the replicates over the mean of the replicates as a percentage.

TABLE 9

Effect of Extender Oligonucleotides on Amplicon Production

| Copy Number | Extender Oligonucleotide | Avg. RLU | % CV |
|---|---|---|---|
| 0 | None | 4239 | 13 |
| 100 | None | 70,100 | 28 |
| 0 | Blocked | 4721 | 30 |
| 100 | Blocked | 337,964 | 12 |
| 0 | Unblocked | 13,324 | 76 |
| 100 | Unblocked | 869,861 | 12 |

Example 13

Amplification of a DNA Target Sequence

This experiment was conducted to determine the sensitivity of an amplification system according to the present invention for a target region contained within double-stranded DNA ("dsDNA"). The exemplary dsDNA used in this experiment was a cloned transcript derived from the orfX gene of a methicillin-resistant strain of *Staphylococcus aureus*. Included for amplification were a priming oligonucleotide, a displacer oligonucleotide, a terminating oligonucleotide and a promoter oligonucleotide. The priming oligonucleotide targeted a sequence contained within the 3'-end of the target region and had the base sequence of SEQ ID NO:35; the displacer oligonucleotide targeted a sequence present in a target nucleic acid containing the target region 5' to the target region and had the base sequence of SEQ ID NO:57 cuugct-caattaacacaacccgcatc, where the underlined bases were LNAs; the terminating oligonucleotide targeted a sequence present in the target nucleic acid 3' to the target region and had the base sequence of SEQ ID NO:58 gcgttggttcaauuc, where the underlined bases were LNAs (the terminating oligonucleotide was not fully comprised of LNAs to limit folding); and the promoter oligonucleotide had the base sequence of SEQ ID NO:34 aatttaatacgactcactatagggagaacgcatgacccaa gggcaaagcgactttg, where the underlined portion was a T7 promoter sequence (SEQ ID NO:3) and the remainder was a hybridizing sequence (SEQ ID NO:33) that targeted the complement of a sequence contained within the 5'-end of the target region. The promoter oligonucleotide and the terminating oligonucleotide both included a 3'-terminal blocking moiety consisting of the 3'-to-3' linkage described in Example 1. Detection was carried out in real-time with a molecular torch detection probe having the base sequence of SEQ ID NO:59 ccgucauuggcggaucagacgg. The base sequence of this probe was comprised of 2'-O-methylribonucleotides and nucleotides 17 and 18, reading 5'-to-3', were joined to each other by a 9-carbon linker. The detection probe was synthesized to include interacting DABCYL and FAM labels using 3'-DABCYL CPG (Prime Synthesis, Inc., Aston, Pa.; Cat. No. N-9756-10) and a 6-FAM phosphoramidite joined to the 5'-end (BioGenex Inc., San Ramon, Calif.; Cat. No. BGX-3008-01). The probe was also synthesized to include a 9-carbon linker positioned between nucleotides 17 and 18 reading 5'-to-3' (Glen Research Corporation, Sterling, Va.; Cat. No. 10-1909-90). The synthesized probe was purified by polyacrylamide gel electrophoresis and reverse phase HPLC. The target binding portion of the probe consisted of SEQ ID NO:37.

The amplification reactions of this experiment were performed in replicates of six for each copy number and, for this, each of twelve test wells of a microtiter plate was provided with 30 µL of an amplification reagent comprising 44.1 mM HEPES, 2.82% (w/v) trehalose, 30.6 mM $MgCl_2$, 33 mM KCl, 0.3% (v/v) ethanol, 0.1% (w/v) methyl paraben, 0.02% (w/v) propyl paraben, 9.41 mM rATP, 1.8 mM rCTP, 11.8 rGTP, 1.8 mM UTP, 0.47 mM dATP, 0.47 mM dCTP, 0.47 mM dGTP, 0.47 mM dTTP, 15 pmol priming oligonucleotide, 8 pmol displacer oligonucleotide, and 0.5 pmol terminating oligonucleotide at pH 7.7. Each well also contained 0, 10, 100, 1000 or 10,000 copies of the transcript. The plate was covered with a sealing card and incubated for 10 minutes at 95° C. in the equivalent of a DNA Engine Opticon® 2 Real-Time PCR Detection System (Bio-Rad Laboratories, Hercules, Calif.; Cat. No. CFD3220) to denature the double-stranded transcript, and then for 5 minutes at 42° C. to promote hybridization of the priming oligonucleotide, the displacer oligonucleotide and the terminating oligonucleotide to the target nucleic acid. After incubating, the plate was removed from the detection system and 10 µL of an enzyme reagent was added to each test well to initiate amplification. The enzyme reagent comprised 58 mM HEPES, 3.03% (w/v) trehalose, 50 mM N-acetyl-L-cysteine, 1.04 mM EDTA, 120 mM KCl, 10% (w/v) TRITON® X-100, 20% (v/v) glycerol, 15 pmol promoter oligonucleotide, 8 pmol detection probe, 360 RTU/µL MMLV reverse transcriptase ("RT"), and 80 U/µL T7 RNA polymerase at pH 7.0, where one RTU of RT activity incorporates 1 nmol of dT into a substrate in 20 minutes at 37° C. and one U of T7 RNA polymerase activity produces 5 fmol of RNA transcript in 20 minutes at 37° C. Following enzyme addition, the plate was placed on a Thermomixer R (Eppendorf North America, Inc., Westbury, N.Y.; Cat. No. 5355 29716) pre-warmed to 44° C., covered with a sealing card, and agitated for 30 seconds at 1400 rpm. The plate was returned to the 42° C. detection system, where an amplification reaction monitored in real-time was carried out for 100 minutes, with fluorescent readings being taken every 24 seconds. Detection depended upon conformational changes in the probes hybridized to amplification products, thereby resulting in the emission of detectable, fluorescent signals.

Figure 8:
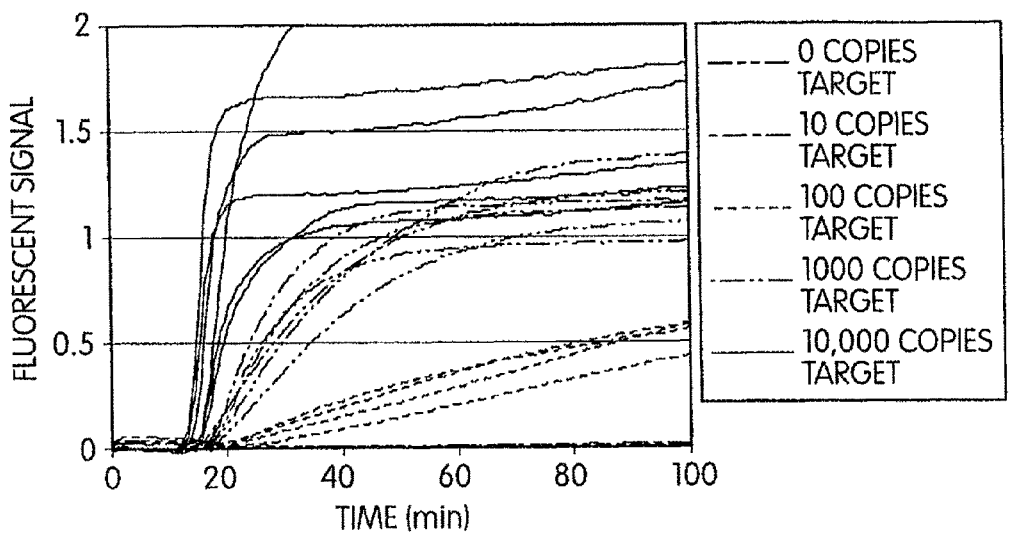
FIG. 8 shows the real-time accumulation of amplification products in a *Staphylococcus aureus* system according to a method of the present invention. The target nucleic acid was double-stranded DNA, which was tested at four copy levels against a negative control.

The results of this experiment are illustrated graphically in FIG. 8, where time in minutes is plotted on the x-axis and relative fluorescent signal is plotted on the y-axis. The data show that this amplification system had a sensitivity of at least 1000 copies of transcript. None of the control samples (0 transcript) exhibited detectable amplification.

Example 14

Comparison of Systems for Amplifying a DNA Target Sequence

A set of experiments was conducted to compare the sensitivities of various related amplification systems of the present invention for a target region contained within double-stranded DNA. Like Example 13, the exemplary target nucleic acid used in this experiment was a cloned transcript derived from the orfX gene of a methicillin-resistant strain of *Staphylococcus aureus*. The priming oligonucleotide used in these experiments had the base sequence of SEQ ID NO:36. The remainder of the oligonucleotides were the same as those of Example 13. Except for the first experiment, each of the experiments excluded one of the following components of Example 13: (i) a terminating oligonucleotide; (ii) a displacer oligonucleotide; (iii) a priming oligonucleotide; and (iv) heat to denature the double-stranded target. The experiments were run in replicates of twelve following the general protocol of Example 13. The sets of replicates contained either 0 or 1000 copies of the transcript.

Figure 9A:
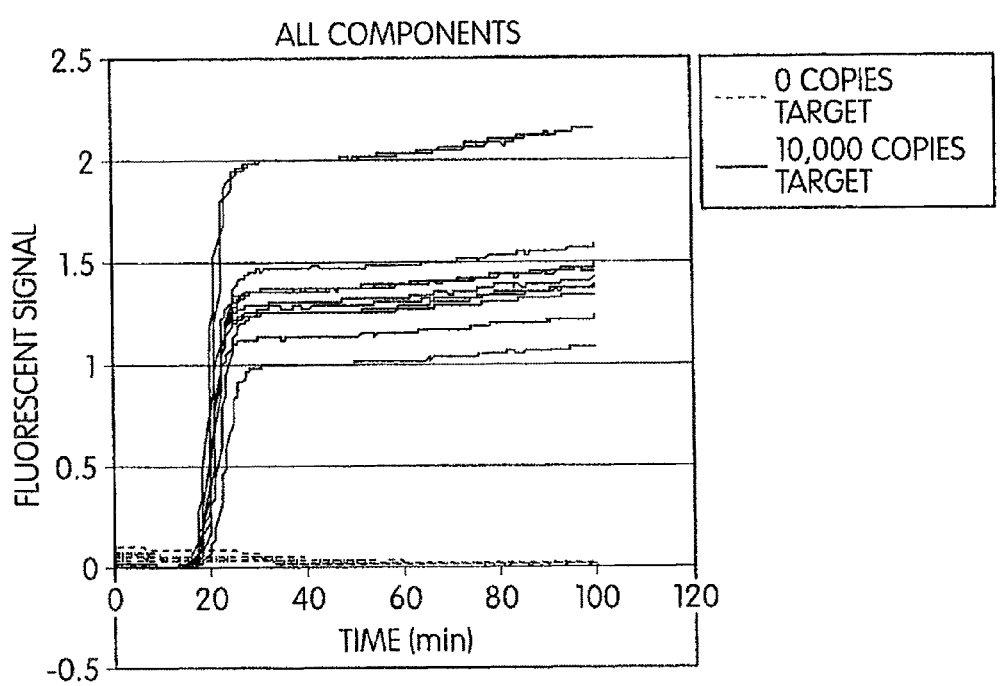
FIG. 9 shows the real-time accumulation of amplification products in five different *Staphylococcus aureus* systems according to methods of the present invention. The target nucleic acid for each system was double-stranded DNA, and each was system was tested at 10,000 copies of target against a negative control. The first system (FIG. 9A) employed the method of FIG. 1D, and each of the remaining systems excluded a component of this method. The method of FIG. 9B excluded the terminating oligonucleotide; the method of FIG. 9C excluded the displacer oligonucleotide; the method of FIG. 9D excluded the priming oligonucleotide; and the method of FIG. 9E excluded a denaturation step.
Figure 9B:
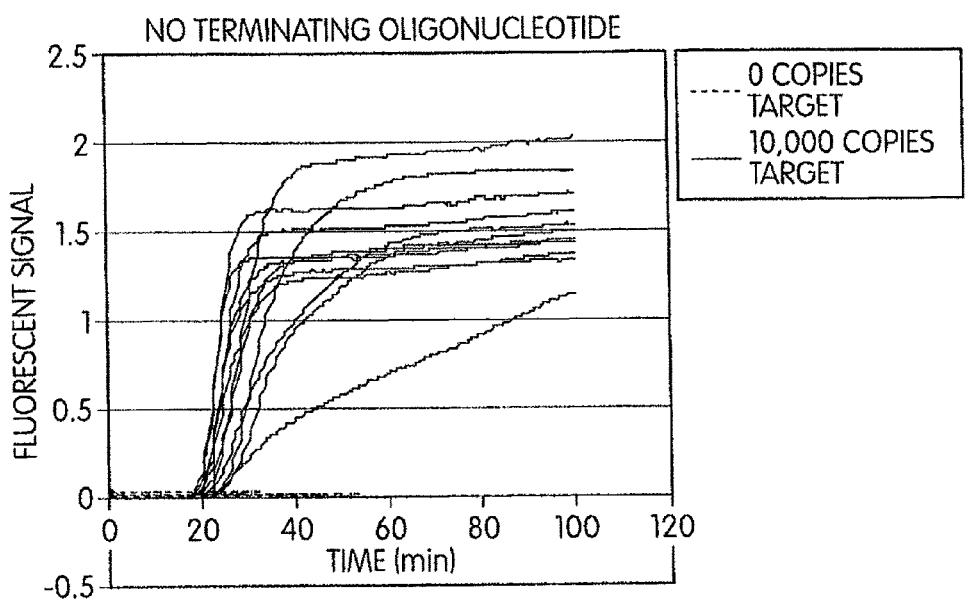
Figure 9C:
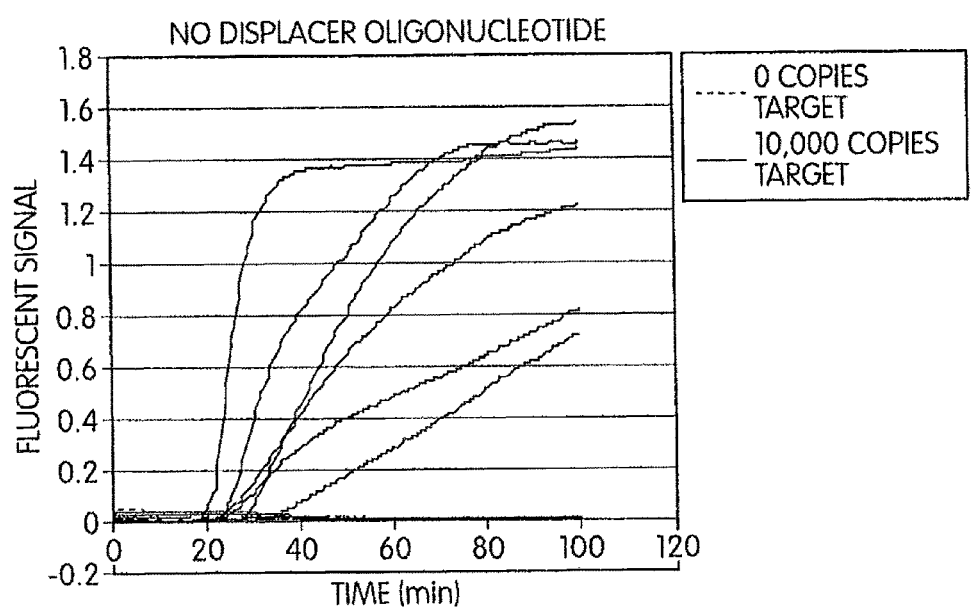
Figure 9D:
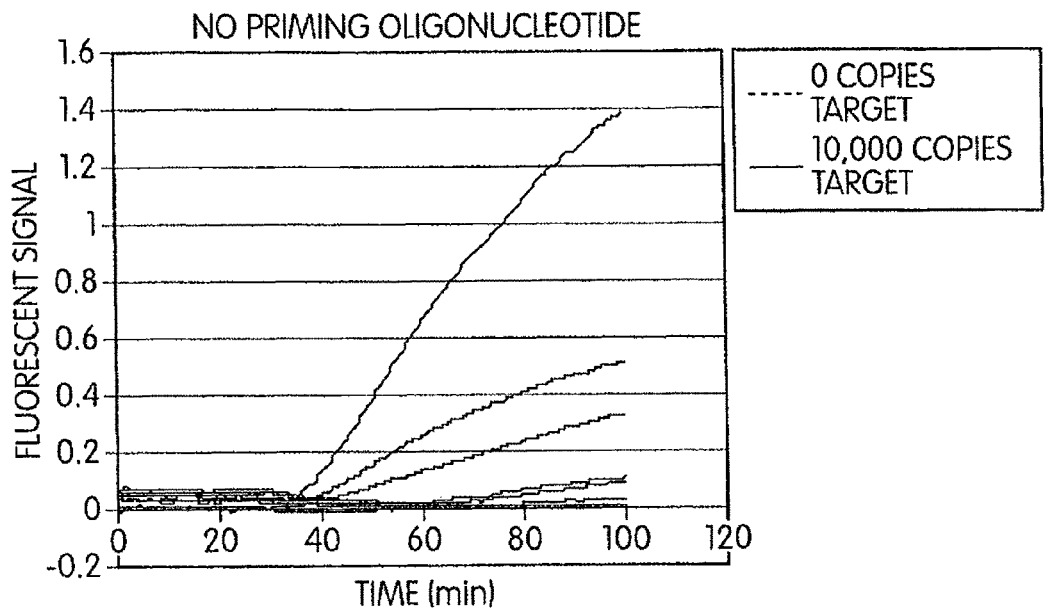
Figure 9E:
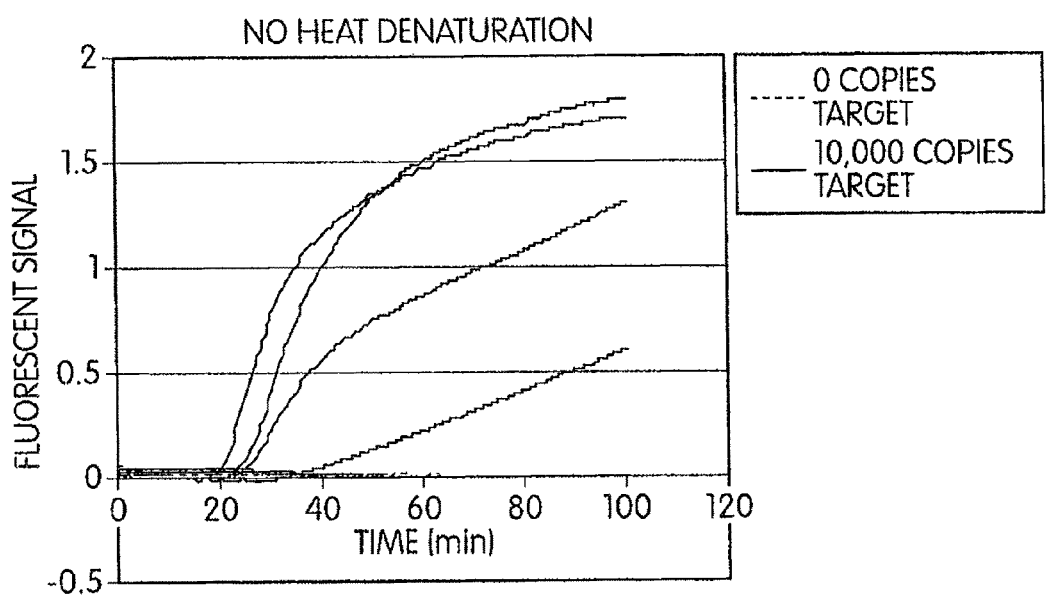

The results of this experiment are illustrated graphically in FIGS. 9A-E, where, again, time in minutes is plotted on the x-axis and relative fluorescent signal is plotted on the y-axis. The results of these experiments show the following: (i) all replicates containing the target were positive when the amplification system was not modified (see FIG. 9A); (ii) all replicates containing target were positive when the terminating oligonucleotide was excluded from the reaction mixture (see FIG. 9B); (iii) 6 out of 12 replicates containing the target were positive when the displacer oligonucleotide was excluded from the reaction mixture (see FIG. 9C); (iv) 3 out of 12 replicates containing the target were positive when the priming oligonucleotide was excluded from the reaction mixture (see FIG. 9D); and (v) 4 out of 12 replicates containing the target were positive when the double-stranded target was not exposed to heat-denaturing conditions (i.e., 95° C. heat step) prior to enzyme addition (see FIG. 9E). None of the control samples (0 transcript) exhibited detectable amplification.

\* \* \*

While the present invention has been described and shown in considerable detail with reference to certain preferred embodiments, those skilled in the art will readily appreciate other embodiments of the present invention. Accordingly, the present invention is deemed to include all modifications and variations encompassed within the spirit and scope of the following appended claims.

The invention claimed is:

1. A kit for use in amplifying a DNA target sequence, said kit comprising:

a priming oligonucleotide which hybridizes to the 3'-end of a DNA target sequence such that a primer extension reaction can be initiated therefrom;

a promoter oligonucleotide comprising first and second regions, wherein said first region has a base sequence which corresponds to a region at the 5'-end of said target sequence and which hybridizes to a 3'-region of a DNA primer extension product comprising said priming oligonucleotide, wherein said second region is a promoter for an RNA polymerase and is situated 5' to said first region, and wherein said promoter oligonucleotide is modified to prevent the initiation of DNA synthesis therefrom; and a displacer oligonucleotide which hybridizes to a target nucleic acid containing said target sequence upstream from said priming oligonucleotide such that a primer extension reaction can be initiated therefrom, provided that any oligonucleotide included in said kit that comprises a promoter for an RNA polymerase is modified to prevent the initiation of DNA synthesis therefrom, provided that said kit does not include a restriction endonuclease, and further provided that said priming oligonucleotide does not include an RNA region which hybridizes to said target nucleic acid and which is selectively degraded by an enzyme activity when hybridized to said target nucleic acid.

2. The kit of claim 1, wherein said priming oligonucleotide consists of deoxynucleotides and/or analogs thereof.

3. The kit of claim 1, wherein said promoter oligonucleotide is modified to include a blocking moiety situated at its 3'-terminus.

4. The kit of claim 3, wherein said blocking moiety of said promoter oligonucleotide comprises a substituent selected from the group consisting of: a modified nucleotide, a nucleotide or a nucleotide sequence having a 3'-to-5' orientation, a 3' alkyl group, a 3'2'-dideoxynucleotide, a 3' cordycepin, a 3' alkane-diol residue, a 3' non-nucleotide moiety, a nucleotide sequence non-complementary to said target sequence, a nucleic acid binding protein, and mixtures thereof.

5. The kit of claim 1, wherein said promoter oligonucleotide further comprises an insertion sequence positioned between or adjacent to said first and second regions, and wherein the presence of said insertion sequence in said promoter oligonucleotide enhances the rate at which said RNA products are formed.

6. The kit of claim 1 further comprising a chemical denaturant for rendering single-stranded a double-stranded DNA complex.

7. The kit of claim 1 further comprising a reverse transcriptase having an RNAse H activity, wherein said kit does not include an enzyme other than said reverse transcriptase having an RNAse H activity.

8. The kit of claim 1 further comprising an enzyme, other than a reverse transcriptase, having an RNAse H activity.

9. The kit of claim 1, wherein a 5'-region of said displacer oligonucleotide includes one or more modifications for increasing the binding affinity of said displacer oligonucleotide for said target nucleic acid, and wherein said modifications do not prevent said displacer oligonucleotide from being extended in a primer extension reaction.

10. The kit of claim 9, wherein said modifications are spaced at least 15 bases from the 3'-terminus of said displacer oligonucleotide.

11. The kit of claim 9, wherein said modifications are LNAs.

12. The kit of claim 1, wherein said displacer oligonucleotide hybridizes to said target nucleic acid such that the 3'-terminal base of said displacer oligonucleotide is adjacent to the 5'-terminal base of said priming oligonucleotide.

13. The kit of claim 1, wherein said displacer oligonucleotide hybridizes to said target nucleic acid such that the 3'-terminal base of said displacer oligonucleotide is spaced from 5 to 35 bases from the 5'-terminal base of said priming oligonucleotide.

14. The kit of claim 1, wherein at least one of said priming oligonucleotide and said displacer oligonucleotide includes a cap hybridized to the 3'-end thereof, said cap comprising a base region complementary to at least 3 bases at the 3'-end of said priming oligonucleotide or said displacer oligonucleotide, wherein the 5'-terminal base of said cap is complementary to the 3'-terminal base of said priming oligonucleotide or said displacer oligonucleotide, and wherein said cap is modified to prevent the initiation of DNA synthesis therefrom.

15. The kit of claim 14, wherein said cap is complementary to no more than 8 bases at the 3'-end of said priming oligonucleotide or said displacer oligonucleotide.

16. The kit of claim 14, wherein said cap prevents non-specific hybridization between said priming oligonucleotide or said displacer oligonucleotide and said promoter oligonucleotide when each said cap is hybridized to said priming oligonucleotide or said displacer oligonucleotide.

17. The kit of claim 14, wherein said cap is a capping oligonucleotide modified to include a blocking moiety situated at its 3'-terminus.

18. The kit of claim 14, wherein the 3'-end of said cap is covalently attached to the 5'-end of said priming oligonucleotide or said displacer oligonucleotide, and wherein said cap hybridizes to the 3'-end of said priming oligonucleotide or said displacer oligonucleotide by forming a loop.

19. The kit of claim 18, wherein said cap is joined to said priming oligonucleotide or said displacer oligonucleotide via a linker region.

20. The kit of claim 19, wherein said linker region comprises at least 5 nucleotides.

21. The kit of claim 19, wherein said linker region is a non-nucleotide linker.

22. The kit of claim 1 further comprising a binding molecule which binds to a target nucleic acid containing said target sequence adjacent to or near the 5'-end of said target sequence.

23. The kit of claim 22, wherein said binding molecule comprises an oligonucleotide having a blocking moiety situated at its 3'-terminus to prevent the initiation of DNA synthesis therefrom.

24. The kit of claim 22, wherein said binding molecule comprises LNAs.

25. The kit of claim 22, wherein said binding molecule is a terminating oligonucleotide.

26. The kit of claim 25, wherein the 5'-end of said terminating oligonucleotide is complementary to at least two bases at the 5'-end of said first region of said promoter oligonucleotide.

27. The kit of claim 25, wherein the 5'-end of said terminating oligonucleotide is complementary to at least three but no more than ten bases at the 5'-end of said first region of said promoter oligonucleotide.

28. The kit of claim 22, wherein said binding molecule is a modifying oligonucleotide.

29. The kit of claim 28, wherein said modifying oligonucleotide is a digestion oligonucleotide.

30. The kit of claim 1 further comprising an extender oligonucleotide which hybridizes to a region of said primer extension product 3' to said promoter oligonucleotide of said promoter oligonucleotide:primer extension product hybrid, such that an extender oligonucleotide:primer extension product hybrid is formed.

31. The kit of claim 30, wherein said extender oligonucleotide further comprises a blocking moiety situated at its 3' terminus to prevent the initiation of DNA synthesis therefrom.

32. The kit of claim 30, wherein said extender oligonucleotide hybridizes to said primer extension product such that the 5'-terminal base of said extender oligonucleotide is spaced within three nucleotides of the 3'-terminal base of said promoter oligonucleotide.

33. The kit of claim 30, wherein said extender oligonucleotide hybridizes to said primer extension product adjacent said promoter oligonucleotide.

34. The kit of claim 1 further comprising a detection probe which hybridizes to said target sequence.

35. The kit of claim 34, wherein said detection probe includes a detectable label.

* * * * *